(12) United States Patent
Csatary et al.

(10) Patent No.: US 8,377,450 B2
(45) Date of Patent: Feb. 19, 2013

(54) CLONE OF NEWCASTLE DISEASE VIRUS, ITS MANUFACTURE AND ITS APPLICATION IN THE MEDICAL TREATMENT OF CANCER

(75) Inventors: Laszlo K. Csatary, Fort Lauderdale, FL (US); Christine M. Csatary, Fort Lauderdale, FL (US)

(73) Assignee: United Cancer Research Institute, Alexandria, VA (US)

( * ) Notice: Subject to any disclaimer, the term of this patent is extended or adjusted under 35 U.S.C. 154(b) by 80 days.

(21) Appl. No.: 12/806,494

(22) Filed: Aug. 13, 2010

(65) Prior Publication Data

US 2011/0129446 A1 Jun. 2, 2011

Related U.S. Application Data

(60) Provisional application No. 61/283,154, filed on Nov. 30, 2009.

(30) Foreign Application Priority Data

Nov. 30, 2009 (EP) ..................................... 09075536

(51) Int. Cl.
*A61K 39/17* (2006.01)
*A61K 48/00* (2006.01)

(52) U.S. Cl. .................................... 424/211.1; 424/93.1
(58) Field of Classification Search ........................ None
See application file for complete search history.

(56) References Cited

U.S. PATENT DOCUMENTS

| 5,124,148 | A | 6/1992 | Csatary |
| 5,215,745 | A | 6/1993 | Csatary |
| 5,273,745 | A | 12/1993 | Schirrmacher |
| 5,602,023 | A | 2/1997 | Csatary |
| 6,153,199 | A | 11/2000 | Audonnet |
| 7,056,689 | B1 | 6/2006 | Lorence |
| 2006/0018884 | A1* | 1/2006 | Csatary et al. ............... 424/93.6 |

FOREIGN PATENT DOCUMENTS

| EP | 1486211 | 12/2004 |
| EP | 1297121 | 5/2005 |
| EP | 1032269 | 8/2007 |
| EP | 1905304 | 4/2008 |
| EP | 1314431 | 7/2008 |
| EP | 2009119 | 12/2008 |
| WO | WO 86/00529 | 1/1986 |
| WO | WO 86/00811 | 2/1986 |
| WO | WO 89/07946 | 9/1989 |
| WO | WO 90/06131 | 6/1990 |
| WO | WO 93/18790 | 9/1993 |
| WO | WO 96/12808 | 5/1996 |
| WO | WO 97/49826 | 12/1997 |
| WO | WO 99/18799 A1 | 4/1999 |
| WO | WO 99/66045 | 12/1999 |
| WO | WO 00/15853 | 3/2000 |
| WO | WO 00/62735 | 10/2000 |
| WO | WO 00/67786 | 11/2000 |
| WO | WO 00/77218 | 12/2000 |
| WO | WO 02/00169 | 1/2002 |
| WO | WO 02/36617 | 5/2002 |
| WO | WO 03/022202 | 3/2003 |
| WO | WO 04/000209 | 12/2003 |
| WO | WO 2004/043222 | 5/2004 |
| WO | WO 2005/013920 | 2/2005 |
| WO | WO 2005/018580 | 3/2005 |
| WO | WO 2005/051330 | 6/2005 |
| WO | WO 2005/051433 | 6/2005 |
| WO | WO 2005/113013 | 12/2005 |
| WO | WO 2005/113018 | 12/2005 |
| WO | WO 2006/050984 | 5/2006 |
| WO | WO 2007/011601 | 1/2007 |
| WO | WO 2007/025431 | 3/2007 |
| WO | WO 2007/064802 | 6/2007 |
| WO | WO 2008/038845 | 4/2008 |
| WO | WO 2008/065053 | 6/2008 |

OTHER PUBLICATIONS

Apostolidis, Leonidas et al: "Host mediated anti-tumor effect of oncolytic Newcastle Disease Virus after locoregional application"; International Journal of Oncology, vol. 31, No. 5, pp. 1009-1019 (2007).
Csatary, L.K. et al; "MTH-68/H oncolytic viral treatment in human high-grade gliomas"; Journal of Neuro-Oncology, vol. 67, No. 1-2, pp. 83-93 (2004).
Schirrmacher, Volker et al: "Newcastle disease virus: a promising vector for viral therapy, immune therapy, and gene therapy of cancer"; Methods in Molecular Biology, vol. 542, pp. 565-605 (2009).
Yaacov, B. et al: "Selective oncolytic effect of an attenuated Newcastle disease virus (NDV-HUJ) in lung tumors", Cancer Gene Therapy, vol. 15, No. 12, pp. 795-807 (2008).
International Search Report for International Appln. No. PCT/I B 2010/002227 and Written Opinion of International Searching Authority.
Hanson et al, "Identification of Vaccine Strains of Newcastle Disease Virus", Science, vol. 122, pp. 156-157 (1955).
Wheelock, et al, "Observations on the Repeated Administrtion of Viruses to a Patient with Acute Leukemia", New England Journal of Medicine, vol. 271, pp. 645-651 (1964).
Csatary et al, "Interference Between Human Hepatitis a Virus and an Attenuated Apathogenic Avian Virus", Acta Microbiologica Hungarica, vol. 31, Abstract (1983).
Lorence et al, "Newcastle Disease Virus as an Antineoplastic Agent: Induction of Tumor Necrosis Factor-α and Augmentation of its Cytotoxicity", Journal of the National Cancer Institute, vol. 80, pp. 1305-1312 (1988).
Csatary et al, "Treatment of Malignant Tumors with Attenuated Newcastle Disease Virus Vaccine (Strain MTH-68)", Journal of Cancer Research and Clinical Oncology, 116 Supp., Poster Abstract, one page (1990).
Reichard et al, "Newcastle Disease Virus Selectively Kills Human Tumor Cells", Journal of Surgical Research, vol. 52, pp. 448-453 (1992).
Reichard et al, "N-*myc* Oncogen Enhances the Sensitivity of Neuroblastoma to Killing by Newcastle Disease Virus", Pediatric Surgery Forum, vol. 43, pp. 603-606 (1992).

(Continued)

*Primary Examiner* — Bao Li
(74) *Attorney, Agent, or Firm* — Stuart J. Friedman

(57) ABSTRACT

A new clone of Newcastle disease virus which is interferon insensitive and has an ICPI between 1.2 and 2.0 and which may be used in the treatment of cancer and other diseases.

9 Claims, 26 Drawing Sheets

OTHER PUBLICATIONS

Reichard et al, "Retinoic Acid Enhances Killing of Neuroblastoma Cells by Newcastle Disease Virus", Journal of Pediatric Surgery, vol. 28, pp. 1221-1226 (1993).

Csatary et al, "Attenuated Veterinary Virus Vaccine for the Treatment of Cancer", Cancer Detection and Prevention, vol. 17, pp. 619-627 (1993).

Sinkovics et al, "New Developments in the Virus Therapy of Cancer: A Historical Review", Intervirology, vol. 36, pp. 193-214 (1993).

Nelson, "Scientific Interest in newcastle Disease Virus is Reviving", Journal of the National Cancer Institute, vol. 91, pp. 1708-1710 (1999).

Csatary et al, "Use of Newcastle Disease Virus Vaccine (MTH-68/H) in a Patient with High-Grade Glioblastoma", JAMA, vol. 281, pp. 1588-1589 (1999).

Csatary et al, "Beneficial Treatment of Patients with Advanced Cancer Using a Newcastle Disease Virus Vaccine (MTH-68/H)", Anticancer Research, vol. 19, pp. 635-638 (1999).

Csatary et al, "Re: Scientific Interest in Newcastle Disease Virus is Reviving", Journal of The National Cancer Institute, vol. 92, pp. 493-494 (2000).

Krishnamurthy et al, Recovery of a Virulent Strain of Newcastle Disease Virus from Cloned cDNA: Expression of a Foreign Gene Results in Growth Retardation and Attenuation, Virology, vol. 278, pp. 168-182 (2000).

Sinkovics et al, "Newcastle Disease Virus (NDV): Brief History of its Oncolytic Strains", Journal of Clinical Virology, vol. 16, pp. 1-15 (2000).

Fabian et al, "Induction of Apoptosis by a Newcastle Disease Virus Vaccine (MTH-68/H) in PC12 Rat Phaeochromocytoma Cells", Anticancer Research, vol. 21, pp. 125-136 (2001).

Skiadopoulos et al, "Evaluation of the Replication and Immunogenicity of Recombinant Human Parainfluenza Virus Type 3 Vectors Expressing up to Three Foreign Glycoproteins", Virology, vol. 297, pp. 136-152 (2002).

Washburn et al, "Human Tumor Cell Infection by Newcastle Disease Virus leads to Upregulation of HLA and Cell Adhesion Molecules and to Induction of Interferons, Chemokines and finally Apoptosis", International Journal of Oncology, vol. 21, pp. 85-93 (2002).

Engel-Herbert et al, "Characterization of a Recombinant Newcastle Disease Virus Expressing the Green Fluorescent Protein", Journal of Virological Methods, vol. 108, Abstract (2003).

Czeglédi et al, "On the Origins and Relationships of Newcastle Disease Virus Vaccine Strains Hertfordshire and Mukteswar, and Virulent Strain Herts'33", Avian Pathology, vol. 32, pp. 271-276 (2003).

Csatary et al, "MTH-68/H Oncolytic Viral Treatment in Human High-Grae Gliomas", Journal of Neuro-Oncology, vol. 67, pp. 83-93 (2004).

Csatary et al, "Promising MTH-68/H Oncolytic Newcastle Disease Virus Therapy in Human High Grade Gliomas", in "Focus on Brain Cancer Research" (Ed.: Andrew Yang), ISBN: 1059454-973-7, pp. 69-82 (2006).

Wagner et al, "Combined Treatment of Pediatric Hgh-Grade Glioma with the Oncolytic Viral Strain MTH-68/H and Oral Valproic Acid", APMIS, vol. 114, pp. 731-743 (2006).

Fabian et al, "p53-Independent Endoplasmic Reticulum Stress-Mediated Cytotoxicity of a Newcastle Disease Virus strain in Tumor Cell Lines", Journal of Virology, vol. 81, pp. 2817-2830 (2007).

Apostolidis et al, "Host Mediated Anti-Tumor Effect of Oncolytic Newcastle Disease Virus After Locoregional Application", International Journal of Oncology, vol. 31, pp. 1009-1019 (2007).

Jarahian et al, "Activation of Natural Killer Cells by Newcastle Disease Virus Hemagglutinin-Neuraminidase", Jornal of Virology, vol. 83, pp. 8108-8121 (2009).

Engel-Herbert et al, "Characterization of a Recombinant Newcastle Disease Virus Expressing the Green Fluorescent Protein", Journal of Virological Methods, vol. 108, pp. 19-28 (2003).

Csatary et al, "Interference Between Human Hepatitis a Virus and an Attenuated Apathogenic Avian Virus", Acta Microbiologica Hungarica, vol. 31, pp. 153-158 (1983).

* cited by examiner

Fig. 1 The sequence of the F gene

| R | R | Q | R | R | F | I | G | aa sequence |
|---|---|---|---|---|---|---|---|---|
| AGG | AGA | CAG | AGA | CGC | TTT | ATA | GGT | nt sequence |

Fig. 2 The plaques of the MTH-68 H/VB clone (resulting from the test according to Schloer / Hanson)

Fig. 3 Plaques before plaque purification
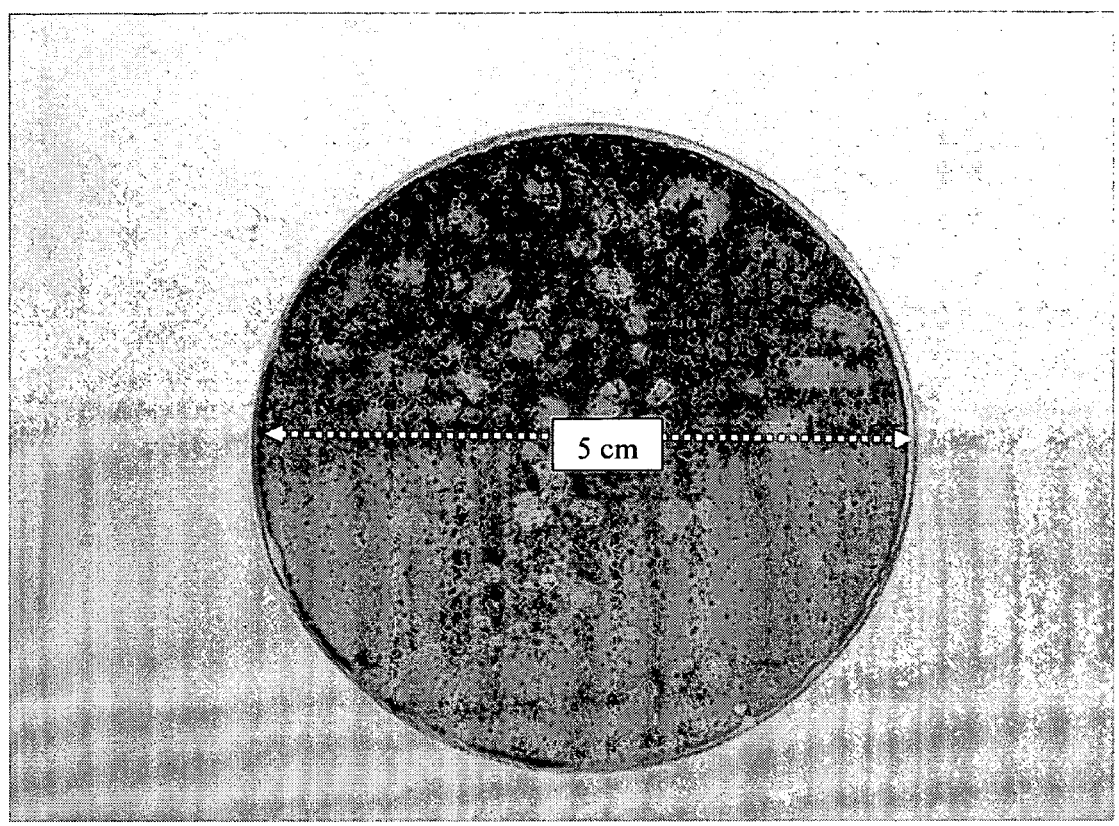

Fig 4    Comparison of virulence and cytopathology of various NDV strains

| Strain | Virulence | Cytophatogenicity in CEF |
|---|---|---|
| LaSota | lentogenic | - |
| Ulster | | ± |
| Queensland | | ± |
| H/W | mesogenic | ± |
| NDV-7 | | ++ |
| Texas GB | velogenic | ++ |
| Herts-33 | | ++ |
| Kansas | | ++ |
| NDV-12 | | + |
| MTH-68H/VB | | ± |

Fig. 5    Interferon induction by NDV strains

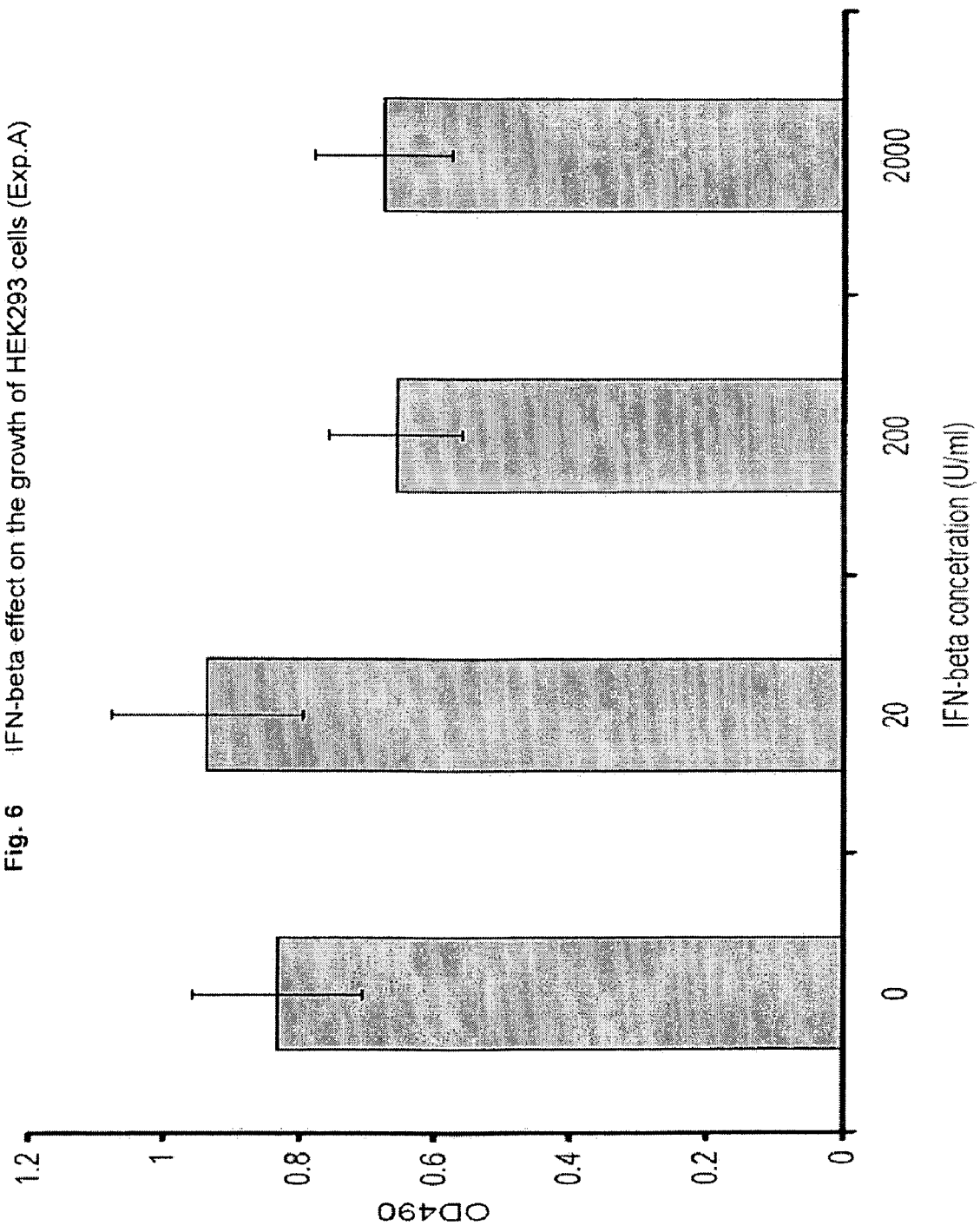

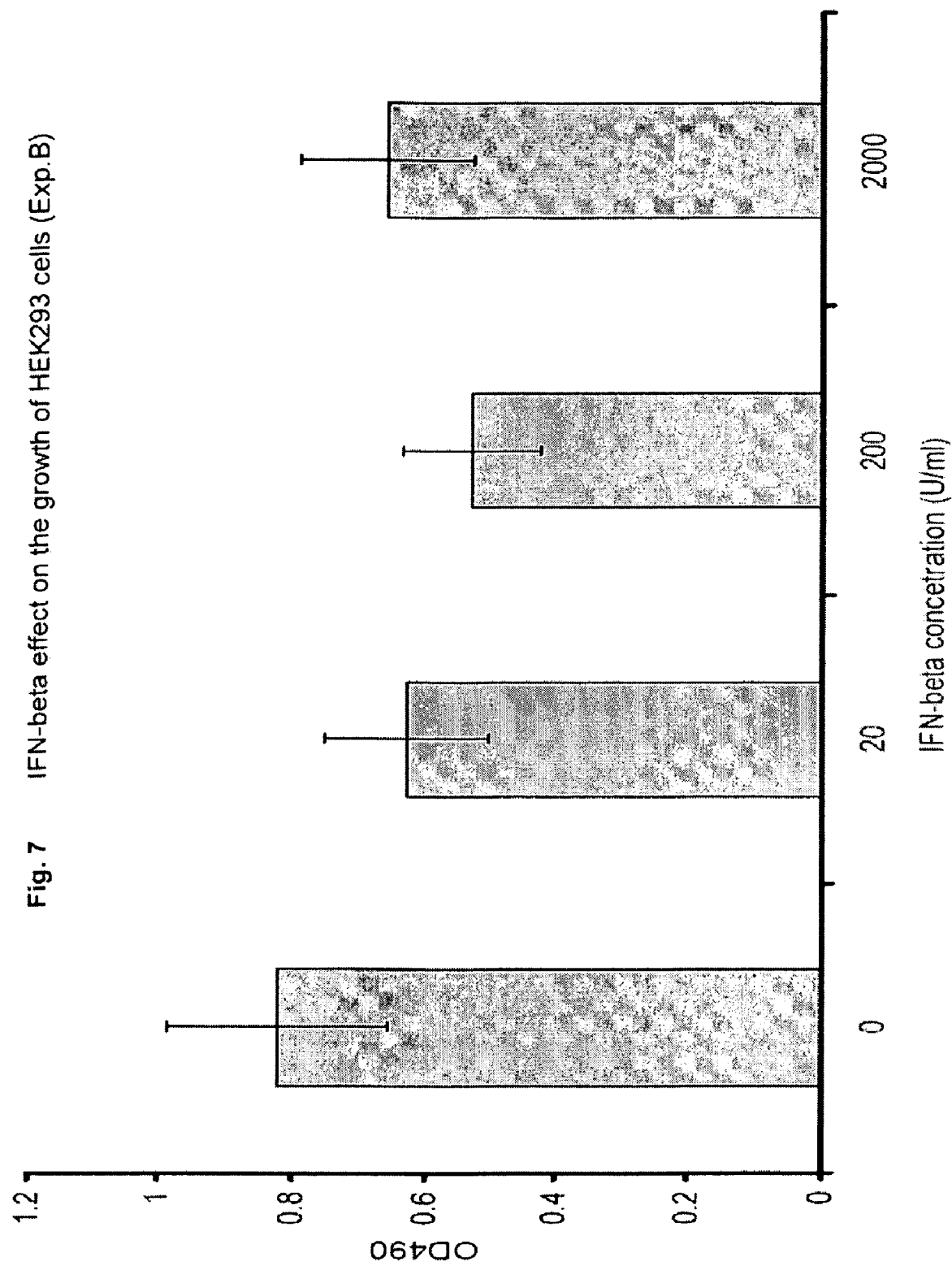
Fig. 7  IFN-beta effect on the growth of HEK293 cells (Exp.B)

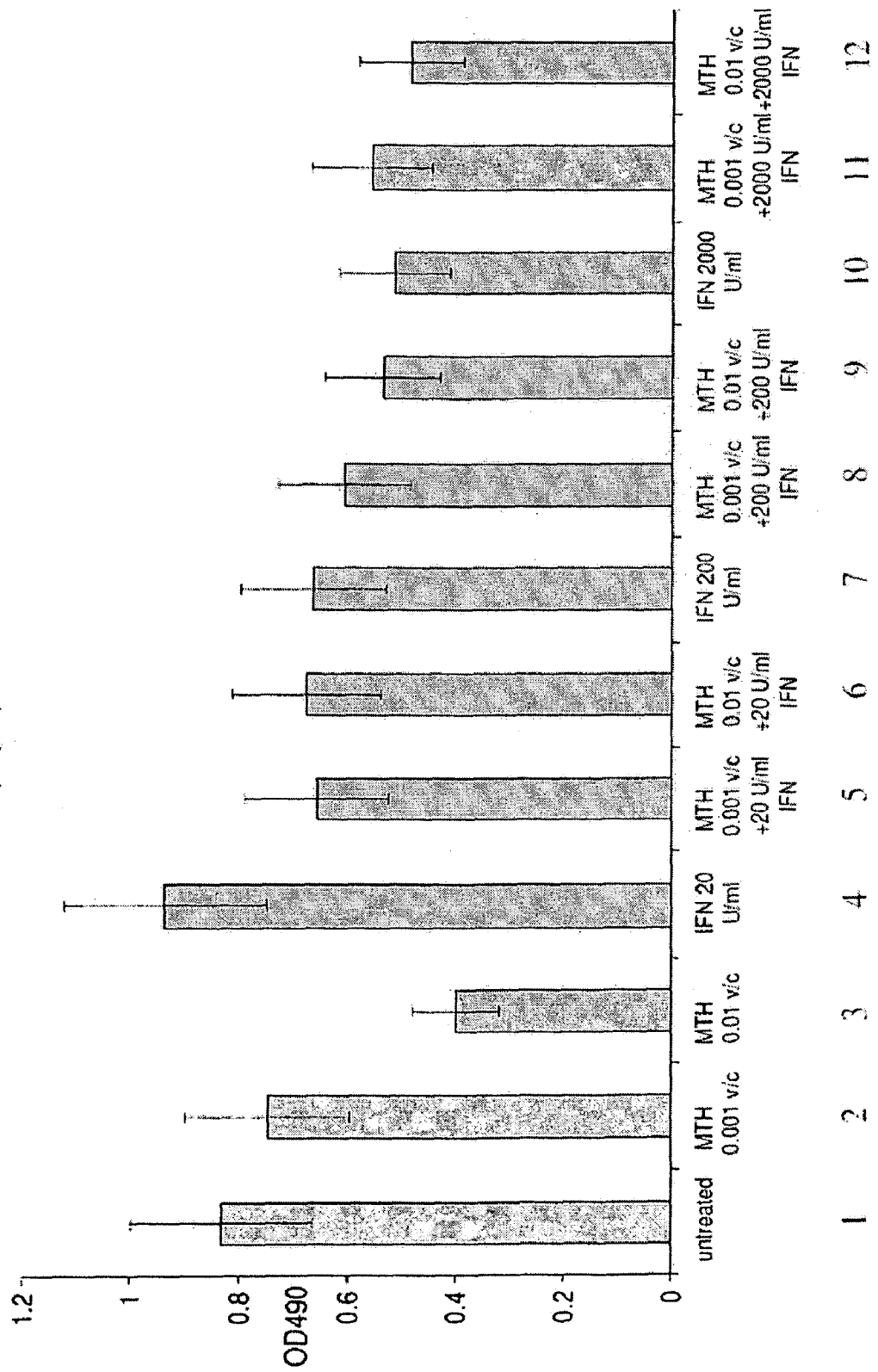
Fig. 8 Effect of interferon-beta on the cytotoxicity of MTH-68H/VB (MTH) in HEK293 cells (Exp.A)

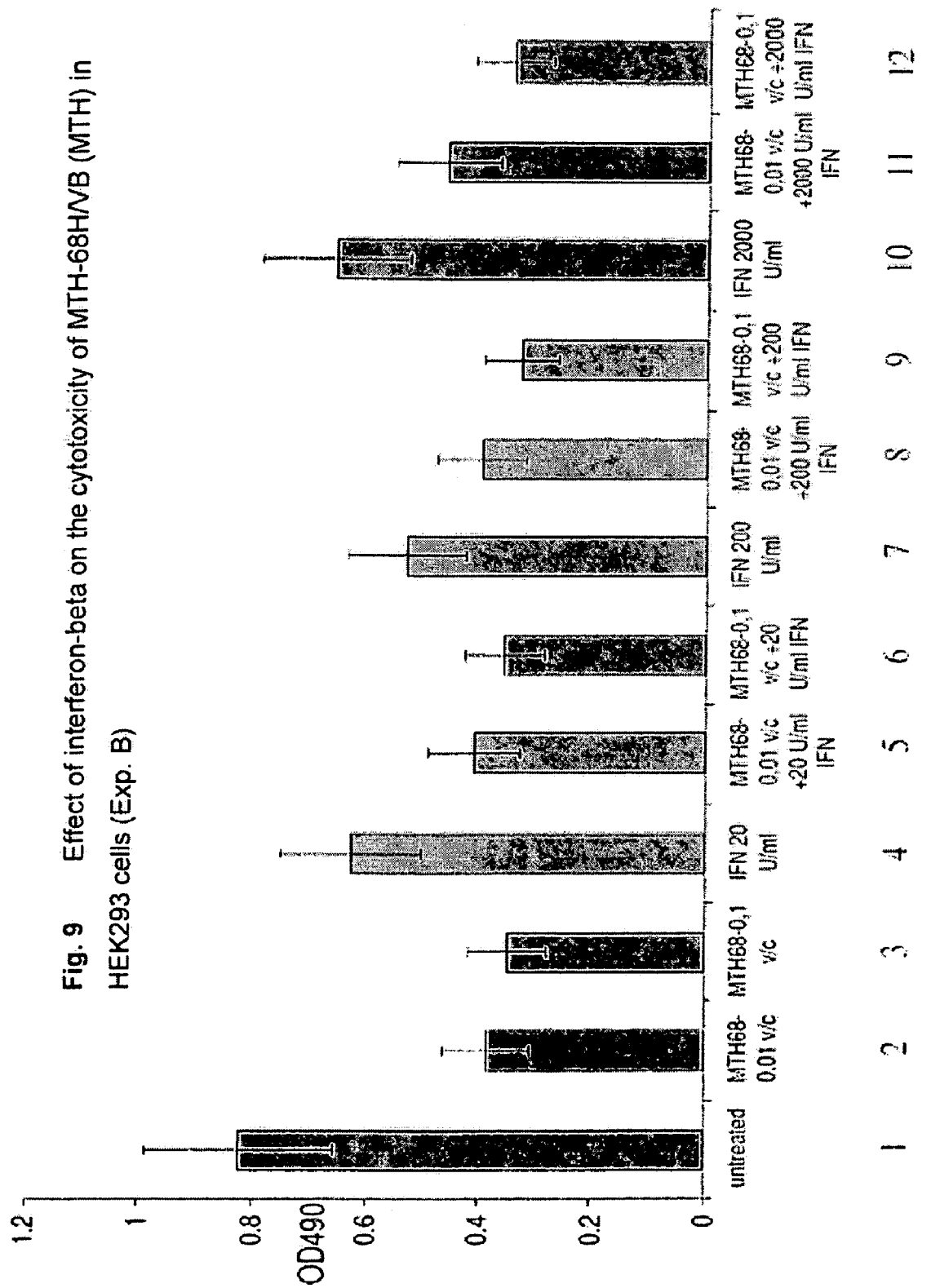
Fig. 9 Effect of interferon-beta on the cytotoxicity of MTH-68H/VB (MTH) in HEK293 cells (Exp. B)

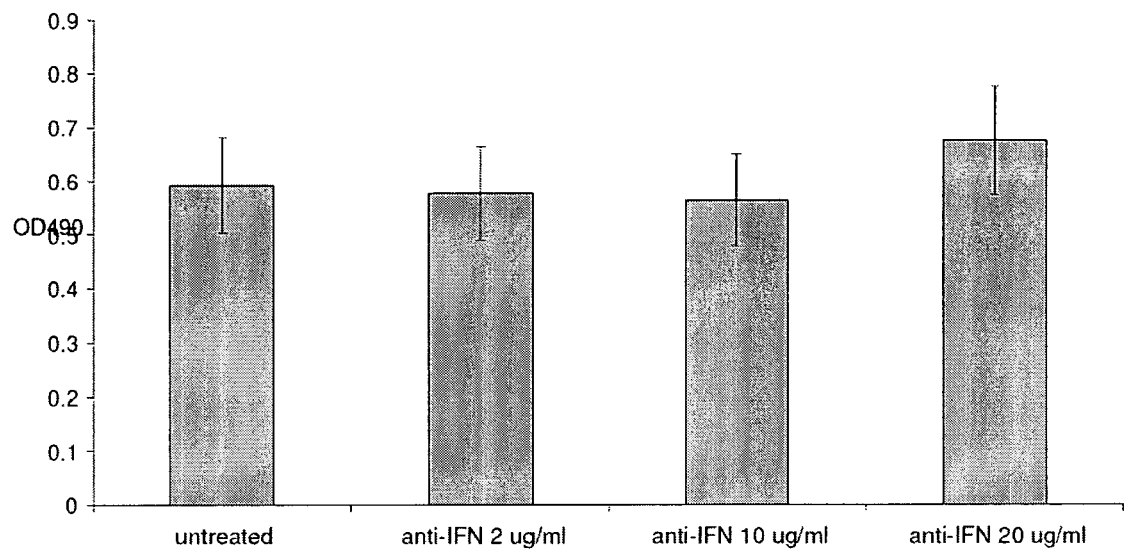
Figure 10. Effect of anti-IFN-beta on the growth of F11 primary human fibroblast cells (Exp. C)
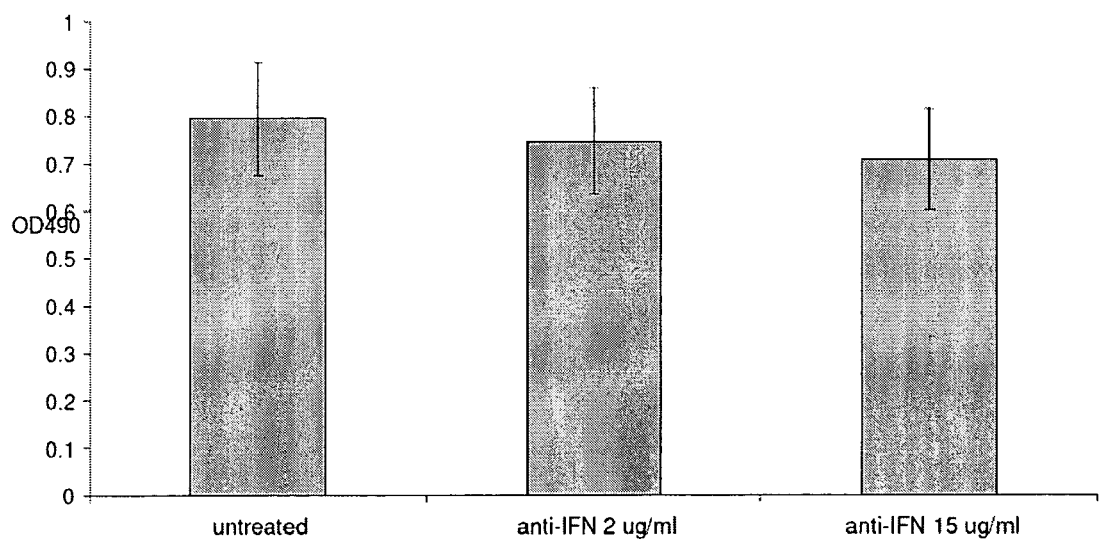
Figure 11. Effect of anti-IFN-beta on the citotoxicity of MTH68 in F11 primary human fibroblasts (Exp. D)

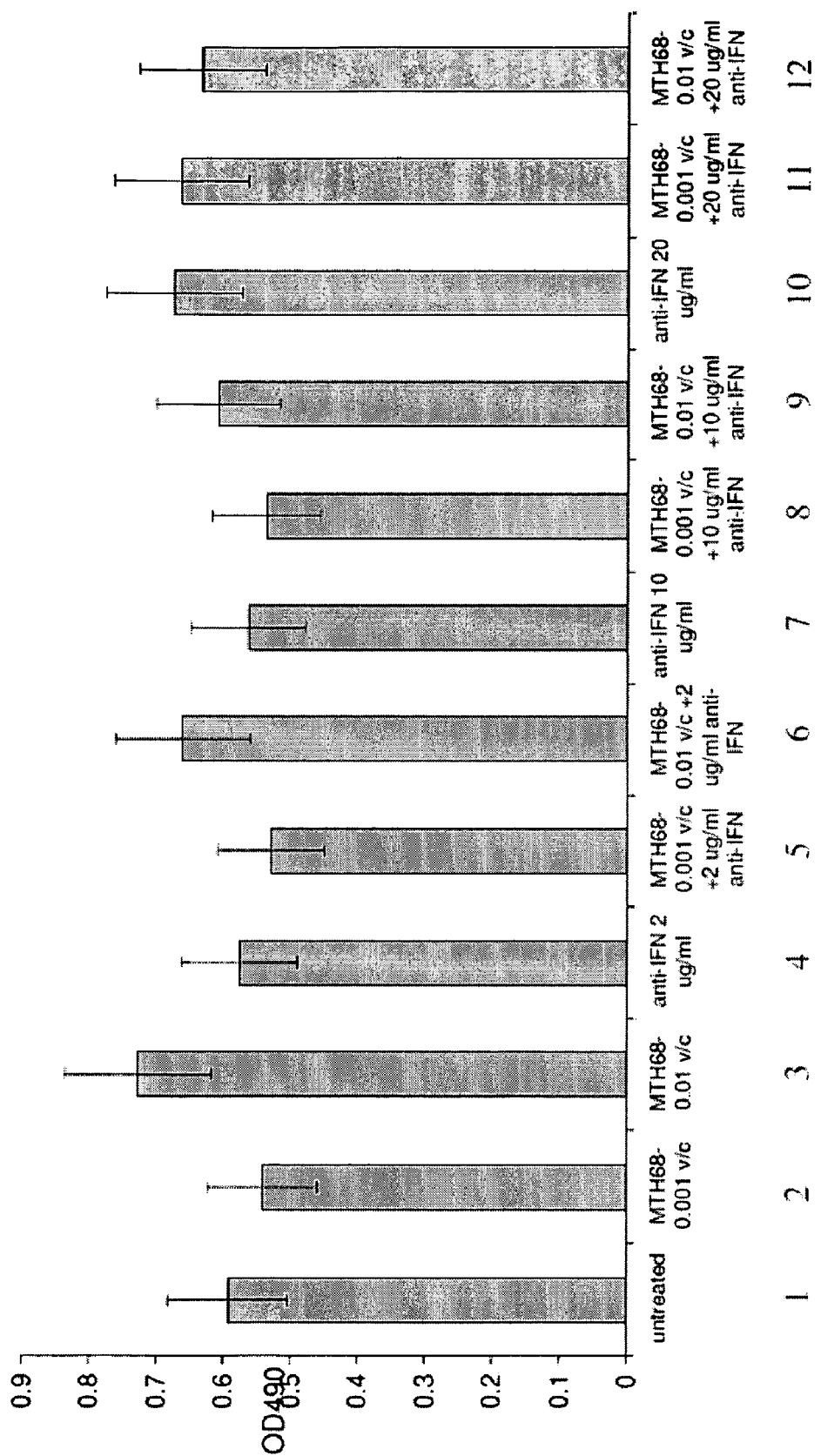
Figure 12. Effect of anti-IFN-beta on the citotoxicity of MTH68 in F11 primary human fibroblasts (Exp. C)

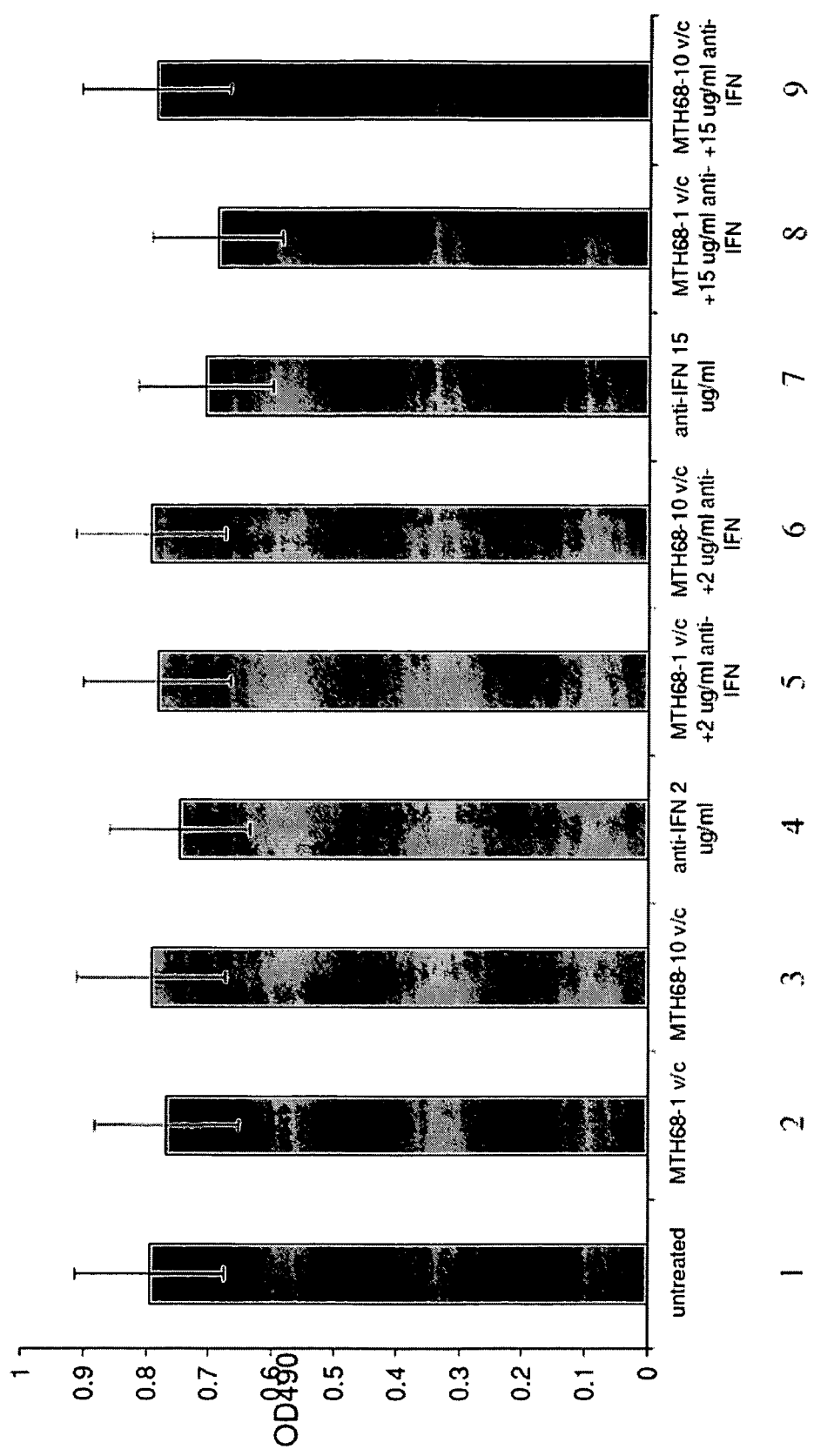

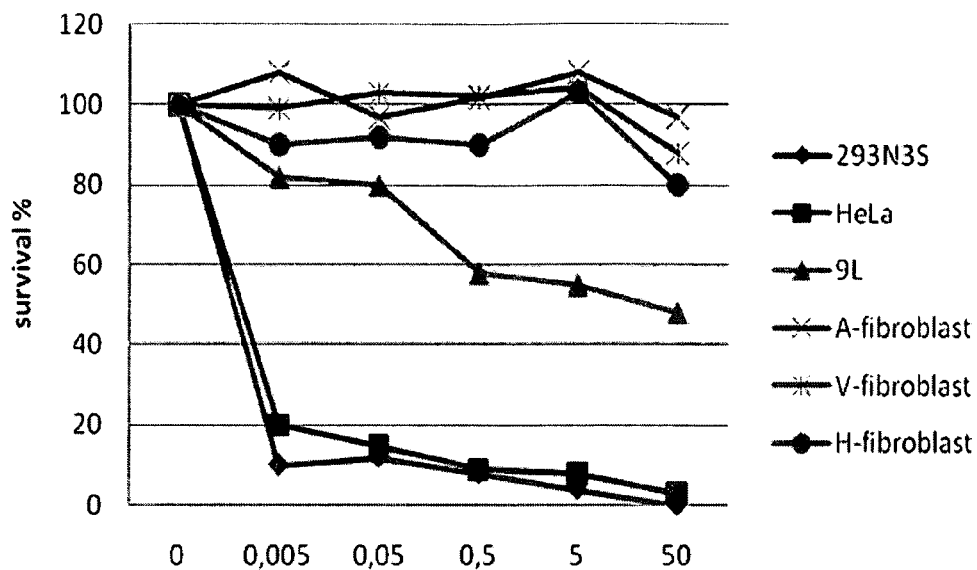
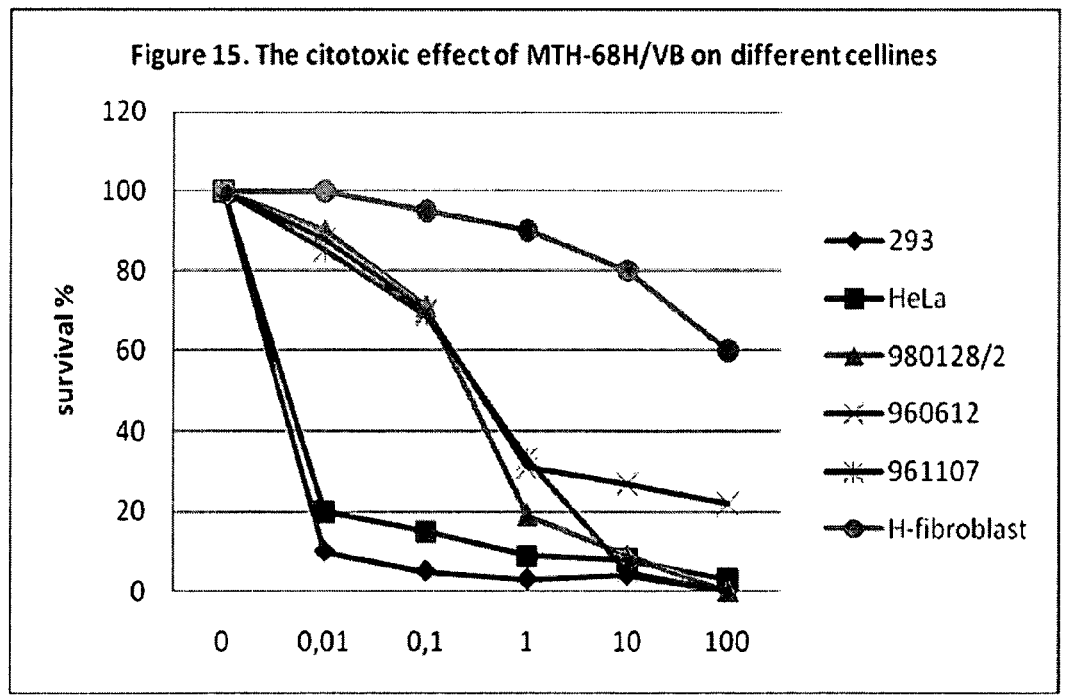
Fig. 15

Fig. 16

Figure 16 Citotoxic effect of different NDV srains (H-fibroblast cell line)

- MTH-68H/VB
- H/W strain
- Mukteswar
- LaSota(V1)46
- VP

Fig. 17

Figure 17. Citotoxic effect of different NDV srains (HeLa cell line)

- MTH-68H/VB
- H/W strain
- Mukteswar
- LaSota(V1)46
- VP

Figure 19.    The cytotoxic effect of MTH-68H/VB on BC-1, HT-3 and 293 cells

Figure 20. The effect of MTH-68H/VB on DAOY, SK-N-FI and IMR-32 cells

Figure 21. The effect of MTH-68H/VB on OVCAR cells

Figure 22. The effect of MTH-68/VB on C-41 cells

Fig. 23  Effect of MTH-68H/VB treatment on the growth of subcutaneous GI261 tumors (weekly treatment)
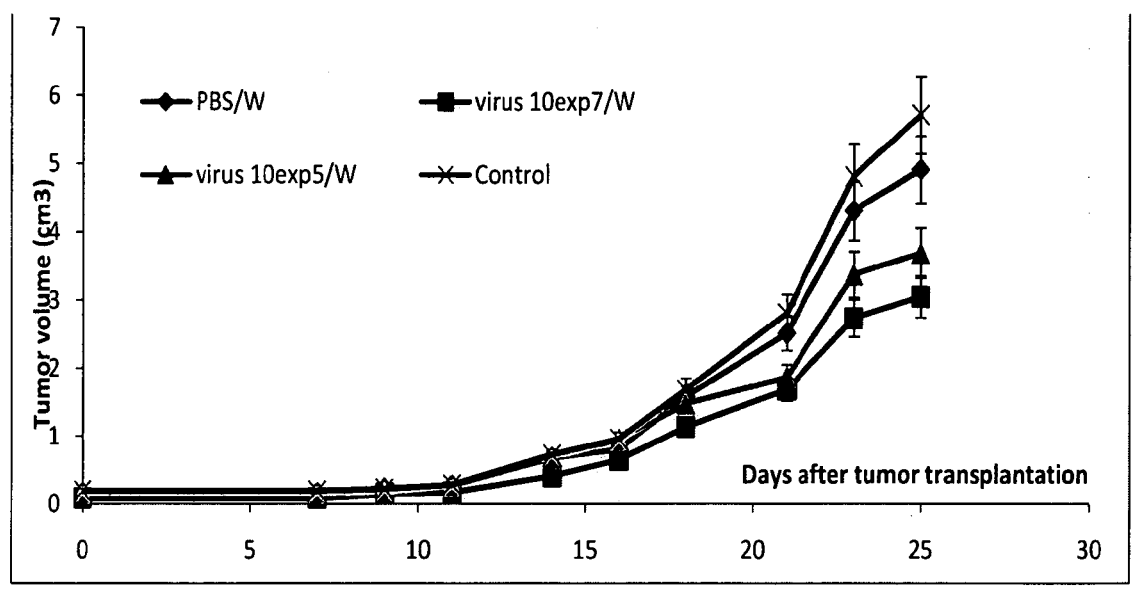

Fig. 24  Effect of MTH-68H/VB treatment on the growth of subcutaneous GI261 tumors (daily treatment)
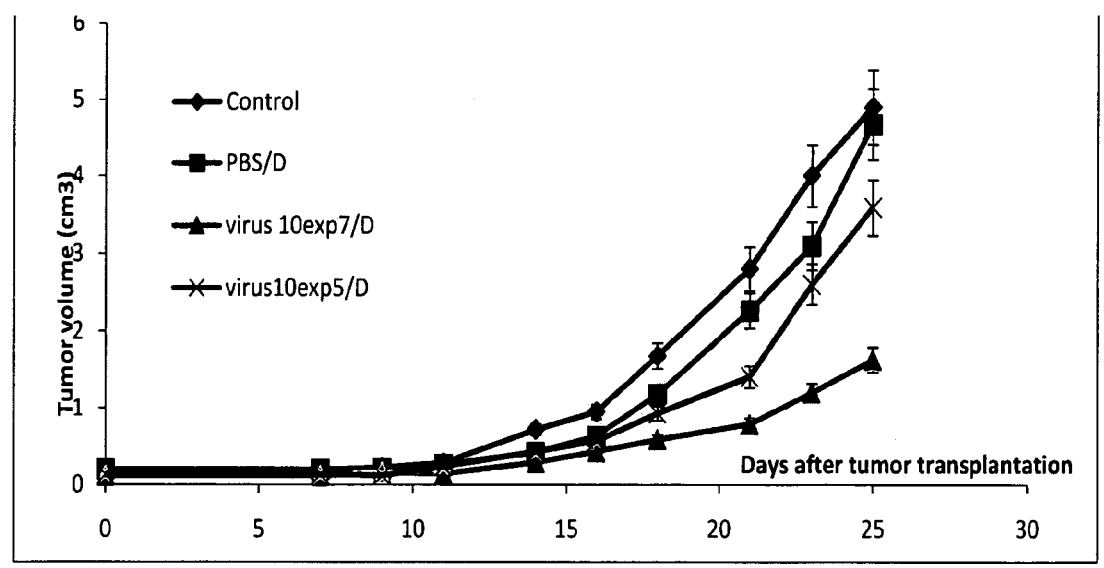

Fig. 25    Combined effect of MTH-68H/VB treatment and tumor irradiation on the growth of subcutaneous Gl261 tumors
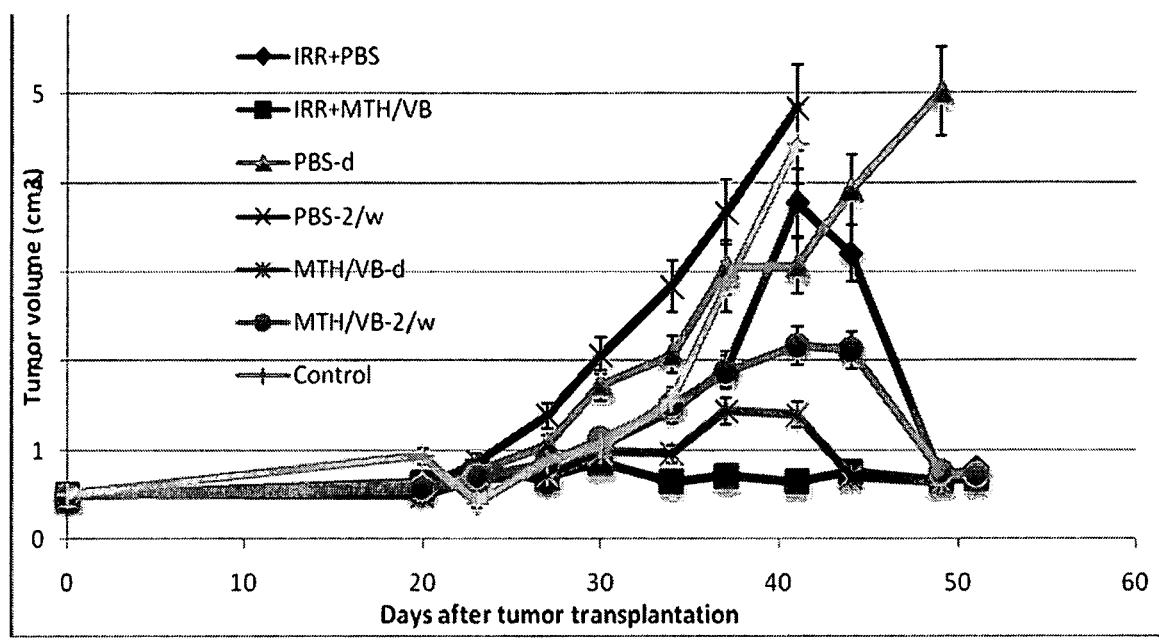

Fig. 26  Survival of tumor bearing mice after combined treatment with MTH-68H/VB and irradiation
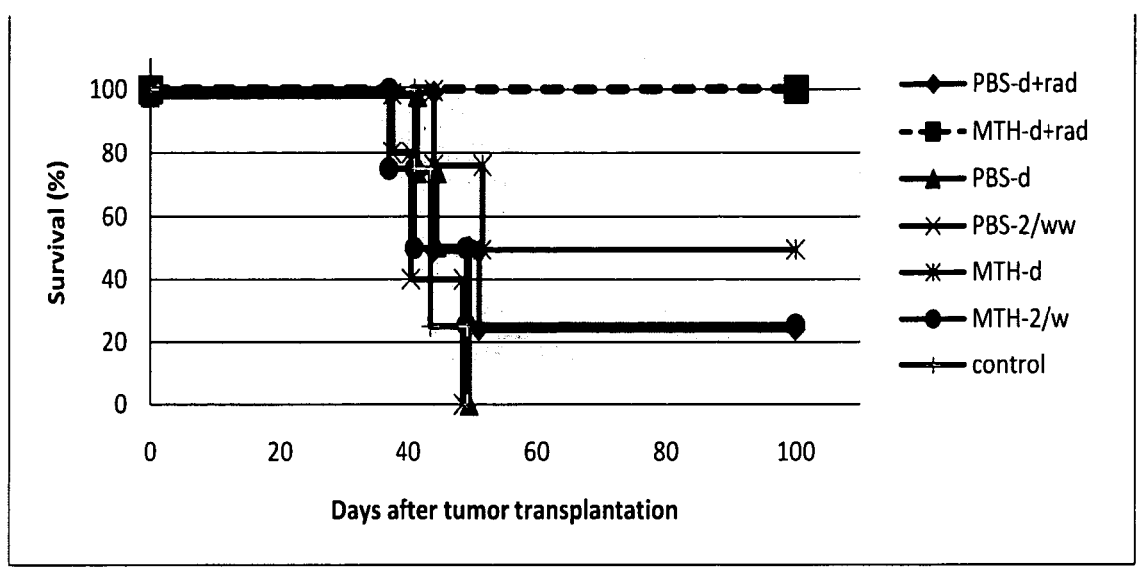

Fig. 27 Tumor growth rate after combined treatment with irradiation, temozolomide and MTH-68H/VB – experiment 1
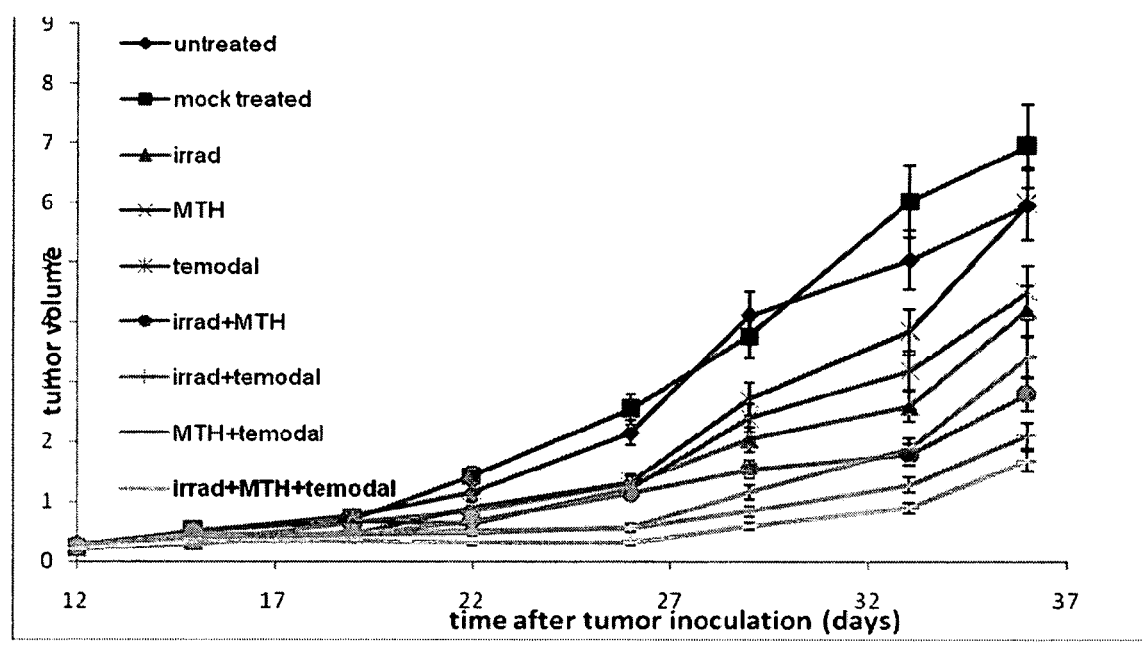

Fig. 28  Tumor growth rate after combined treatment with irradiation, temozolomide and MTH-68H/VB – experiment 2
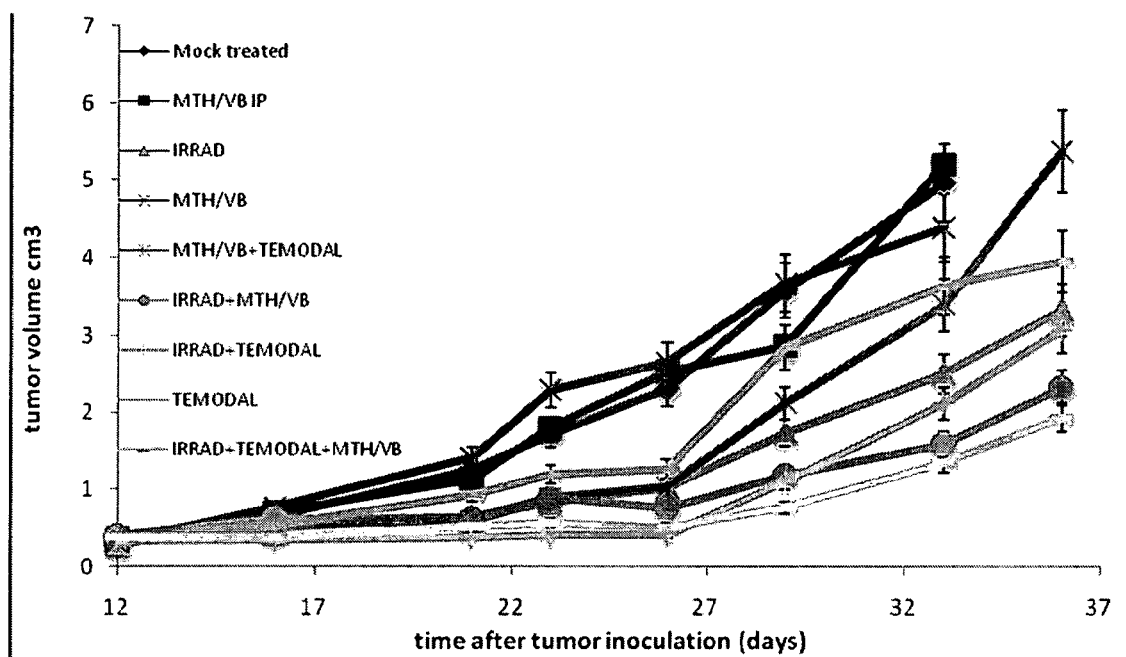

Fig. 29   The effect of MTH-68H/VB, irradiation and BCNU treatment on the tumor size in tumor bearing mice
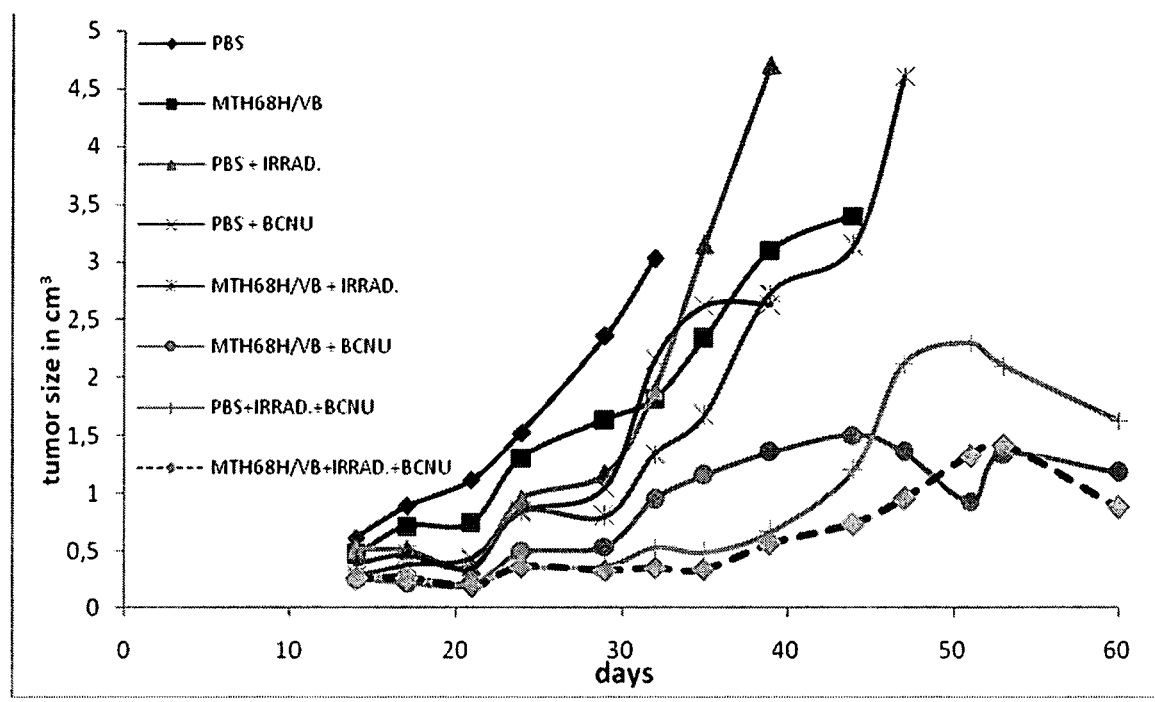

Fig. 30    The survival of tumor bearing mice (%)
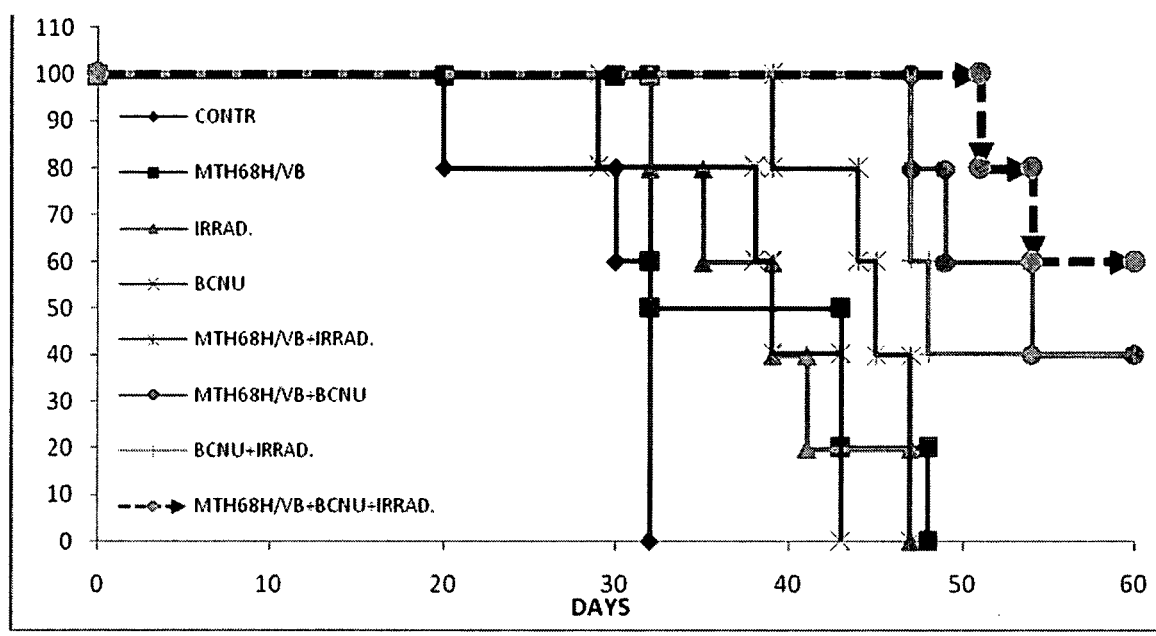

Fig. 31 family tree of known NDV virus strains

- 2%
- IT-63/73
- NY parrot/70
- Essex 70
- US(Ca)-1085/71
- HU-10/72
- BG-88/73 } V
- Herts/33/P
- Italien/45
- DE-1/39
- IT-66/76
- BG-60/81
- Herts/33/NS
- Herts/33 } ear
- IT-48/68
- IT-85/81
- IT-7/60
- BG-20/75
- HU-5/70
- BG-92/77
- SIMF 64 (RU)
- BG-1/59
- BG-44/82 } IV
- TW-3/95
- TW/69
- KR-1/65
- AUS Victoria/32
- Miyadera/51
- *TB-Mukteswar*
- *Muktesvak*
- Mukteswar/IN
- MTH-68H/VB
- H/W } III
- Ulster 2C/67
- V4 (Queensland)/66 } I
- TCND*
- US (Ca)-11914/46*
- B-1 (Iv)/48
- La Sota (VI)/46
- TexasGB/48
- Beaudette C } II

Fig. 32

| Gene | Start | End | Intergenic region | coding region | complete gene | Aa. |
|---|---|---|---|---|---|---|
| NP | UGCCCAUCUU | AAUCU$_7$ | A | 122-1591 | 56-1803 | 489 |
| P | UGCCUGUGUU | AAUUCU$_6$ | A | 1888-3075 | 1805-3254 | 395 |
| V | | | | 1888-2607 | | 239 |
| W | | | | 1888-2571 | | 227 |
| M | UGCCCAUCUU | AAUCU$_6$ | G | 3290-4384 | 3256-4496 | 364 |
| F | UGCCCAUCUU | AAUUCU$_6$ | GAUGGCCUACACAUCCUC UUGUUUUCCCUUAUA | 4544-6205 | 4498-6289 | 553 |
| HN | UGCCCAUCUU | AAUUCU$_6$ | ACACCUGCCACCACUUUAUGUUCC GUUUUGUCGAGUGUCUGGUGUCG | 6412-8127 | 6321-8322 | 571 |
| L | UGCCCAUCUU | AAUCU$_7$ | | 8381-14995 | 8370-15073 | 2204 |

CLONE OF NEWCASTLE DISEASE VIRUS, ITS MANUFACTURE AND ITS APPLICATION IN THE MEDICAL TREATMENT OF CANCER

CROSS-REFERENCE TO RELATED APPLICATIONS

This is a non-provisional patent application based upon U.S. provisional application Ser. No. 61/283,154 filed Nov. 30, 2009.

BACKGROUND OF THE INVENTION

The information in the ASCII text file named 740481-54MTH68HVBseqlisting.txt, created Sep. 14, 2012 and having a size of 26,438 bytes is hereby incorporated by reference.

Newcastle Disease Virus (NDV) is a virus well known in the art [Diseases of poultry, 10th edition, edited by B. W. Calnek, Mosby International, Iowa State University Press, Ames, Iowa, 1997]. The virus is responsible for great economic losses in the poultry industry. It is also well known that many strains of NDV exist (EP 0770397 B1) with an enormous range in the severity and type of disease produced in poultry. Newcastle disease virus (NDV) is classified as an avian paramyxovirus-1 (APMV1), a member of the family Paramyxoviridae in the order Mononegavirales. Members of this family have a single stranded, linear, RNA, with an elliptical symmetry. The total genome is roughly 16,000 nucleotides. Replication of the virus takes place in the cytoplasm of the host cell.

This family is divided into two subfamilies, the Paramyxovirinae and the Pneumovirinae. During 1993, the International Committee on the Taxonomy of Viruses rearranged the paramyxoviruses and placed NDV within the Rubulavirus genus. The genomes of most rubulaviruses, except NDV, contain a small hydrophobic (SH) protein gene that is not present among other paramyxoviruses. Based on predicted amino acid sequences for each viral protein, NDV clones phylogenetically group as a clade separate from the rubulaviruses. The polycistronic phosphoprotein (P) gene editing sequence of NDV and putative gene products are more similar to expression patterns among members of the Respirovirus and Morbillivirus. In addition, structure of the nucleocapsid protein more closely resembles the Respiroviruses. There are nine recognized serotypes among avian paramyxoviruses that infect primarily only bird species. These virus types are phylogenetically distinct from NDV, but separate as a clade with NDV from the other paramyxoviruses. This relationship was further confirmed by phylogenetic analysis of full-length genomic sequences.

As with the situation for many other avian viruses, NDV has evolved among birds separate from their mammalian counterparts. Consequently, based on several key factors, including gene and predicted amino acid sequences, avian paramyxoviruses deserve their own genus designation among the Paramyxovirinae.

Newcastle disease (ND) is a contagious viral disease affecting only species of birds. Clinical signs are extremely variable depending on the strain of virus, species and age of bird, concurrent disease, and pre-existing immunity.

Vaccination plays a pivotal role in the control of Newcastle disease (ND) in poultry. This can partly be attributed to the fact that several naturally derived less pathogenic and attenuated live viral strains were identified and have been available for this purpose as early as the second half of the 1940's (reviewed by Lancaster, 1964).

The extreme variation in virulence of different ND virus clones and the widespread use of live vaccines means that the identification of an clone as ND virus from birds showing clinical signs does not confirm a diagnosis of ND, so that an assessment of the virulence of the clone is also required.

NDV strains have been classified in several ways by several authors and institutions. An early form of classification was based on their pathogenicity, in which the strains were classified into velogenic, mesogenic, lentogenic and avirulent groups (Hanson and Brandly, 1955).

Several potential in-vitro tests for establishing virulence usually related to the molecular basis for pathogenicity are being investigated by various groups around the world. At present, a definitive assessment of virus virulence is usually based on one or more of the following in-vivo tests, although the current OIE definition allows molecular assessment of virulence.

1. The plaque size and the virulence relationship of the NDV strains was published by G. M. Schloer and R. P. Hanson (J. Virol. 1968 January; 2(1): 40-47.). Schloer and Hanson found that the size of the plaques of the NDV was related to virulence for chickens. Markedly larger plaques were produced by the velogenic (high virulence) strains while smaller plaques were found in mesogenic (intermediate virulence) strains. This method was used in the past as a way to classify NDV strains by measurement of plaque size.

2. Mean death time in eggs The MDT has been used to classify ND virus strains into velogenic (taking under 60 hours to kill); mesogenic (taking between 60 and 90 hours to kill); and lentogenic (taking more than 90 hours to kill).

3. Intracerebral pathogenicity index (ICPI). The most virulent viruses will give indices that approach the maximum score of 2.0, whereas lentogenic strains will give values close to 0.0. The mesogenic strains fall between 0.7 and 1.5.

4. Intravenous pathogenicity index (IVPI). Lentogenic strains and some mesogenic strains will have IVPI values of 0, whereas the indices for virulent strains will approach 3.0.

5. Molecular basis for pathogenicity. During replication, ND virus particles are produced with a precursor glycoprotein, F0, which has to be cleaved to F1 and F2 for the virus particles to be infectious. This post-translation cleavage is mediated by host-cell proteases. Trypsin is capable of cleaving F0 for all ND virus strains. It would appear that the F0 molecules of viruses virulent for chickens can be cleaved by a host protease or proteases found in a wide range of cells and tissues thus spreading throughout the host, damaging vital organs, but F0 molecules in viruses of low virulence are restricted in their sensitivity to host proteases resulting in restriction of these viruses to growth only in certain host-cell types. Most ND viruses that are pathogenic for chickens have the sequence $^{112}$R/K-R-Q-K/R-R$^{116}$ of SEQ ID NO: 4 at the C-terminus of the F2 protein and F (phenylalanine) at residue 117, the N-terminus of the F1 protein, whereas the viruses of low virulence have sequences in the same region of $^{112}$G/E-K/R-Q-G/E-R$^{116}$ of SEQ ID NO: 5 and L (leucine) at residue 117. It appears to be the requirement of at least one pair of basic amino acids at residues 116 and 115 plus a phenylalanine at residue 117 and a basic amino acid (R) at 113 if the virus is to show virulence for chickens. Based on these molecular findings the veterinary classification of ND viruses is no longer divided into three—but rather into two divisions—pathogenic and apathogenic.

It seems likely that the vast majority of birds are susceptible to infection with ND viruses of both high and low virulence for chickens, although the clinical signs seen in birds infected with ND virus vary widely and are dependent on factors such as: the virus, host species, age of host, infection with other organisms, environmental stress and immune status. In some circumstances infection with the extremely virulent viruses may result in sudden high mortality with comparatively few clinical signs. Thus the clinical signs are variable and influenced by other factors so that none can be regarded as pathognomonic.

Newcastle disease is defined as an infection of birds caused by a virus of avian paramyxovirus serotype 1 (APMV-1) that meets one of the following criteria for virulence:

A) The virus has an intracerebral pathogenicity index (ICPI) in day-old chicks (*Gallus gallus*) of 0.7 or greater B) Multiple basic amino acids have been demonstrated in the virus (either directly or by deduction) at the C-terminus of the F2 protein and phenylalanine at residue 117, which is the N-terminus of the F1 protein. The term 'multiple basic amino acids' refers to at least three arginine or lysine residues between residues 113 and 116. Failure to demonstrate the characteristic pattern of amino acid residues as described above would require characterization of the cloned virus by an ICPI test. In this definition, amino acid residues are numbered from the N-terminus of the amino acid sequence deduced from the nucleotide sequence of the F0 gene, 113-116 corresponds to residues −4 to −1 from the cleavage site.'

Genetic analyses of NDV strains cloned in the past 80 years have revealed the existence of at least 9 genotypes (and further subtypes) that showed not only region specific and host species associations but their temporal distribution was also apparent (Lomniczi és Czeglédi, 2005). It was shown that early genotypes [II.-IV. and Herts'33(W)] prevalent before the 1960s were replaced by recent genetic groups (V.-VIII.) following the introduction of vaccination. Recently sublineages of the Far East genotype VII have spread to other geographic areas, e.g. to Europe (see family tree of known NDV virus strains (FIG. 31)). Replacement of genotypes appears to be an evolutionary process rather than random epidemiological event in the distribution of NDV strains. The emergence of novel virulent genotypes seems to be inconsistent with the application of vaccination but experimental infections shed light on the process whereby immunized chicken population became the reservoir of the novel virulent viruses.

As to the ecology two major reservoirs of NDV strains exist in nature. The primordial reservoir consists of wild water-bird species that harbor primitive (apathogenic) viruses but, surprisingly, only two genetic lineages are known in the wild: class I and genotype I (belonging to class II). By contrast, the remainder (genotypes II.-VIII). comprises virulent strains and is maintained in the secondary (artificial) reservoirs of chickens. It is hypothesized that the chicken populations were seeded with apathogenic viruses and pathogenic strains emerged in the chicken host. Prior to the immunization period at least two independent colonizations could have taken place (with genotype I and II).

Genetic analysis of an authentic sample of the first European clone, Herts'33 (cloned in England in 1933), revealed that it represented a highly diverged novel early lineage. Contrarily to a 1940 publication from England in which the derivation of strain H, one of the most successful early vaccines, from Herts'33(W) by egg passage was reported, genetic analysis precluded relationships between them.

Genetic analyses of NDV strains have also indicated a remarkable genetic stability of NDV strains, even after prolonged and repeated passage. The genetic stability is proven by the lack of viral recombination in nature. Toyoda et al. analyzed the sequences of the NH and F genes of multiple strains of NDV cloned over a period of 50 years. There was no gene exchange by recombination in the generation of three lineages. (Toyoda T., Newcastle disease virus evolution. II. Lack of gene recombination in generating virulent and avirulent strains. Virology 169: 273-282, 1989.)

NDV is usually thought to be an avian virus, but it also able to infects humans. Although NDV causes a potentially fatal, noncancerous disease (Newcastle disease) in birds, it causes only minor illness, manifested in mild flu like symptoms, or conjunctivitis in exposed humans (historically chiefly observed in laboratory workers).

In 1971 a scientific publication in "The Lancet" by Dr. Laszlo Csatáry described case histories of cancer treatment with an undisclosed strain of Newcastle Disease Virus (The Lancet, 1971, 7728, p. 825). Subsequently to this publication Dr. L. Csatáry and co-workers have published a number of scientific publications as well as patent applications (see below) based on scientific work with a virus strain referred to as "MTH-68/H". However, none of these references disclose the exact nature of the virus strain, the virus strain has never been commercially available nor been deposited at any virus library and therefore all these publications are not enabling for an expert skilled in the art. Moreover, further scientific work exists with virus compositions referred to as "MTH-68/H" from scientists other than Dr. L. Csatáry. However, it is highly unclear whether the virus compositions used are identical to that having been described in the Lancet publication cited above.

The work of Dr. Csatáry has obviously stimulated the medical community so that further work has been published such as EP 696326 B1 (Wellstat Biologics Corporation) and others as listed below. However, the scientific work disclosed therein cannot be reproduced by an expert in the art as the strains used therein such as strain 73-T or MK-107 are likewise not available to the public.

Significant interest has developed in the potential for use of NDV in cancer therapy because NDV has been found to have selective cell killing properties in many types of cancer cells while not effecting normal non-neoplastic cells. A report indicating that NDV might be useful as a cancer treatment was published in the early 1960s. Since then, a number of studies have been reported.

Many NDV strains have been found to be cytotoxic to cancer cells. Some strains are able to replicate in and destroy cancer cells while at the same time not effecting normal cells. These strains have been termed oncolytic. Different strains demonstrate different levels of cancer cell damaging properties, and different cancer cell types show sensitivity to different strain types of NDV. These properties define a strain's oncolytic potency. The oncolytic potency is thought to have a clinical correlation as to the therapeutic dosaging requirements. In experimental conditions the more oncolytically potent the strain is for a cancer cell type the lower the multiples of infective (MOI) viral particles per cell is needed to be able to observe a cytolytic effect. The clinical implication is a need for lower viral doses to achieve a therapeutic effect. While NDV has not been observed to cause any significant disease in humans—at extremely high therapeutic doses given parentally, as has been used in some clinical trials—it has been noted to potentially cause side effects of hypotension and high fever—leading to the need to find alternative techniques of dosaging—to desensitize the patient prior to giving the high dose application (see WO 00/62735).

SUMMARY OF THE INVENTION

It is therefore an object of the invention to provide a new clone of NDV which is oncolytic and has improved properties compared to existing strains.

An expert skilled in the art reading this document will easily identify the following additional objects of the invention which are summarized in this section for the reader's convenience. However, the following list does not exclude further objects that may be contained in the description.
1) A Newcastle Disease Virus clone which is
    interferon insensitive and has an ICPI between 1.2 and 2.0.
2) A Newcastle Disease Virus clone according to object 1 which is
    interferon insensitive and has an ICPI between 1.2 and 1.5.
3) A Newcastle Disease Virus clone according to object 1 comprising the DNA nucleotide sequence of SEQ ID NO: 1.
4) A Newcastle Disease Virus clone according to object 1 as deposited with European Collection of Cell Cultures as Accession Number 06112101 on Nov. 21, 2006.
5) The use of a Newcastle Disease Virus clone according to at least one of objects 1-4 for the manufacture of a medicament for the treatment of cancer by causing tumor cell death
    or for a preventative form of biological cancer therapy, destroying nascent or residual cancer cells or decreasing the risk of development of metastatic lesions.
6) A use according to object 5, wherein the human tumor cells are p53-negative human tumor cells.
7) A use according to object 5, wherein the human tumor cells are selected from cervical cancer, ovarian cancer, bladder cancer, renal carcinoma, Wilm's tumor, prostate cancer, lung cancer (including bronchial), lymphoma, leukemia, central nervous system tumors (including meningeoma, medulloblastoma, glioblastoma, astrocytoma, neuroblastoma); pancreatic cancer, skin cancer (incl. melanoma), colon cancer, bone (both primary and metastic lesions) and breast cancer, stomach cancer, esophageal cancer, thyroid cancer, sarcomas, mesothelioma, head and neck cancers (including oro-naso-pharyngeal, parathyroid), hematological malignancies, vulvar, vaginal, endometrial carcinomas, testicular carcinoma, ano-rectal cancers, hepatic and extrahepatic (bile duct) cancers, sarcomas (including Ewings), eye cancer (including retinoblastoma), thymic carcinoma, urethral cancers, carcinoid tumors or adrenocortical cancers.
8) A use according to object 5, wherein the administration is provided by way of intravenous, intra-arterial, enteral, parenteral, intrathecal, intraperitoneal, intrathoracic, intrapleural, oral, sublingual, bucco-mucosal, intranasal, intracystic, intraurethral, rectal, vaginal, subcutaneous, intratumoral, peritumoral, local, intramuscular, intrabronchial, intrarterial, intracranial, and/or topical application.
9) A use according to object 5, wherein a single dose received by a patient contains $1\times10^5$ to $1\times10^{12}$ virus particles, preferably $1\times10^6$ to $1\times10^{10}$ virus particles, most preferably $1\times10^7$ to $1\times10^9$ virus particles.
10) A use according to object 5, wherein a patient receives one or more multiples of $1\times10^5$ to $1\times10^{12}$ virus particles, preferably one or more multiples of $1\times10^6$ to $1\times10^{10}$ virus particles, most preferably one or more multiples of $1\times10^7$ to $1\times10^9$ virus particles frequently between three times a day to once per month.
11) A use according to object 5 in which virus treatment is combined with chemotherapy, radiotherapy (such as α, β or γ-radiation, X-ray-radiation, particle-radiation), immunotherapy or surgery.
12) A use according to object 11 in which virus treatment is applied before, together, or after application of chemotherapy, radiotherapy (such as α, β or γ-radiation, X-ray-radiation, particle-radiation), immunotherapy or surgery.
13) The use of a Newcastle Disease Virus clone according to at least one of objects 1-4 for the manufacture of a medicament for the treatment of interferon sensitive neoplastic conditions, especially from Melanoma, (non-Hodgkins) Lymphomas, Leukemias (Chronic Myeloid Leukemia, Hairy Cell Leukemia), Breast cancer, Bladder Carcinoma, Renal cell carcinoma, Head and Neck cancer, Carcinoid tumors, Bile Duct cancers, Pancreatic cancer, Multiple Myeloma, Kaposi Sarcoma, as well as non-neoplastic interferon sensitive autoimmune and viral conditions such as Multiple sclerosis, Condylomata acuminata, Hepatitis, Herpes, Rheumatic Arthritis, Behcet's Disease, Idiopathic Pulmonary Disease, Aphthous stomatitis, Severe Malignant Osteoporosis, cervix cancer, or SARS.
14) A method to reduce pain perception in a cancer patient comprising application of Newcastle Disease virus to said cancer patient.
15) A method to reduce pain perception in a cancer patient according to object 14 comprising application of Newcastle Disease virus clone according to at least one of object 1-4 to said cancer patient.
16) A method to reduce side effects of chemotherapy in a cancer patient treated with chemotherapeutic agents comprising application of Newcastle Disease virus before, together, or after the chemotherapeutic agent to said patient.
17) A method to reduce side effects of chemotherapy in a cancer patient treated with chemotherapeutic agents according to object 16 comprising application of a Newcastle Disease virus clone according to at least one of object 1-4 before, together, or after the chemotherapeutic agent to said patient.
18) A method to reduce side effects of chemotherapy in a cancer patient treated with chemotherapeutic agents according to object 16 or 17, wherein the side effect is selected from nausea, vomiting, hair loss, fatigue, loss of appetite intestinal problems, loss of appetite and weight changes.
19) A method to reduce radionecrosis in a cancer patient treated with radiation comprising the application of a Newcastle Disease virus before, together, or after radiotherapy to said patient.
20) A method to reduce radionecrosis in a cancer patient treated with radiation according to object 19 comprising the application of a Newcastle Disease virus clone according to at least one of object 1-4 before, together, or after radiotherapy to said patient.
21) A method to reduce side effects including acute or chronic sequelae of radiotherapy in a cancer patient treated with radiation comprising the application of a Newcastle Disease virus clone according to at least one of object 1-4 before, together, or after radiotherapy to said patient.
22) A method to reduce side effects of radiotherapy in a cancer patient treated with radiation according to object 21, wherein the side effect of radiotherapy is selected from fatigue, anorexia, skin changes (or other acute symptoms depending on the exposed organs), diarrhea, incontinence, painful urination, frequency in urination, difficulty in swallowing, dryness of the mouth, tenderness, ulceration, cough, shortness of breath, sore throat, hoarseness, radionecrosis of the brain tissue or spinal cord, soft tissue necrosis, osteo-radio-necrosis, subcutaneous fibrosis, atrophy, telangiestasia, chronic necrosis, unresolved ulceration, stricture formation, severely decreased saliva formation, xerostomia, local myelopathies, chondro-necrosis, ulceration or stricture of the esophagus, fibrosis, pneumonitis or chronic irritation of the bowel or rectum.

23) A method to increase the quality of life in a cancer patient by amelioration of severe anorexia, loss of energy, depression, inertia, nausea, or fatigue comprising the application of a Newcastle Disease virus to said patient.

24) A method to increase the quality of life in a cancer patient according to object 23 comprising the application of a Newcastle Disease virus clone according to at least one of object 1-4 to said patient.

25) A method of palliative treatment of an advanced cancer patient comprising the application of a Newcastle Disease virus to said patient.

26) A method of palliative treatment of an advanced cancer patient comprising the application of a Newcastle Disease virus clone according to at least one of object 1-4 to said patient.

27) A pharmaceutical composition for the treatment of cancer comprising as an active ingredient a Newcastle Disease virus clone according to at least one of object 1-4 together with physiologically acceptable additives.

28) A pharmaceutical composition for the treatment of cancer comprising as an active ingredient a Newcastle Disease virus clone according to at least one of object 1-4 in freeze dried form together with physiologically acceptable additives.

29) A pharmaceutical kit for the treatment of cancer according to object 5 comprising a pharmaceutical composition according to object 27 or 28 and a pharmaceutical composition comprising a chemotherapeutic agent.

30) A pharmaceutical kit for the treatment of cancer according to object 29 wherein the chemotherapeutic agent is selected from: alkylating agents, anti-metabolites, anti-tumor antibiotics, topoisomerase inhibitors, mitotic inhibitors, targeted therapies, differentiating agents, especially from:
arsenic trioxide, adriamycin, BCNU, bexarotene, bleomycin, carboplatin, cisplatin, decarbazine, doxorubicin, 5-fluorouracil, methotraxate, taxol, temozolomide, vinblastine, vincristine, azacitidine, azathioprine, capecitabine, chlorambucil, cyclophosphamide, cytarabine, daunorubicin, docetaxel, doxifluridine, epirubicin, epothilone, etoposide, gemcitabine, hydroxyurea, idarubicin, imatinib, mechlorethamine, mercaptopurine, mitoxantrone, oxaliplatin, paclitaxel, pemetrexed, sorafenib, teniposide, tioguanine, tretinoin, valrubicin, vindesine, vinorelbine, imitanib, gefitinib, erlotinib, sunitinib, bortezomib.

31) A method of manufacture of a NDV virus clone according to objects 1-4, comprising the steps of
I. Generating a purified clonal viral clone (e.g. through multiple plaque purification)
II. Inoculating Specific Pathogen Free (SPF) chicken eggs with the clonal clone
III. Incubating the SPF eggs
IV. Chilling the SPF eggs
V. Harvesting the allantoic fluid from the SPF eggs
VI. Removing-debris from the allantoic fluid—possibly using filtration and or centrifugation VII. Ultracentrifugation of the allantoic fluid.

32) A method of manufacture of a NDV virus composition according to object 31 furthermore comprising the steps of:

VIII. Formulating and Filling Individual Containers

IX. Lyophilization- and Freeze Drying of Finished Product.

33) A Newcastle Disease Virus which is purified and freeze-dried.

34) A Newcastle Disease Virus according to object 33 in which the Newcastle Disease Virus a) is interferon insensitive and has an ICPI between 1.2 and 2.0, preferably between 1.2 and 1.5 or b) comprises the DNA nucleotide sequence of SEQ ID NO: 1 or c) is identical to the virus deposited with European Collection of Cell Cultures as Accession Number 06112101 on Nov. 21, 2006.

An alternative object of the invention is the use of a Newcastle Disease Virus Clone which has an ICPI equal or above 1.4, preferably equal or above 1.6, most preferably equal or above 1.75 in the treatment of cancer, the maximum ICPI score being 2.0. Newcastle Disease strains having these ICPI values are known in the prior art and are available from different sources such as the Central Veterinary Laboratory, New Haw Addlestone, United Kingdom.

Strains of the above identified property (ICPI score) include the strains Mukteswar, Roakin, Beaudette C, GB Texas, NY Parrot 70181 1972, Italien, Milano, Herts'33/56. These strains can be obtained from sources in Yugoslavia, India, USA, Portugal and Italy.

As mentioned above these strains are known and obtainable from public sources. They have been used for experimental purposes (especially in animal diseases) and for vaccination procedures in poultry). However, these strains have never been used for the manufacture of drugs for the treatment of human diseases, such as cancer. A preferred group of strains is interferon-insensitive. "Interferon insensitivity" is supposed to mean that cell proliferation does not change in the presence of interferon compared to the absence of interferon.

It has turned out, that the use of Newcastle Disease Virus (NDV) strains having an ICPI of 1.4 and above are very effective in treatment of human cancer. Newcastle Disease Virus strains having an ICPI of 1.4 These NDV strains are effective in the treatment of cancer by causing tumor cell death. They are moreover effective for a preventative form of biological cancer therapy, destroying nascent or residual cancer cells or decreasing the risk of development of metastatic lesions.

The virus strains can be used to treat the various kinds of cancer mentioned earlier in this application (see object No. 13). They can be used as the sole treatment or in combination with chemotherapy, radio therapy, immunotherapy or surgery. They can be administered as described earlier in this application (see object No. 7). A single dose received by a patient generally contains 1×105 to 1×1012 virus particles, preferable 1×106 to 1×1010 virus particles, most preferably 1×107 to 1×109 virus particles. A patient may receive one or more doses (frequent administration between three times a day to once per month), (see object Nos. 9 and 10).

Treatment of patients with the virus strains disclosed above results in improvement of their respective cancer disease. In addition said treatment usually reduces the pain perception in cancer patients. It furthermore reduces side effects of chemotherapeutic agents (when applied in combination with such chemotherapeutic agent, such as nausea, vomiting, hair loss, fatigue, loss of appetite, intestinal problems, and weight changes), (see object Nos. 14-26)

Further details of application forms, manufacturing processes, pharmaceutical compositions may be found earlier in this document. The methods described there may be easily adapted to the needs of Newcastle Disease strains having an ICPI of 1.4 and above.

It has been found that a new clone of NDV which is interferon insensitive and which has an ICPI between 1.2 and 2.0 is particularly beneficial in cancer therapy having properties which have not been obvious to experts skilled in the art.

A particularly beneficial NDV strain for cancer therapy is referred to as "MTH-68H/VB", as studies have indicated that this NDV clone may be successful in destroying tumors when other cancer therapies, including other NDV strains and their formulations have failed. This beneficial new NDV strain is variously referred to herein as MTH-68H/VB, MTH-68/H-VB, MTH-68/HVB, MTH-68/VB, MTH-68/H/VB and MTH-68/HVB, all of which designations refer to the very same NDV strain. Its inherent high potency allows MTH-68/H-VB to possibly be given at lower effective doses; making it also possible to be applied using less invasive non intravenous forms of administration. MTH-68/H-VB has been demonstrated to have a markedly synergistic effect with other modes of cancer therapy, especially radiation therapy—while seeming to have a cyto-protective effect on normal cells, thus making it an ideal candidate not only as a sole form of cancer therapy, but also as an onco therapy to be used as an adjunct to other more traditional therapies.

Surprisingly, it has been found that a Newcastle Disease Virus clone which is interferon insensitive and has an ICPI between 1.2 and 2.0 (preferably between 1.2 and 1.5) shows superior oncolytic properties compared to previous strains.

More particularly, it has been found that a Newcastle Disease Virus clone which is comprising the DNA nucleotide sequence of SEQ ID NO: 1 is an example of such a Newcastle Disease Virus clone. Also, it has been found that the virus deposited with European Collection of Cell Cultures as Accession Number 06112101 is an example of such a Newcastle Disease Virus clone.

The term clone as used herein refers to viruses that are genetically homogeneous as it has been found that previous virus compositions used in the art are genetically heterogenous.

Surprisingly, a particular new clone of NDV named as MTH-68/H-VB, has been found to have superior oncolytic properties. The new NDV clone is characterized (a) By its nucleotide and predicted amino acid sequences in the fusion (F) protein gene. Protein sequence at the C-terminus of the F2 protein and, the N-terminus of the F1 protein. Amino acid residues are numbered from the N-terminus of the amino acid sequence deduced from the nucleotide sequence of the F0 gene, 113-116 corresponds to residues −4 to −1 from the cleavage site
(b) By its plaque size, shape and appearance
(c) By the ICPI of the clone
(d) By its uniquely significant interferon induction capacity
(e) By its unique interferon insensitivity and
(f) By its ability to destroy tumour cells under different conditions
(g) By its compelling cancer associated pain-reducing properties
(h) By its potent synergistic potentiating effect on other modes of cancer treatments; including chemotherapy and radiation therapy.
(i) By its ability to lessen the deleterious side effects of chemotherapy and radiation therapy—thereby rendering more applicable these other traditional onco-therapeutic modalities.
(j) By the full nucleotide sequence which is disclosed in SEQ ID NO: 1 (Annex).
(k) By the cloned culture deposited on Nov. 21, 2006 with the European Collection of Cell Cultures as Accession Number 06112101.

BRIEF DESCRIPTION OF THE DRAWINGS

FIG. 1 illustrates the two sequences of the F gene, namely, the nucleotide sequence of SEQ ID NO: 2 and the amino acid sequence of SEQ ID NO: 3.

FIG. 2 illustrates the plaques of the MTH-68 H/VB clone (resulting from the test according to Schloer/Hanson.

FIG. 3 illustrates the plaques before plaque purification.

FIG. 4 is a comparison of virulence and cytopathology of various NDV strains.

FIG. 5 illustrates the interferon induction of different NDV strains.

FIG. 6 illustrates the IFN-beta effect on the growth of HEK293 cells (Exp. A).

FIG. 7 illustrates the IFN-beta effect on the growth of HEK293 cells (Exp. B).

FIG. 8 illustrates the effect of interferon-beta on the cytotoxicity of MTH-68H/VB (MTH) in HEK293 cells (Exp. A).

FIG. 9 illustrates the effect of interferon-beta on the cytotoxicity of MTH-68H/VB (MTH) in HEK293 cells (Exp. B).

FIG. 10 illustrates the effect of anti-IFN-beta on the growth of F11 primary human fibroblast cells (Exp. C).

FIG. 11 illustrates the effect of anti-IFN-beta on the cytotoxicity of MTH-68H/VB in F11 primary human fibroblasts (Exp. D).

FIG. 12 illustrates the effect of anti-IFN-beta on the cytotoxicity of MTH-68H/VB in F11 primary human fibroblasts (Exp. C).

FIG. 13 illustrates the effect of anti-IFN-beta on the cytotoxicity of MTH-68H/VB in F11 primary human fibroblasts (Exp. D).

FIG. 14 illustrates the cytotoxic effect of MTH-68H/VB on different cell lines.

FIG. 15 illustrates the cytotoxic effect of MTH-68H/VB on different cell lines.

FIG. 16 illustrates the cytotoxic effect of different NDV strains (H-fibroblast cell line).

FIG. 17 illustrates the cytotoxic effect of different NDV strains (HeLa cell line).

FIG. 18 illustrates the cytotoxic effect of different NDV strains (293 cell line).

FIG. 19 illustrates the cytotoxic effect of. MTH-68H/VB on BC-1, HT-3 and 293 cells.

FIG. 20 illustrates the effect of MTH-68H/VB on DAOY, SK-N-FI and IMR-32 cells.

FIG. 21 illustrates the effect of MTH-68H/VB on OVCAR cells.

FIG. 22 illustrates the effect of MTH-68H/VB on C-41 cells.

FIG. 23 illustrates the effect of MTH-68H/VB treatment on the growth of subcutaneous G1261 tumors (weekly treatment).

FIG. 24 illustrates the effect of MTH-68H/VB treatment on the growth of subcutaneous G1261 tumors (daily treatment).

FIG. 25 illustrates the combined effect of MTH-68H/VB treatment and tumor irradiation on the growth of subcutaneous G1261 tumors.

FIG. 26 illustrates the survival of tumor bearing mice after combined treatment with MTH-68H/VB and irradiation.

FIG. 27 illustrates tumor growth rate after combined treatment with irradiation, temozolomide and MTH-68H/VB—experiment 1.

FIG. 28 illustrates tumor growth rate after combined treatment with irradiation, temozolomide and MTH-68H/VB—experiment 2.

FIG. 29 illustrates the effect of MTH-68H/VB, irradiation and BCNU treatment on the tumor size in tumor bearing mice.

FIG. 30 illustrates the survival of tumor bearing mice (%).

FIG. 31 illustrates the family tree of known NDV virus strains.

FIGS. 32 and 33 show details of the genes and open reading frames for MTH-68H/VB.

DETAILED DESCRIPTION OF THE INVENTION

One NDV clone according to the invention may be described as follows:

1. Description of the New Clone by the Characterization of the Genome of MTH-68H/VB Virus Strain by Sequencing The genome was amplified in five overlapping portions. Three sequence specific primers were used for the RT and three primer pairs for the amplification of the inner regions encompassing 94% of the genome amplified in five overlapping portions.

The genomic RNA sequence of MTH-68/VB consists of 15186 nt. The 3' and 5' ends of the genome comprise the leader and trailer regions. The leader sequence is 55 nt long while the trailer sequence is 113 nt in length in MTH-68/VB. NDV strains have 114 nt trailer region in general.

The negative-strand RNA genome of MTH-68/VB contains six genes encoding six major structural proteins in 3'→5' direction (3'NP-P-M-F-HN-L 5') and two additional non-structural proteins (V and W). Structural proteins are NP: 489 aa (amino acids), P: 395 aa, M: 364 aa, F: 553 aa, HN: 571 aa, L: 2204 aa in length respectively.

During transcription one or two non-templated G residues can be inserted at the conserved transcriptional editing-site (UUUUUCCC) of SEQ ID NO: 6 within the P gene, producing two alternative ORFs. The phosphoprotein, the V (+1 frame) and the W (+2 frame) share the amino-terminal and vary at their carboxy-terminal ends in length and amino acid composition [Steward et al. 1993]. The sequence of the transcriptional editing site of MTH-68/VB is 2281 UUUUUCCC2288 of SEQ ID NO: 7. The ORF of the V protein is 717 nt in length from nt position 1888 to 2607 of the genomic RNA sequence and encodes a protein of 239 aa residues in strain MTH-68/VB. The ORF of the W protein is 681 nt long from nt position 1888 to 2571 of the genomic RNA sequence and encodes a protein of 227 aa in length.

Length of intergenic regions of MTH-68/VB ranges from 1 to 47. The NP-P, P-M, and M-F junctions are only one nt, intergenic sequence between F-HN genes consist of 31 nt, whereas HN-L junction is 47 nt long.

Figure 33:
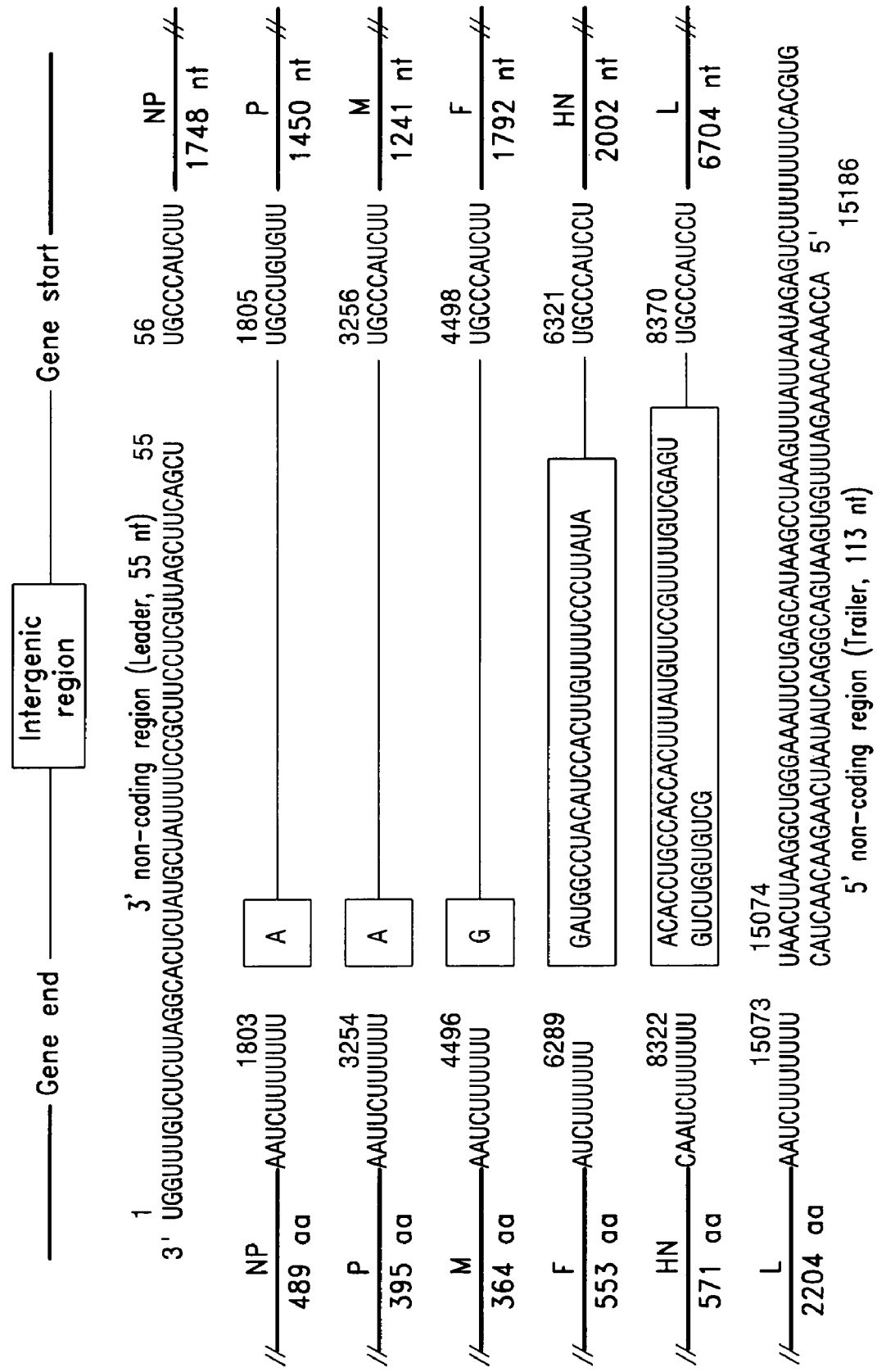

Details of the genes and open reading frames are summarized in FIGS. 32 and 33 and map of the complete genomic RNA of MTH-68/VB is described in the attached sequence listing (SEQ ID NO: 1) as hard-copy. With respect to FIG. 32, the following sequences and their corresponding numbers in the attached sequence listing are illustrated: UGCCCAUCUU of SEQ ID NO: 8; AAUCU$_7$ of SEQ ID NO: 9; UGCCUGUGUU of SEQ ID NO: 10; AAUUCU$_6$ of SEQ ID NO: 11; UGCCCAUCUU of SEQ ID NO: 12; AAUCU$_6$ of SEQ ID NO: 13; UGCCCAUCUU of SEQ ID NO: 14; AAUUCU$_6$ of SEQ ID NO: 15; GAUGGCCUAC AUCCACUUGU UUUCCCUUAU A of SEQ ID NO: 16; UGCCCAUCUU of SEQ ID NO: 17; AAUUCU$_6$ of SEQ ID NO: 18; ACACCUGCCA CCACUUUAUG UUCCGUUUG UCGAGUGUCU GGUGUCG of SEQ ID NO: 19; UGCCCAUCCU of SEQ ID NO: 20 AAUCU$_7$ of SEQ ID NO. 21. With resect to FIG. 33, the following sequences and their corresponding numbers in the attached sequence listing are illustrated: UGGUUUGUCU CUUAGGCACU CUAUGCUAUU UUCCGCUUCC UCGUUAGCUU CAGCU of SEQ ID NO: 22; UGCCCAUCUU of SEQ ID NO: 23; AAUCUUUUUUU of SEQ ID NO: 24; UGCCUGUGUU of SEQ ID NO: 25; AAUUCUUUUUU of SEQ ID NO: 26; UGCCCAUCUU of SEQ ID NO: 27; AAUCUUUUUU of SEQ ID NO: 28; UGCCAUCUU of SEQ ID NO: 29; AUCUUUUUU of SEQ ID NO: 30; GAUGGCCUAC AUCCACUUGU UUUCCCUUAU A of SEQ ID NO: 31; UGCCCAUCCU of SEQ ID NO: 32; CAAUCUUUUUU of SEQ ID NO: 33; ACACCUGCCA CCACUUUAUG UUCCGUUUUG UCGAGUGUCU GGUGUCG of SEQ ID NO: 34; UGCCCAUCCU of SEQ ID NO: 35; AAUCUUUUUUU of SEQ ID NO: 36; UAACUUAAGG CUGGGAAAUU CUGAGCAUAA GCCUAAGUUU AUUAAUAGAG UCUUUUUUUC ACGUGCAUCA ACAAGAACUA AUAUCAGGGC AGUAAGUGGU UUAGAAACAA ACCA of SEQ ID NO: 37.

One object of the invention is therefore a Newcastle Disease Virus clone comprising the DNA nucleotide sequence of SEQ ID NO: 1.

2. Description of the Virulence and Pathogenicity of the New Clone by the Determination of its Nucleotide and Predicted Amino Acid Sequences in the Fusion (F) Protein Gene The new clone MTH-68H/VB has been characterized by its nucleotide and predicted amino acid sequences in the fusion (F) protein gene, Protein sequence at the C-terminus of the F2 protein and, the N-terminus of the F1 protein. Amino acid residues are numbered from the N-terminus of the amino acid sequence deduced from the nucleotide sequence of the F0 gene, 113-116 corresponds to residues −4 to −1 from the cleavage site During replication, ND virus particles are produced with a precursor glycoprotein, F0, which has to be cleaved to F1 and F2 for the virus particles to be infectious. This post-translation cleavage is mediated by host-cell proteases. Trypsin is capable of cleaving F0 for all ND virus strains.

It would appear that the F0 molecules of viruses virulent (for chickens) can be cleaved by a host protease or proteases found in a wide range of cells and tissues, and thus spread throughout the host damaging vital organs, but F0 molecules in viruses of low virulence are restricted in their cleavability to certain host proteases resulting in restriction of these viruses to growth only in certain host-cell types.

Most ND viruses that are virulent (pathogenic for chickens) have the sequence $^{112}$R/K-R-Q-K/R-R$^{116}$ of SEQ ID NO: 4 at the C-terminus of the F2 protein and F (phenylalanine) at residue 117, the N-terminus of the F1 protein, whereas the viruses of low virulence have sequences in the same region of $^{12}$G/E-K/R-Q-G/E-R$^{116}$ of SEQ ID NO: 5 and L (leucine) at residue 117. Thus there appears to be the requirement of at least one pair of basic amino acids at residues 116 and 115 plus a phenylalanine at residue 117 and a basic amino acid (R) at 113 if the virus is regarded velogenic (showing virulence for chickens; OIE Manual)]

Based on the partial sequence of the fusion gene (F) between nucleotide positions 47 and 420, the MTH-68/VB strain has virulent sequence of proteolytic cleavage site due to the dibasic motif and an F aa at position 117. (see in red). Cleavage occurs between 116 and 117 amino acids.

It is therefore an object of the invention to provide a Newcastle Disease Virus clone having a virulent sequence of proteolytic cleavage site with a dibasic motif and an F aa at position 117. More particularly it is an object of the invention to provide a Newcastle Disease Virus having a sequence with at least one pair of basic amino acids at residues 116 and 115 plus a phenylalanine at residue 117 and a basic amino acid at 113.

3. Description of the Virulence and Pathogenicity of the New Clone by the Determination of its Plaque Form and Size by the Test Described by Schloer and Hanson (Journal of Virology, 2 (1968), P. 40-47)

The authors of this publication did believe in 1968 that the ability of the Newcastle disease virus strains to produce large plaques is related to their virulence in chickens. They compared the plaque-size under standard conditions in chicken embryo fibroblast cell monolayers. Markedly larger plaques were produced by the velogenic (high virulence) strains. Only small plaques were created by the mesogenic (intermediate virulence) strains, and plaques were rarely found in lentogenic (low virulence) strains.

Although this test has never been accepted in the scientific community as a criteria in the description of NDV virus strains; beside the other parameters measured, we also studied the plaque forming ability of our new NDV clone.

The monolayer cultures of chicken embryo fibroblast (CEF) used for the plaque assay were prepared from 10-day-old SPF chicken embryos. Cell monolayers were grown in petri dishes (Anumbra) 5 cm in diameter ($3.5 \times 10^6$ cells per dish) and were infected by the clone virus propagated in SPF chicken embryos. Plaque formation in CEF culture by the MTH-68H/VB strain is shown in FIG. 2. The plaques formed within 48 to 72 h by the clone strains were regarded as "large plaques". Plaques of the strain were well-defined, circular. The plaques first appeared at 36 to 48 hr after infection and measured between 2.5 to 4.9 mm on the fifth day after inoculation. Microscopically their borders were not clearly defined. According to the results of the specific test first described by Schloer and Hanson the new clone can be regarded as velogenic NDV and would not be considered a mesogenic strain

4. Description of the Origin of the New Clone and the Difference Between the New Clone and the Parent Virus Stock The parent strain of the MTH-68H/VB was the "ancient" NDV poultry vaccine strain originated from UK (in the 1940-ies) which had remarkable genetic heterogeneity. To increase the homogeneity of the product and remove any defective particles plaque purification steps were performed multiple times. Plaque purification is a technique commonly used in those skilled in the art to obtain a clonal virus clone that holds desired characteristics typified by plaque size-shape and appearance (e.g. Massaab et al, In Plotkin and Mortimer, eds Vaccines, Philadelphia: WB Saunders Co., 1994 pages 78-801. The first partial purification resulted in a visually homogeneous virus population. During the propagation in CEF the plaques formed by the "purified" virus stock still showed a great variability (FIG. 3). From this virus population propagated in chicken fibroblast monolayer tissue culture one plaque containing desired characteristics from the several still various plaques was chosen and separated and further propagated. At a later date, this homogeneous virus population was again propagated in CEF and again underwent plaque purification where a single plaque was further chosen (third isolation) based on its size and appearance and propagated in SPF chicken embryos: After strict quality control the harvested virus suspension was used for the production of a new master seed of MTH-68H/VB.

5. Description of the Virulence and Pathogenicity of the New Clone by the Determination of its Intracerebral Pathogenicity Index (ICPI)

Newcastle Disease Viruses are divided into three different pathotypes characterized by the intracerebral pathogenicity index (ICPI).

Lentogenic (low virulent) strains have an ICPI of 0-0.7. Mesogenic strains are NDVs of moderate pathogenicity (ICPI 0.7-1.5) and velogenic (high pathogenic) strains are characterized by an ICPI >1.5. The maximum ICPI is 2.0.

The ICPI is determined by intracerebral injection of 50 µl of a virus dilution (haemagglutination titre (HA) of at least 24) in day-old chicks. The animals are observed for 8 days and are assessed once daily (healthy=0, ill=1, dead=2). The ICPI is calculated by dividing the sum by the number of assessments.

It has been found that a Newcastle Disease Virus having a ICPI between about 1.2 and 2.0, preferably between 1.2 and 1.5 does have improved oncolytic properties, especially when it is interferon insensitive (see below).

With the classical technique the ICPI of MTH-68/H-VB was found to fall between 1.2 and 1.5, tending towards increased virulence.

6. Description of the Unique Interferon Induction Capacity of the Clone

Interferons (IFNs) are natural cell-signaling proteins produced by the cells of the immune system of most vertebrates in response to challenges such as viruses, parasites and tumor cells. Interferons are produced by a wide variety of cells in response to the presence of double-stranded RNA, a key indicator of viral infection.

Interferon production has been stimulated by a variety of RNA- and DNA-containing viruses, including those with oncogenic properties such as polyoma and Rous sarcoma virus.

To investigate the interferon induction of different NDV strains (listed in FIG. 4) there were three system used.

The virus content of the chicken embryo (allantois cavity) or in chicken embryo fibroblast (CEF) cultures was inactivated by heat (65 C.° for 30 minutes) and the cultures were tested for the presence of interferon by an assay based on the reduction of cytopathic effect of a challenge virus (Sindbis).

In human and swine cell line the interferon induction was measured by the same technique (described by Falcoff at al. 1966) but for by the assay based on the reduction of cytopathic effect of a challenge virus (Sindbis) the amnion (human) and PK-15 (swine) cell line were used.

On the basis of our data we could conclude that all the studied non-inactivated virus strains could induce interferon production in a large magnitude. The most pronounced interferon production was seen in the PK-15 (pig kidney) and in the human (amnion membrane) cell line (FIG. 5). These results suggest that interferon induction by NDV involves components of the virion.

The interferon induction of the new clone MTH-68H/VB was significantly higher and more consequent in all the systems tested, which included several different NDV strains of varying virulence, using several different cell lines—under several different conditions.

It is an object of the invention to provide a NDV virus clone which significantly induces interferon in cells. Due to this behavior the NDV clone may successfully be used to treat diseases which have been shown to be interferon sensitive, such as Melanoma, (non-Hodgkins) Lymphomas, Leukemias (Chronic Myeloid Leukemia, Hairy Cell Leukemia), Breast cancer, Bladder Carcinoma, Renal cell carcinoma, Head and Neck cancer, Carcinoid tumors, Bile Duct, Pancreatic ca, Multiple Myeloma, Kaposi Sarcoma, as well as non-neoplastic interferon sensitive autoimmune and viral conditions such as Multiple sclerosis, Condylomata acuminata, Hepatitis, Herpes, Rheumatic Arthritis, Behcet's Disease, Idiopathic Pulmonary Disease, Aphthous stomatitis, Severe Malignant Osteoporosis, cervix cancer, or SARS (Severe Acute Respiratory Syndrome).

Because of the oncolytic and significant interferon inducing properties of the NDV clones according to the invention (especially MTH-68/HVB) it could be an ideal candidate to be used as part of cancer vaccine type therapies where it is combined with a patient's autologous tumor cells, and used in combination with other immune modulating factors as part a targeted immuno onco-therapy.

7. Description of the Unique Interferon Non-Sensitivity of the Clone

It is known that most of the viruses including the majority of the NDV strains are sensitive to interferon β (IFNβ). IFBβ inhibits the replication of the interferon sensitive NDV in sensitive cells. One can expect the cytotoxic effect of the interferon sensitive NDV strains to decrease with increasing IFNβ concentration.

We investigated whether the MTH-68H/VB clone is sensitive to interferon β and the presence of interferon β can modify the virus replication in various cell lines that are sensitive to MTH-68H/VB infection.

In the first set of experiments MTH-68H/VB sensitive HEK293 cell lines were infected at various multiplicity of infection (MOI, virus/cells) with MTH-68H/VB in the presence of different concentrations of IFNβ.

In the second set of experiments MTH-68H/VB resistant primary human fibroblast cells were treated with different concentrations of the virus in the presence of anti-IFNβ. Under these conditions the cytotoxic effect of MTH-68H/VB should have increased, if IFNβ influenced the viral replication.

During the studies the HEK293 cell line (human embryonic kidney transformed with adenovirus type 5) and F11 (primary human fibroblast) cell line were used. Both cell lines were cultured in Dulbecco's Modified Eagle Medium containing antibiotics (penicillin, streptomycin and amphotericin B) and fetal calf serum (10% and 20% for HEK293 and F11 cells, respectively). $2 \times 10^3$ cells were plated on 96 well culture dishes in 100 µl final volume. Twenty-four hours later the cells were infected with MTH-68H/VB at different multiplicity of infection (MOI). Cells were also treated either with IFNβ (R and D Systems) or with an antibody against IFNβ (R and D Systems). Seventy-two hours after NDV infection 20 µl WST-1 reagent (Roche) was added and cytotoxicity was assayed 2 hr later by measuring $OD_{490}$ values with a multi-well photometer.

Exp. A. HEK293 cells were plated on day 0. Cells were treated with 20, 200 or 2000 U/ml IFNβ on day 0, 1, 2 and 3. MTH-68H/VB infection was performed on day 1 at 0.001 or 0.01 MOI. Cytotoxicity was measured on day 4.

Exp. B. Experimental conditions were similar to Exp A, except that the cells were infected at 0.01 and 0.1 MOI.

Exp. C. F11 cells were plated on day 0. Cells were treated with 2, 10, 20 µg/ml anti-IFNβ on day 0, 1, 2 and 3. MTH-68H/VB infection was performed on day 1 at 0.001 or 0.01 MOI. Cytotoxicity was measured on day 4.

Exp. D. Experimental conditions were similar to Exp C, except that the cells were infected at 1 or 10 MOI. The final concentration of anti-IFNβ was 2 and 15 µg/ml.

Effect of IFNβ treatment on the cytotoxic effect of MTH-68H/VB: When the results were analyzed it was concluded that IFNβ did not affect cell proliferation (FIGS. 6 and 7).

IFNβ does not inhibit the cytotoxic effect of MTH-68H/VB The effect of IFNβ on the cytotoxicity of MTH-68H/VB was investigated on HEK293 cells using two replication of the study. (Exp. A and B). In both study the MTH-68H/VB was cytotoxic for HEK 293 cells at low MOI (lower than 1 MOO showing that MTH-68H/VB can replicate in this cell line (FIGS. 8 and 9, columns 1-3), and as a final conclusion we proved that IFNβ does not inhibits the cytotoxic effect of MTH-68H/VB, not even at very high IFNβ concentrations (FIG. 9, columns 4-12)

It is therefore an object of the invention to provide a NDV virus clone that is insensitive to interferons, especially Interferon β. Interferon insensitivity is supposed to mean that cell proliferation does not change in the presence of interferon compared to the absence of interferon.

The Effect of IFNβ Antibody Treatment on the Cytotoxicity of MTH-68H/VB in Primary Human Fibroblast Cells Next, we analyzed the effect of an antibody raised against IFNβ on the cytotoxic effect of MTH-68H/VB in F11 primary human fibroblast cells. Anti-IFNβ did not affect the proliferation of F11 cells in two independent experiments (Experiments C and D, FIGS. 10 and 11). Using two different stocks of MTH-68H/VB we could not detect a cytotoxic effect on fibroblast cells (FIGS. 12 and 13, columns 1-3). Neither low, nor high concentrations of anti-IFNβ treatments were able to increase the cytotoxic effect of MTH-68H/VB (FIG. 12, columns 4-12; and FIG. 13, columns 4-9).

There were indications that the cytotoxic effect of Newcastle disease virus (NDV) relies on the interferon production of the cell lines. According to this suggestion cells (usually normal cells) capable to show a strong interferon response are resistant to NDV infection, while tumor cells which lost their IFN response are sensitive to the cytotoxic effect of NDV. If this hypothesis is correct then the addition of IFNβ to tumor cells will restore their resistance against NDV. On the other hand by removing IFNβ from the neighborhood or culture media of normal cells (fibroblast, for instance) will increase their sensitivity to NDV infection. Our data contradicts this hypothesis, at least in or case of MTH-68H/VB, in the experimental models described.

IFNβ treatment of MTH-68H/VB sensitive HEK293 cells did not improve their resistance against MTH-68H/VB infection. Besides this, the removal of IFNβ from the culture medium of primary human fibroblast cells by antibody treatment did not increase their sensitivity to MTH-68H/VB. Our data demonstrates that the cytotoxic effect of MTH-68H/VB did not depend on the interferon production of the infected cells.

8. Comparative Studies of the Cytotoxic Effect of MTH-68/VB and Other NDV Strains on Various In Vitro Growing Cell Lines (Including Human and Rodent Brain Tumor Cell Lines, as Well as Normal Primary Human Fibroblast Cells)

8.1. Replication of MTH-68/H-VB in Different Cell Lines 8.1.1. The Cytotoxic Effect of MTH-68H/VB was Studied Under In Vitro Conditions in Different Primary and Established Cell Lines Using 20% Fetal Calf Serum.

In this study the following cell lines were used:

293N3S—human embryonic kidney transformed with adenovirus type 5, adapted to grow in suspension culture (bought from ATCC)

HeLa—human epithelial cell line established from a cervix tumor (bought from ATCC)

9L—established rat glioma cell line (bought from ECACC)

H-primary human fibroblast cell line (established from skin biopsy)

V-primary human fibroblast cell line (established from skin biopsy)

A-primary human fibroblast cell line (established from skin biopsy)

The cells were grown in the presence of 20% fetal calf serum, that is the optimal serum concentration for the primary human fibroblast cells. At this high serum concentration MTH-68H/VB had no cytotoxic effect on normal human fibroblasts. It had only moderate effect on rat (9L) glioma cells (FIG. 8. about 50% survival at 50 MOI). Contrary to this, 293N3S and HeLa cells were very sensitive to MTH-68H/VB treatment. Even, after infection at a very low MOI (0.005), all cells were killed by the virus.

The cytotoxicity assays suggested that MTH-68/H-VB could replicate in 293N3S and HeLa cells, but no infectious viral particles were formed in the other investigated cell lines.

8.1.2. The Cytotoxic Effect of MTH-68H/VB on Different Cell Lines Under In Vitro Conditions Using 10% Fetal Calf Serum.

To further study potential virus replications, the following cell lines were used:

293—human embryonic kidney transformed with adenovirus type 5 (bought from ATCC)

HeLa—human epithelial cell line established from a cervix tumor (bought from ATCC)

H-primary human fibroblast cell line (established in our lab from skin biopsy)

961107 primary human fibromatous meningeoma cells established at NINS 960612 primary human fibromatous meningeoma cells established at NINS 980128/2 primary human glioblastoma multiforme cells established at NINS $5 \times 10^3$ cells were plated on 96 well culture dishes in 100 µl final volume. Twenty-four hours later the cells were infected with the corresponding virus at different multiplicity of infection (MOI, virus/cell ratio: 0; 0.01; 0.1; 1; 10; 100) by adding 50 µl complete medium containing the virus. Seventy-two hours later 15 µl WST-1 (Roche) was added and cytotoxicity was assayed 1 hr later by measuring OD450 values with a multi-well photometer. The $OD_{450}$ values were converted to survival rates (%).

It is well known, that high serum concentrations might inhibit the infectivity of certain viruses (for instance adenovirus). Therefore, in these experiments only 10% fetal calf serum was added to the cell culture medium. This serum concentration is optimal for all cell lines, except for the primary fibroblasts, but primary human fibroblast cells are also able to grow in this medium. In the presence of 10% serum MTH-68H/VB at high MOI (10 and 100) was toxic for all cells but slightly for primary human fibroblast cells (H-fibroblasts, FIG. 15). The various primary human brain tumor cell lines (980128/2, 960612 and 961107) showed much higher sensitivity to MTH-68H/VB than the primary fibroblasts.

Beside the brain tumor and fibroblast cell lines, we also tested the sensitivity of HeLa cells to MTH-68H/VB treatments. HeLa cells were almost as sensitive as 293 cells, suggesting that the virus can replicate in these cells, as well.

8.2. Cytotoxicity of MTH-681H-VB and Other NDV Strains in Different Cell Lines

In this comparative study the cytotoxicity of different NDV strains were compared to the cytotoxicity of MTH-68H/VB. In the study the NDV strains were:

H/W—the Weybridge line of strain Hertfordshire

Mukteswar ("mesogenic" strain from Veterinarski Zavod, Subotica)

LaSota—the standard poultry vaccine strain

VP—the "avirulent" standard vaccine strain

The comparative cytotoxicity was studied on the 293, HeLa and H-fibroblast cell lines.

293—human embryonic kidney transformed with adenovirus type 5 (bought from ATCC)

HeLa—human epithelial cell line established from a cervix tumor (bought from ATCC)

H-primary human fibroblast cell line (established in our lab from skin biopsy)

For the assay $5 \times 10^3$ cells were plated on 96 well culture dishes in 100 µl final volume. Twenty-four hours later the cells were infected with the corresponding virus at different multiplicity of infection (MOI, virus/cell ratio: 0; 0.01; 0.1; 1; 10; 100) by adding 50 µl complete medium containing the virus. Seventy-two hours later 15 µl WST-1 (Roche) was added and cytotoxicity was assayed 1 hr later by measuring OD450 values with a multi-well photometer. The OD450 values were converted to survival rates (%)

8.2.1. Comparative Study on H-Primary Human Fibroblast Cell Line.

In these experiments 10% fetal calf serum was added to the cell culture medium. This serum concentration is optimal for all cell lines, except for the primary fibroblasts, but primary human fibroblast cells are also able to grow in this medium. In the presence of 10% serum MTH-68H/VB was slightly toxic for the fibroblast cell but only at very high MOI (10 and 100, FIG. 16).

The most pronounced effect was seen in the MTH-68H/VB treated cells, less but still perceptible effect was caused by the H/W strains while the others had no cytotoxic effect.

It can be concluded that under normal circumstances, ie unless applied at very high multiples of infection, the studied NDV strains are not cytotoxic to normal human cells.

8.2.2. Comparative Study on HeLa (Human Epithelial Cell Line Established from a Cervix Tumor) Cell Line In these experiments also 10% fetal calf serum was added to the cell culture medium. This serum concentration is optimal for all cell lines. In the presence of 10% serum MTH-68H/VB was highly toxic for the HeLa cells even in very low MOI (FIG. 11). The cytotoxic effect of MTH-68H/VB was significant higher than any other studied viruses especially at low MOI (0.01 and 0.1).

The sensitivity of HeLa cells suggest that only some of the ND virus strains can replicate in these cells. Among the studied strains MTH-68H/VB is the most effective.

8.2.3. Comparative Study on 293 (Human Embryonic Kidney Transformed with Adenovirus Type 5) Cell Line Similarly to the previous experiment, in the presence of 10% serum MTH-68H/VB was highly toxic for the 293 cells, even at very low MOI (FIG. 12). The cytotoxic effect of MTH-68H/VB was significant higher than any other studied viruses especially at low MOI (0.01 an 0.1).

The sensitivity of 293 cells suggests that only some of the ND virus strains can replicate in these cells. Among the studied strains MTH-68H/VB is the most effective.

8.3. The Cytotoxic Effect and the Potential Replication of MTH-68H/VB Strain in Different Cell Lines of Human Tumor Origin Cell Lines
Brain Tumors:
 HTB-186 (Daoy) cerebellar meduloblastoma, 4 years child
 CCL-127 (IMR-32) brain neuroblastoma. This cell line is sensitive to herpes, coxackie and vaccinia viruses, 13 months child
 CRL-2142 (SK-N-FI) neuroblastoma, 11 years child
Kaposi Sarcoma
 CRL-2230 (BC-1) B lymphocyte, lymphoma; contains EBV and KSHV
Cervix Tumors:
 CRL-1594 (C-41) epithelial cervix tumor, contains and expresses HPV-18
 HTB-32 (HT-3) epithelial cervix coming cloned from lymph node metastasis, HPV negative, p53+, Rb+
Ovarian Tumor
 OVCAR, ovarian carcinoma
Embryonic Kidney
 293—human embryonic kidney cell transformed with adenovirus type 5

Cytotoxicity Assay $5 \times 10^3$ cells were plated on 96 well culture dishes in 100 µl final volume. One day after the plating, the cells were transduced with MTH-68/H-VB at different multiplicities of infection (MOI) (100/1; 10/1; 1/1; 1/10 and 1/100). The cytotoxic effect was assessed 72 h later by WST-1 kit of Roche.

Figure 18:
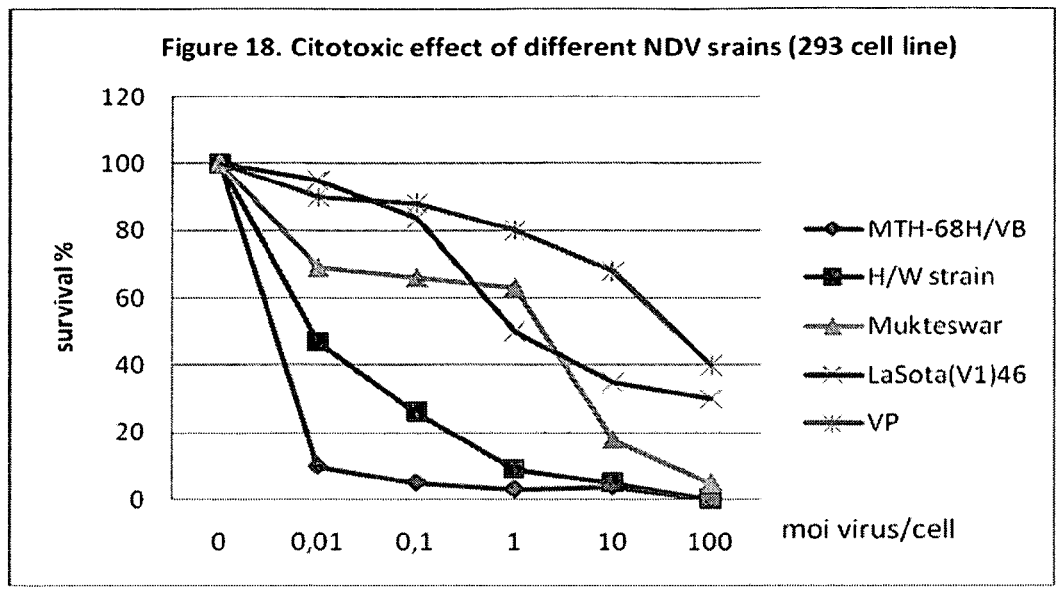
Figure 19:
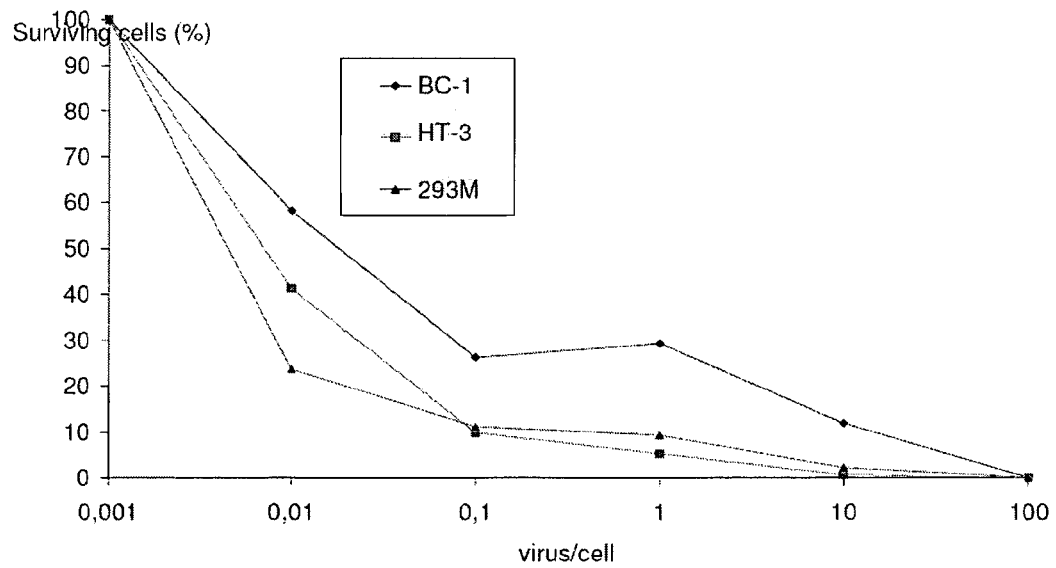

The cytotoxic effect of MTH-68H/VB was studied under in vitro conditions in different primary and established cell lines. The 293 cells were used as a positive control as it has been established that MTH-68H/VB replicates in these cells. MTH-68H/VB was cytotoxic on BC-1 (lymphoma) and HT-3 (cervix tumor) cells. The cytotoxicity was very similar to the one observed on 293 cells (FIG. 19). The virus was very toxic even at low multiplicity of infection for these cells.

Figure 20:
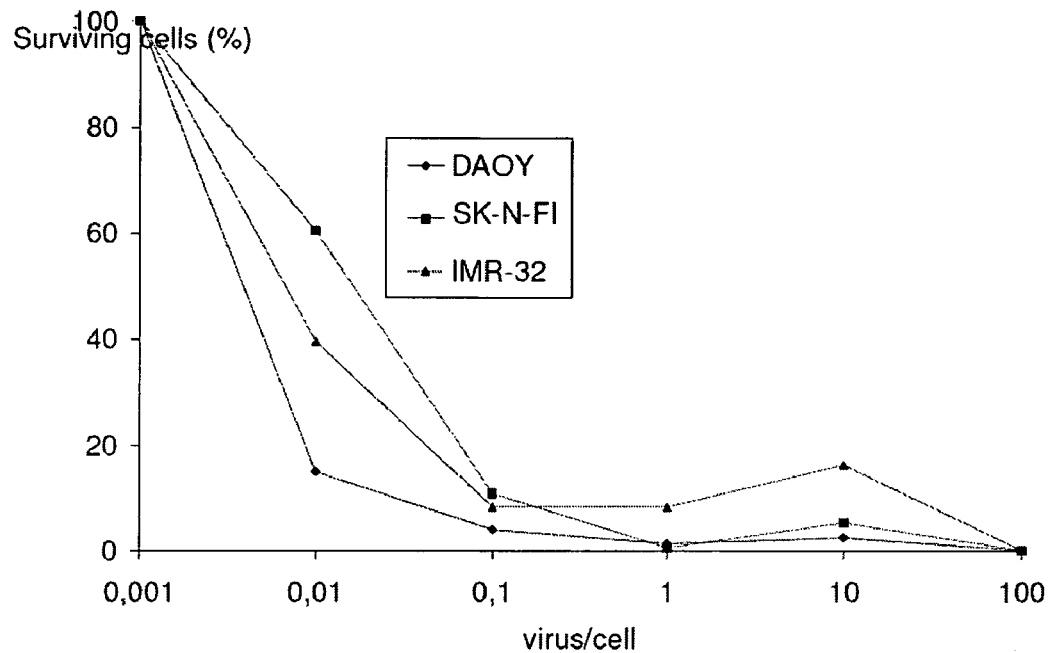
Figure 21:
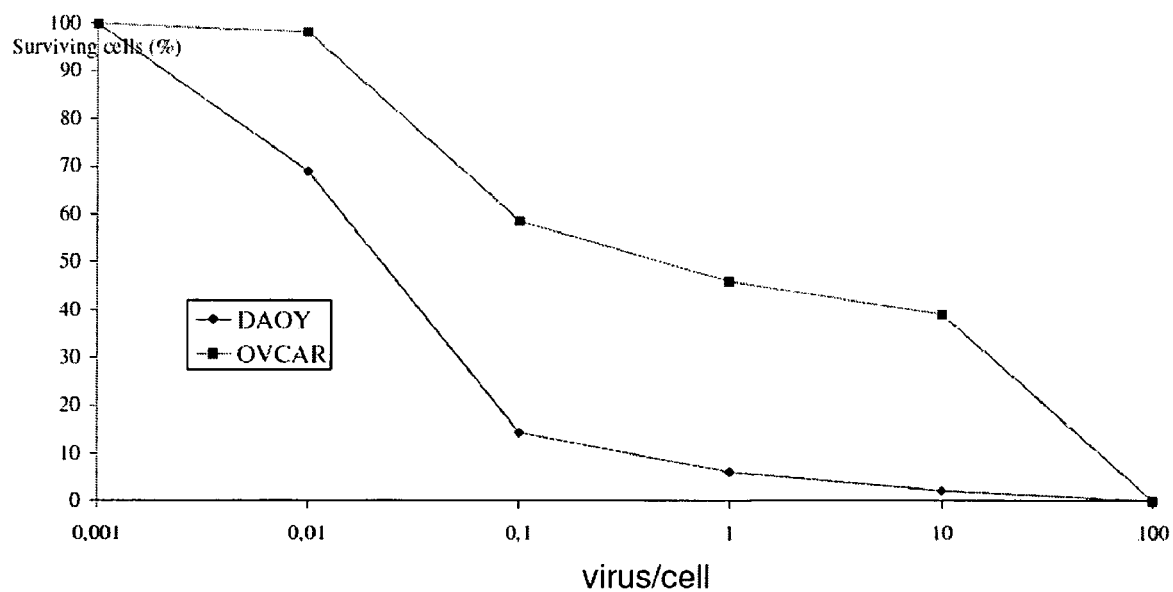
Figure 22:
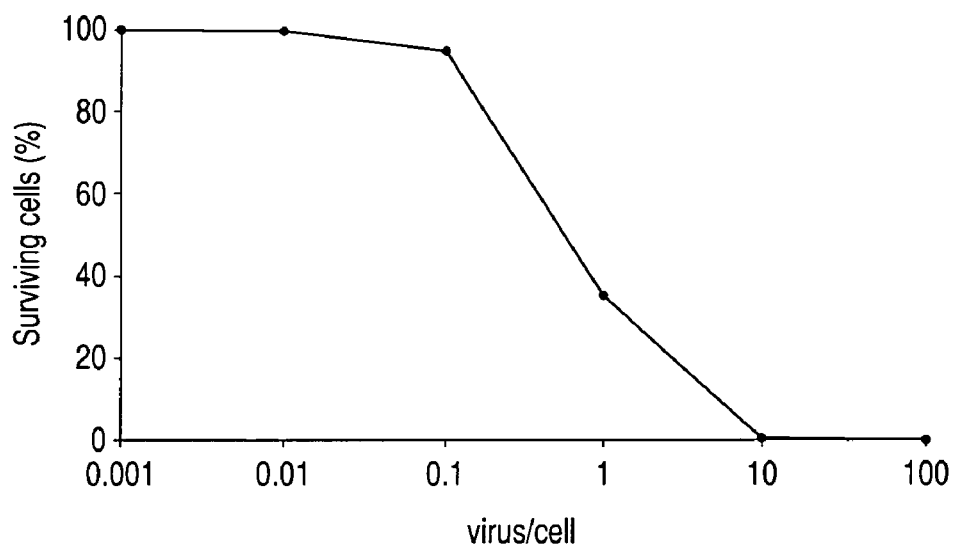

Similar strong cytotoxic effect was observed in DAOY (medulloblastoma), IMR-32 (neuroblastoma), SK-N-FI (neuroblastoma) (FIG. 20) cells. Less, but still considerable toxicity was detected on OVCAR (ovarian tumor) cells (FIG. 21). C-4I cervix tumor cells were killed by MTH-68/H-VB only at high multiplicity of infection (FIG. 22).

MTH-68H/VB efficiently killed BC-1, HT-3, DAOY, IMR-32, SK-N-FI and OVCAR cells even at low multiplicity of infection. Similar effect was seen on 293 cells. We formerly proved that in 293 cells the high toxicity of MTH-68H/VB could be explained by the replication of virus. These data therefore suggest that MTH-68H/VB can efficiently replicate in BC-1, HT-3, DAOY, IMR-32, SK-N-FI and OVCAR cells. In C-4I cells cytotoxicity was detected only at high multiplicity of infection. It suggests no viral replication in this cell line.

It is an important object of the invention to provide NDV virus clones with improved oncolytic potential compared to virus preparations which are currently available.

9. Description of MTH-68H/VB as a Potentiating Agent when Used Along with Other Onco-Therapeutic Modalities Including Chemotherapeutic Agents and Radiation Therapy In Vivo While having observed the potential oncolytic activity of viral therapy as a sole therapeutic agent able to treat cancer patients in advanced stages of disease, where other cancer treatment modalities had already been exhausted, the effect of using MTH-68H/VB in active combination with chemotherapeutic and or irradiation treatment was further explored in an experimental forum. In our experiments we attempted to mirror the actual course of patient therapy, giving an indication as to the actual practical application—as in a patient with a brain tumor—specifically using glioma as a model—the current standard mode of therapy being post surgical intervention, the patient first being treated with a course of radiation therapy followed by a specific type of chemotherapy, namely BCNU or Temozolomide.

It is an object of the invention to provide a NDV virus clone which is therapeutically effective in combination with other therapy modes, such as chemotherapy, radiotherapy or surgery.

9.1. In Vivo Application of MTH-68H/VB Alone or in Combination with Irradiation.

The aim of the study was to study the in vivo anti-tumour effect MTH-68H/VB, either alone or in combination with other therapeutic modalities. The influence of MTH-68H/VB dose and dose schedule was also investigated.

The virus stocks were dissolved in 1 ml PBS. The stocks were divided into 200 µl aliquots and stored at –70° C. During our work some aliquots were repeatedly thawed and re-frozen.

GI261—established murine glioma cell line (NCI, USA) was used. The cells were maintained in DME medium containing 10% fetal calf serum and antibiotics.

GI261 cells were harvested, washed once in PBS and suspended in a small volume of PBS ($1-2 \times 10^7$ cells/ml). Subcutaneous tumours were established in C57Bl/6 mice by transplanting $1-2 \times 10^6$ GI261 cells into the right limb of the animals in 200 µl final volume of PBS. The diameters of subcutaneous tumours were measured in 3-4 days interval with calliper and tumour volume was calculated as length× width×height×π/6. Mice were killed when they were moribund or one hundred days after tumour induction. All mice were carefully autopsied. All animal treatment groups were composed of 5 mice.

In the first protocol, tumors were induced with the subcutaneous injection of $2 \times 10^6$ GI261 cells. Tumors were clearly palpable (about 3-4 mm tumor diameter) after one week and tumor treatment was started with the intra-tumor injection of MTH-68H/VB in a 50 µl final volume. Several needle tracks were applied each time to ensure even intratumoral distribution. Control mice were left either untreated or treated with the intratumoral injection of PBS alone.

Treatment Protocol I
 Group 1—untreated controls
 Group 2—treated with daily injections of PBS
 Group 3—treated with once/week injections of PBS
 Group 4—treated with daily injections of $1 \times 10^7$ MTH-68H/VB
 Group 5—treated with daily injections of $1 \times 10^5$ MTH-68H/VB Group 6—treated with once/week injections of $1\times10^7$ MTH-68H/VB Group 7—treated with once/week injections of $1\times10^5$ MTH-68H/VB The treatment was done for a two weeks period.

In the second protocol, tumors were induced with the subcutaneous injection of $1\times10^6$ GI261 cells. Tumors were weakly palpable (about 1-2 mm tumor diameter) after two weeks and tumor treatment was started with the intra-tumor injection of MTH-68H/VB in a 50 μl final volume as mentioned above.

Treatment Protocol II

Group 1 untreated controls

Group 2 treated with daily injections of PBS

Group 3 treated with twice/week injections of PBS

Group 4 treated with daily injections of $1\times10^7$ MTH-68H/VB

Group 5 treated with twice/week injections of $1\times10^7$ MTH-68H/VB

Group 6 same as group 2, but before the first PBS treatment, the tumor bearing limb of the mice was irradiated with 4 Gy x-ray irradiation Group 7 same as group 4, but before the first MTH-68H/VB treatment, the tumor bearing limb of the mice was irradiated with 4 Gy x-ray irradiation The treatment was done for a two weeks period.

Tumor Irradiation

The tumor-bearing right limb of the anaesthetized mice was irradiated with 4 Gy X-ray radiations (THX-250 Therapeutic X-ray Source, Medicor, Budapest, Hungary, dose rate: 1.003 Gy/min). A lead tube shielded the other part of the body to protect it from radiation.

Results

In the first set of experiments somewhat bigger tumors were treated either with once a week, or with daily intratumoral injections of two different doses of MTH-68H/VB ($1\times10^7$ and $1\times10^5$ viral particles/injections) (FIGS. 23 and 24, respectively).

The mock treatment with intratumoral PBS injections resulted in a slightly retarded tumor growth. However, the intratumoral injections of MTH-68H/VB clearly showed a superior tumor growth retardation effect. It was also clear that the daily viral treatment was much more efficient than the once a week virus injection, and the higher viral doses were superior to the lower ones.

Usually, an anti-tumor protocol is much more efficient, if the tumors are small at the time of the treatment. This possibility was modeled in the second set of experiments. Tumors were induced with the transplantation of less GI261 tumor cells. Beside this, in the second protocol only the larger MTH-68H/VB doses ($1\times10^7$) were applied and the once a week treatment was replaced with twice a week intra-tumor virus injections. Again, the intratumoral MTH-68H/VB injection resulted in the retardation of the tumor growth compared to mock treated controls and the daily treatment was superior to the twice a week viral injections (FIG. 25).

Quite interestingly, the intra-tumor or peri-tumor MTH-68H/VB injections prevented the outgrowth of the tumors in a few animals (FIG. 25). Note, that the tumor growth curve at the beginning shows the average volume of five tumors per treatment group. The sudden drop in the tumor volume represents that one or two of the large tumor-bearing, moribund mice were killed by anesthesia for ethical reasons. The return of the tumor growth curve to the near baseline represents mice cured from the tumor by MTH-68H/VB treatments (FIG. 25). The complete elimination of small tumors by repeated MTH68/H treatments is more obvious on FIG. 26, where the survival of tumor bearing mice is shown.

Conclusion:

When the combined effect of MTH-68H/VB treatment and local tumor irradiation was analyzed it was concluded that the radiation alone eliminated tumor growth only in a small percentage of the animals. Interestingly, the combination of intratumoral MTH-68H/VB injections with local tumor irradiation eliminated the outgrowth of all tumors (FIGS. 25 and 26).

It was also concluded that the intratumoral injections of high MTH-68H/VB injections at least slows down the progression of large tumors and small tumors may be completely eliminated by MTH-68H/VB. Intra-tumor MTH-68H/VB treatment might be very efficiently combined by local tumor irradiation. The most probable explanation is the direct cytotoxic effect of MTH-68H/VB. The dramatic effect of combination therapy between MTH-68H/VB and radiation therapy in this particular cell line was seen despite the relative insensitivity of this particular cell line to MTH-68H/VB in comparison to other cell lines tested (as described earlier in text), thus further demonstrating the positive synergistic effect of viral therapy and radiation therapy.

9.2 The Antitumor Effects of the MTH68-H/VB Therapy, Combined with Temozolomide Chemotherapy and Radiotherapy Gliomas are routinely treated by surgery which is often followed by radiation and chemotherapies. Among the chemotherapy agents used the administration of temozolomide (Temodar, Temodal) replacing BCNU (bis-chloronitrosourea, Carmustine) is becoming a standard mode of treatment. The aim of the present study was to investigate the combined antitumor effects of the MTH-68H/VB viral therapy, with chemotherapy such as temozolomide chemotherapy and radiotherapy.

9.2.1. Tumor Model

In vitro growing GI261 cells were harvested, washed twice in PBS and suspended in a small volume of PBS ($1-2\times10^7$ cells/ml). Subcutaneous tumours were established in C57Bl/6 female mice by transplanting $1-2\times10^6$ GI261 cells into the right limb of the animals in 100 μl final volume of PBS. The GI261 murine glioma cell line was cultured in Dulbecco's Modification of Eagle's Minimal Essential Medium (DME) as described (T. Szatmári, K. Lumniczky, S. Désaknai, S. Trajcevski, E J. Hidvégi, H. Hamada, G. Sáfrány. Detailed characterization of the mouse glioma 261 tumor model for glioblastoma therapy. Cancer Science, 97.546-553. 2006).

To follow tumor growth the diameters of subcutaneous tumors were measured in 3-4 days intervals with calliper and tumour volume was calculated as length×width×height×π/6. Mice were killed when they were moribund. All mice were carefully autopsied.

The animal studies were done according to Hungarian regulations under the permission of the Institutional and National Body of Animal Care and Testing. All treatment groups composed of 5 mice.

9.2.2. Combined Treatment of Subcutaneous Tumors with MTH-68H/VB, Local Tumor Irradiation and Temodar Tumor treatment started 7 days after tumor cell implantations. The following modalities were applied in various combinations:

1. Daily local tumor injections of MTH-68H/VB ($1\times10^7$ viral particles/injection in 50 μl final volume) for 2 weeks (total 10 injections, 5 injections/week). In the combined protocols MTH-68H/VB injection was applied immediately after irradiation and/or Temodar (100 mg temozolomide/capsule, Schering Corp. Kenilworth, N.J. 07033.) treatment. The capsules were opened by sterile blades and the content suspended in 2.5 ml dimethyl-sulfoxide by sonication. After sonication the final volume of the homogenous suspension was adjusted to 20 ml by PBS resulting in 5 mg/ml final Temodar concentration. This solution was stored at 4° C. for 3-5 days 2. Intraperitoneal (ip) Temodar injection (100 mg Temodar/1 kg body weight) for 3 consecutive days.
3. Radiation treatment was done on three consecutive days. The tumor-bearing right limb of anaesthetized mice was irradiated with 2 Gy X-rays (THX-250 Therapeutic X-ray Source, Medicor, Budapest, Hungary, dose rate: 1.003 Gy/min). When tumor irradiation was combined with Temodar treatment, irradiation was performed 1 h after chemotherapy.

Two different treatment schedules were applied. In the first protocol, tumors were induced with the subcutaneous injection of $1 \times 10^6$ GI261 cells. Tumors were palpable (about 1-2 mm tumor diameter) after one week. In the second protocol, tumors were induced with the subcutaneous injection of $2 \times 10^6$ GI261 cells. Tumors were clearly palpable (about 3-4 mm tumor diameter) after one week.

Schedule I Treatment Groups (5 Mice/Group)
 Group 1—untreated controls
 Group 2—mock (PBS) treated controls
 Group 3—MTH-68H/VB treatment ($1 \times 10^7$ MTH-68H/VB injection for 10 days)
 Group 4—local tumor irradiation with 3×2 Gy
 Group 5—MTH-68H/VB (10 days)+irradiation (3×2 Gy)
 Group 6—intra-peritoneal Temodar treatment (3×)
 Group 7—MTH-68H/VB (10 days)+Temodar (3×)
 Group 8—MTH68H/VB (10 days)+irradiation (3×2 Gy)+Temodar (3×)

Schedule II Treatment Groups (5 Mice/Group)
 Same as protocol I, except that Group I was treated with 10 intraperitoneal injections of MTH68/H/VB Results In the first set of experiments small tumors were treated. The mock treatment with intratumoral PBS injections resulted in the same tumor growth as detected in the untreated tumor bearing mice (FIG. 25).

The intratumoral injections of MTH-68H/VB clearly slowed down tumor progression. Slightly stronger antitumor effect was observed after single agent treatments of Temodar and local tumor irradiation. Combination of MTH68/H/VB either with Temodar or irradiation was superior to single agent protocols. Very strong antitumor effect was observed after combined treatment with Temodar and tumor irradiation which was further improved by local intratumor injections of MTH-68H/VB (FIG. 27).

In the second set of experiments bigger tumors were treated with the antitumor combinations mentioned above. There might be two possibilities to explain the antitumor effect of MTH-68H/VB. One of them is the direct cytotoxic effect of the virus. It is also possible that the virus induces an antitumor immune attack. To test the second option tumor bearing mice were treated by intraperitoneal MTH68/H/VB injections. Contrary to the result of the first experiment intratumor MTH68/H/VB treatment did not stop tumor progression (FIG. 28).

Temodar treatment alone resulted in a moderate tumor growth inhibition. However this was further improved when combined with intratumoral MTH68/H/VB injections. Radiation treatment alone suppressed tumor growth. Notably the combination of MTH68/H/VB viral application with radiation treatment was clearly superior to radiation alone. This combination was superior to that seen in the combination of tumor irradiation with Temodar treatment. The strongest tumor growth suppression was observed when all three agents were applied (FIG. 28).

Conclusions

Intratumor injections of MTH-68H/VB injections slowed down tumor progression when the tumor volume was small.

Our data demonstrates that MTH-68H/VB treatment can be powerfully combined with local tumor irradiation. The antitumor effect of the combined MTH68/H/VB and radiation treatments is similar to the combined effect of Temodar and tumor irradiation. The great advantage of using MTH68/H/VB—in combination with radiation therapy is that MTH68/H/VB as a viral therapy is non-toxic even when given over long periods of time, especially at the low doses most likely necessary to see efficacy with the potent strain MTH-68/H/VB, while the efficacy of the chemotherapy treatments is seriously affected by its short and long term toxic side effects.

MTH-68/HVB treatment also enhances the tumor growth inhibitory potential of Temodar, thus rendering it to be a highly useful adjunct to the standard cancer treatment.

The most dramatic therapeutic effect was observed when all three agents, MTH-68H/VB virotherapy, chemotherapy, and radiation were applied in close combination. These findings are especially significant with the increasing incidence of, and the unrelenting lethality of gliomas—in particular glioblastomas, which have the most fatal and deadly of outcomes of all cancer types.

9.3. Combined Treatment of Subcutaneous Tumors with MTH-68H/VB, Local Tumor Irradiation and BCNU In this study the effect of the MTH-68H/VB treatment and/or irradiation was studied on the antitumor activity o BCNU. BCNU (active ingredient: Carmustine, common names: BCNU, BiCNU, Carmustine, classification: alkylating agent, nitrosurea). BCNU was utilized as a single treatment chemotherapy for many years on primary brain tumors and has played a significant role for more than 30 years in standard chemotherapy for glioblastoma multiforme.

Tumor treatment started 7 days after tumor cell implantations. The following modalities were applied in various combinations:

1. Daily local tumor injections of MTH-68H/VB ($1 \times 10^7$ viral particles/injection in 50 µl final volume) for 2 weeks (total 10 injections, 5 injections/week). In the combined protocols MTH-68H/VB injection was applied immediately after irradiation and/or BCNU treatment.
2. Intraperitoneal (ip) BCNU treatment.
3. Radiation treatment was done on three consecutive days. The tumor-bearing right limb of anaesthetized mice was irradiated with 2 Gy X-rays. When tumor irradiation was combined with BCNU treatment, irradiation was performed 1 h after chemotherapy.

In the protocol, tumors were induced with the subcutaneous injection of $2 \times 10^6$ GI261 cells. Tumors were clearly palpable (about 3-4 mm tumor diameter) after one week.

Schedule I Treatment Groups (5 Mice/Group)
 Group 1—untreated controls
 Group 2—mock (PBS) treated controls
 Group 3—MTH-68H/VB treatment ($1 \times 10^7$ MTH-68H/VB injection for 10 days)
 Group 4—local tumor irradiation with 3×2 Gy
 Group 5—MTH-68H/VB (10 days)+irradiation (3×2 Gy)

Group 6—intra-peritoneal BCNU treatment
Group 7—MTH-68H/VB (10 days)+BCNU
Group 8—MTH68H/VB (10 days)+irradiation (3×2 Gy)+ BCNU BCNU treatment alone resulted in a moderate tumor growth inhibition. However this was further improved when combined with intratumoral MTH68/H/VB injections. Radiation treatment alone suppressed tumor growth moderately. Notably the combination of MTH-68H/VB viral application with radiation treatment was clearly superior to radiation alone. This combination was superior to that seen in the combination of tumor irradiation with Temodar treatment. The strongest tumor growth suppression was observed when all three agents were applied (FIGS. 29 and 30).

Interestingly, the intra-tumor MTH-68H/VB injections prevented the outgrowth of the tumors in a few animals (FIG. 30). Note, that the tumor growth curve at the beginning shows the average volume of five tumors per treatment group. The sudden drop in the tumor volume represents that one or two of the large tumor-bearing, moribund mice were killed by anesthesia for ethical reasons. The end of some of the lines in FIG. 29 before the 50$^{th}$ day indicate that all animal were lost in the group. The return of the tumor growth curve to the near baseline represents mice cured from the tumor by the treatments (FIG. 30). The survival of tumor bearing mice is shown.

Conclusions

Our data demonstrates that MTH-68H/VB treatment can be powerfully combined with local tumor irradiation and chemotherapy. The great advantage of using MTH-68H/VB—in combination with radiation therapy is that MTH-68H/VB as a viral therapy is non-toxic even when given over long periods of time.

MTH-68/HVB treatment also enhances the tumor growth inhibitory potential of BCNU treatment.

The most dramatic therapeutic effect was observed when all three agents, MTH-68H/VB virotherapy, chemotherapy, and radiation were applied in close combination. These findings are especially significant with the increasing incidence of, and the unrelenting lethality of gliomas—in particular glioblastomas, which have the most fatal and deadly of outcomes of all cancer types.

It has to be understood that the experimental data provided in section 9 of this application are examples for NDV clones according to the invention. They are supposed to describe the specific properties of these clones by way of examples without any limitation to the specific clones being used.

10. Use of MTH-68H/VB for Medical Treatment

The NDV clones according to the invention may be used for the treatment of neoplastic disease. Treatment may be defined as:
1—causing tumor regression, regression can be defined as decreasing of tumor size, as can be objectively measured using physical examination or known imaging techniques, including space occupying lesions, as well as other, for example as in, but not limited to hematologic disease, for example in leukemia a decrease in malignant cells, or as manifested in metastatic disease.
2—the co-application of MTH-68/HVB viral clone with other cancer treatment modalities, including but not limited to chemotherapy and radiation, in order to allow synergistic enhancement of their respective anticancer properties,
3—the co-application of MTH-68/H-VB viral clone with other cancer modalities to diminish negative side effects—including but not limited to nausea, vomiting, hair loss, fatigue, loss of appetite-, or radionecrosis
4—the relief of cancer related pain, especially but not limited to pain caused by metastastic disease and or space occupying lesions; consequently lessening the need for pain medications—as in codeine, and or morphine,
5—the treatment of terminal cancer patients who have exhausted all traditional treatment modalities where tumor regression may still be expected secondary to viral treatment, with expectation of prolongation of life
6—in order to enhance the cancer patient's or terminal cancer patient's quality of life by relief of their tumor related symptoms even in the absence of direct evidence of tumor regression. Tumor related symptoms may be defined as fatigue, pain, loss of appetite (the extreme form manifested as cachexia), decreased energy, decreased sense of wellbeing, loss of libido.

Cancer types that might successfully be treated using a pharmaceutically acceptable formulation of the clones described herein include but are not limited to cervical cancer, ovarian cancer, bladder cancer, renal carcinoma, Wilm's tumor, prostate cancer, lung cancer (including bronchial), lymphoma, leukemia, central nervous system tumors (including meningeoma, medulloblastoma, glioblastoma, astrocytoma, neuroblastoma); pancreatic cancer, skin cancer (incl. melanoma), colon cancer, bone (both primary and metastic lesions) and breast cancer, stomach cancer, esophageal cancer, thyroid cancer, sarcomas, mesothelioma, head and neck cancers (including oro-naso-pharyngeal, parathyroid), hematological malignancies, vulvar, vaginal, endometrial carcinomas, testicular carcinoma, ano-rectal cancers, hepatic and extrahepatic (bile duct) cancers, sarcomas (including Ewings), eye cancer (including retinoblastoma), thymic carcinoma, urethral cancers, carcinoid tumors and adrenocortical cancers, as well as the metastatic lesions as a result thereof, and the paraneoplastic symptoms and debilitating states which are a consequence of the advanced stages of but not limited to the above listed neoplastic conditions.

In an advantageous embodiment of the invention, a potent oncolytic viral clone is administered therapeutically to treat cancer.

The manufacturing and purification steps described below are those which assure the ability to guarantee a contaminant free, pure, non-allergenic, standardized, homogenous, stable, temperature resistant robust, transportable, practical, user friendly—viral therapeutic product for the purpose of treating human diseases, especially cancer and its accompanying or resultant symptoms, alone or as an adjunct to other forms of therapy, and one which is then adaptable to various routes of administration—including but not limited to parental administration, with the preclusion of and removal of any contaminating presence, including possible allergenic entities such as egg proteins derived from the inoculated eggs themselves—The following method for manufacturing and purification and freeze drying has successfully been applied:
   I. Generating a purified clonal viral clone (e.g. through multiple plaque purification)
   II. Inoculating Specific Pathogen Free (SPF) chicken eggs with the clonal clone
   III. Incubating the SPF eggs
   IV. Chilling the SPF eggs
   V. Harvesting the allantoic fluid from the SPF eggs
   VI. Removing-debris from the allantoic fluid—possibly using filtration and or centrifugation
   VII. Ultracentrifugation of the Allantoic Fluid VIII. Formulating and Filling Individual Containers
IX. Lyophilization- and Freeze Drying of Finished Product
X. Quality control testing, and the methods to make this possible, including neutralization of the clone, and the use of cell lines, animal models, and PCR.

The expert skilled in the art is aware of alternative ways to manufacture and purify the egg derived viruses. (Further details of virus manufacture and purification may be found in: Vaccine Manual. The production and quality control of veterinary vaccines for use in developing countries, FAO Animal Production and Health Series, 1997; Newcastle disease vaccines, their production and use, FAO Animal Health Series No 10, 1978; Development in Veterinary Virology: Newcastle Disease: 1988. Edited by D. J. Alexander, Kluver Academic Publisher).

For the purpose of medical treatment the virus clone is formulated as a pharmaceutical preparation by bringing it to a standardized dose form together with stabilizers, such as starches, and or sugars—so as to make it a stable product. The product is further freeze dried to ensure its relative thermostability, and contained in individual vials, containing specific dosages, hence making it transportable, and amenable not only to be used in hospital settings but also amenable as a therapeutic to be used in out-patient settings. This allows for increased economic viability and makes the treatment more accessible as a long term treatment, which is especially significant in the case of maintenance therapy and prevention. Outpatient therapy allows for long term patient compliance, and enhances its economic viability.

For the purpose of medical treatment the virus clone will be applied as follows: Because of its potency, an NDV clone according to the invention, such as MTH-68/H/VB, can be administered effectively not only parentally—invasively but can also be therapeutically efficacious applied using a non invasive route of administration—i.e. for example as in droplet, spray, sublingual or aerosol form using a nebulizer.

Depending on the route of administration the dosaging may change—the therapy may be efficacious already at a dose of $10^7$ to $10^9$ viral particles/per dose per day—which may be administered in a single dose or multiple times per day. The dosaging may be increased, and may be proven to be efficacious given in multiples of the single dosage, e.g. 2 times, 5 times or even 10 times of $10^7$ to $10^9$ viral particles/per dose, or alternatively doses may be administered several times a day; or it may be that a higher loading dose is administered in the beginning of a therapeutic cycle, i.e. for example in the first weeks to months, followed by lower doses or can eventually be decreased in dosage by administering the viral particles/vial with less frequency, i.e. substituting a multiple daily dosaging schedule to once a day; or shift from a daily dosage to administration every other day. Typically the virus according to the invention is provided in vials with a standardized amount of virus particles per vial, such as e.g. $1\times10^7$, $2.5\times10^7$, $5\times10^7$, $1\times10^8$, $2.5\times10^8$, $5\times10^8$, $1\times10^9$, $2.5\times10^9$, $5\times10^9$ or $1\times10^{10}$ virus particles/vial. Depending on the dosage protocol a predetermined number of vials is applied to the patient at a certain point in time. The usual therapy is based on the application of one standard dose daily (for example $1\times10^8$ or $1\times10^9$ virus particles per day). Usually the standard dose is provided in a single vial which is applied once daily. However, for a variety of reasons there may be circumstances in an individual which requires the application of a higher or a lower dose. The individual dosage can be adapted to such individuals according to methods known in the art. A patient could e.g. receive two or three standard doses a day when higher doses are needed. A patient could also receive a standard dose every other day or once a week or even once a month when lower doses are needed. The standard does could also be infused over a period of time as opposed to bolus application. The expert in the art may adapt the dosage protocol according to the requirements of the individual (especially the particular disease and the progress thereof) in connection with the application mode. The therapeutic dosage protocol is initially determined and adjusted depending on the particular tumors type's sensitivity to virotherapy—and may be further adjusted according to the patient's clinical response—the original dosage may eventually be tapered. After the desired therapeutic effect is seen it may be efficacious to continue on a maintenance schedule with a weekly or even bi-monthly or monthly dosing schedule over a prolonged period of time. Even long term maintenance therapy over years is possible and has no known contra-indication as in cumulative toxicity.

Because of its efficacy; the relatively low MTH-68/H/VB individual dose necessary to result in therapeutic effect on sensitive tumor types with the significant possibility of being able to apply the treatment using a non-invasive routes of administration, makes the treatment particularly amenable to out-patient therapeutic settings as well as increasing long term patient compliance. Because of the relatively low dosage needed for a beneficial therapeutic effect to be observed, the patient need not go through a desensitization treatment schedule as seen in other high dose intensive NDV intravenous—viral cancer treatments where much higher dosages have been applied.

A long term form of therapy vs. only acute intervention allows MTH-68/H/VB, as well as possible other forms of viro-therapy, to be used as a preventative form of biological cancer therapy, destroying nascent or residual cancer cells, thus decreasing the risk of reoccurrence, as well as decreasing the risk of the development of metastatic lesions, indeed eventually MTH-68/H/VB viro-therapy and other viro-onco-therapies may be used as a form of preventative therapy in patients identified to be at high risk for the occurrence of specific viro-sensitive types of tumors (e.g. by genetic testing).

The virus administration can be provided by different methods and routes of administration; by way of inhalation intravenous, intra-arterial, enteral, parenteral, intrathecal, intraperitoneal, intrathoracic, intrapleural, oral, sublingual, bucco-mucosal, intranasal, intracystic, inraurethral, rectal, vaginal subcutaneous, intratumoral, peritumoral, local, intramuscular, intrabronchial, intrarterial, intracranial, and/or topical application or by any other way. The viral clone may be delivered by way of endoscopy or catheter or nebulizer or dropper or syringe or spray or other technical aids needed for efficient therapeutic delivery For patients who require long term or maintenance intravenous treatment this may include delivery through a central venous catheter (Hickman, Neostar, Broviac for example) or for direct tumoral delivery of virus an arterial catheter may be required. Some patients may eventually benefit from trans-dermal delivery by way of dermal patches.

The virus clone may be delivered in bolus form over a short time, or in infusion form over several hours, or in the case of oro-buccal-sublingual or intranasal administration may be delivered by way of droplets or in spray or in aerosol form, using a nebulizer, particularly in the case of lung, or bronchial tumors. In case of rectal or vaginal administration a suppository form of administration may be used.

Another aspect of the invention is a combination therapy using the virus according to the invention in combination with one or more chemotherapeutic agents. It can be used both as a potentiating adjuvant agent employing the synergistic cell killing effect between viral therapy and chemotherapeutic agents. Possible chemotherapeutic agents include alkylating agents, anti-metabolites, anti-tumor antibiotics, topoisomerase inhibitors, mitotic inhibitors, targeted therapies, differentiating agents or others. Examples for such chemotherapeutic agents include but are not limited to arsenic trioxide, adriamycin, BCNU, bexarotene, bleomycin, carboplatin, cisplatin, decarbazine, doxorubicin, 5-fluorouracil, methotraxate, taxol, temozolomide, vinblastine, vincristine. Further embodiments include azacitidine, azathioprine, capecitabine, chlorambucil, cyclophosphamide, cytarabine, daunorubicin, docetaxel, doxifluridine, epirubicin, epothilone, etoposide, gemcitabine, hydroxyurea, idarubicin, imatinib, mechlorethamine, mercaptopurine, mitoxantrone, oxaliplatin, paclitaxel, pemetrexed, sorafenib, teniposide, tioguanine, tretinoin, valrubicin, vindesine, vinorelbine, imitanib, gefitinib, erlotinib, sunitinib, bortezomib.

In such an administrative modality the virus may be administered concurrently with the chemotherapeutic agent as in within the same therapeutic regimen, even within the same day anywhere between twenty minutes and twenty-four hours; or it may be administered at different points in time, such as before the beginning of or after the completion of a chemotherapeutic cycle (measured in days or weeks) preceded or followed by a viral therapeutic course of therapy, or it may be administered intermittently, punctuating the chemotherapeutic regimen. In another embodiment of the invention the virus may be administered simultaneously along with the chemotherapeutic agent, by any of the aforementioned routes of administration i.e from being administered nasally (spray or droplets); or sublingually, or intravenously, or it may be administered to a target location (for example intratumorally).

MTH-68/H/VB can also be considered as an adjuvant therapy when confronted with a large inoperable or irradiable tumor. Chemotherapy is sometimes used with the intent to diminish the size of a tumor so that it may be rendered surgically removable or better circumscribed for radiation therapy. It is possible that MTH-68/H/VB can diminish or eliminate metastatic lesions thus making the patient a candidate for surgical therapy of the large primary lesion, placing him/her in the category of operable vs. being considered inoperable. Thus the use of MTH-68/H/VB therapy may also be considered an adjuvant therapy to possibly curative surgical procedures.

Another embodiment of the invention is the application of the virus in combination with radiotherapy. In such case the tumor may receive radiation ($\alpha$, $\beta$ or $\gamma$-radiation, X-ray-radiation, particle-radiation such as proton-radiation applied in the following manners but not limited to external beam radiation, endo-cavitary radiation therapy, interstitial radiation, or brachytherapy or others).

In such an embodiment the radiation may be applied first—thus sensitizing the tumor cells, and subsequently the virus may be applied. A full cycle of radiation therapy may be applied, and may be followed by MTH-68/H/VB therapy. However, under certain circumstances it might be advantageous to first apply the virus and subsequently apply radiation to the tumor. Or the synergistic effect may also be seen when both modes of therapy are applied simultaneously—in parallel. It may also be beneficial to add MTH-68/H/VB to a regimen where Chemotherapy and Radiotherapy are given in conjunction with one another—as is done for example in advanced head and neck cancer, either simultaneously—concurrently, or in tandem—one treatment cycle following the other. Chemotherapy is often given at the same time as radiation to render the radiation therapy more effective. The chemotherapy may be given in a variety of ways, including a low daily dose, a moderately low weekly dose, or a relatively higher dose every three to four weeks. When using this potentiating treatment regimen MTH-68/H/VB could possibly be given at the same time as the chemotherapy, or before or after it. As has been noted in the data garnered from our research the combination of all three modes of therapy has been proven to have an extreme positive synergistic therapeutic effect—in experimental animal studies; leading to a high percentage of cure (as opposed to partial remission). It has been further shown that even a single or limited amount of exposure to a therapeutic dose of radiation followed by chemotherapy and viral therapy can greatly sensitize the tumor cells to allow for increased efficiency of the chemotherapy in conjunction with virotherapy.

As opposed to treatment with other strains of NDV the patients treated with the clone according to the invention show dramatically less symptoms of pain. While this has been noted as a minor characteristic in prior publications, it is found with MTH-68/H/VB to have prominent importance, and is highly significant. This is an improvement over other cancer therapies, where the patient's pain is not directly addressed, even those treatments based on other viral applications. This effect of MTH-68/H/VB is especially noted in bone cancer, which is typically associated with a high degree of pain and suffering. Typically bone cancer patients need to receive high amounts of pain killers, such as morphine, in order to alleviate their pain, which while masking the pain to some degree, never completely alleviates it, and as is well-known all such narcotics carry with them the problem of eventual tolerance, leading to the need for increased dosages to arrive at a therapeutic effect, and as is well known high dose narcotics even with cancer associated pain killers carry with them side effects, including increasing tolerance, leading to possible subsequent dependence, leading to diminished therapeutic effectuality, while increasing the lethal risk. Therapy with MTH-68/H/VB viral therapy according to the invention significantly lowers the perception of pain in cancer patients. Many patients can significantly lower their pain medication intake, or some patients even can stop the use of pain medication all together.

Patients have also been observed to have significant improvement of clinical symptoms, when undergoing treatment with viral therapy as described in the invention, as reflected in quality of life—i.e. tumor related symptoms of but not limited to—severe anorexia, loss of energy, depression, inertia, nausea, fatigue, which manifests itself in most cancer patients at a certain point in the clinical course of their disease. The amelioration in quality of life in patients using MTH-68/H/VB Virotherapy has been observed in even advanced cancer patients, who are no longer eligible for other traditional modalities, and or even where objective tumor regression may be limited, is no longer obtainable, or even expected, or not readily observed, even such patients may have a marked and significant improvement in life style, and quality of life besides the objective prolongation of life as expressed in increased expected survival time, with the addition of MTH-68/H/VB viral therapy to their therapeutic regimen. Thus according to the invention, MTH-68/H/VB can be a candidate of treatment even in patients who are at advanced stages of disease beyond the hope of long term remission—allowing them to have increased functionality and quality of life in the presence of advanced neoplastic disease.

A further aspect of the invention is the significant alleviation of the expected side effects observed as a result of chemotherapy, especially the high dose chemotherapy sometimes required for efficacious curative treatment necessary for certain types of cancer, as for example used in pediatric hemo-oncological settings. The side effects potentially avoided are—but not limited to—nausea and vomiting, extreme fatigue, intestinal problems, and loss of appetite and weight changes, The same has been observed of combined viro-treatment with radiation therapy—as in alleviation of the most ubiquitous—prevalent side effects such as fatigue, and anorexia.

This surprising effect of MTH-68/H/VB could possibly allow a patient to undergo these toxic and exquisitely trying forms of cancer treatment with considerably less morbidity and discomfort than would be normally expected. Potentially this would render patients more compliant, besides allowing them to resume normal daily activities even while undergoing traditional modes of cancer treatment, thus diminishing the potential financial and emotional burden of inactivity and acute disability, often seen in patients undergoing these forms of cancer treatment. A further aspect of the invention is the possible radio-protective role MTH-68/H/VB may have to radio exposed cells—organs, as well as having a healing role; thus preventing or even promoting the healing of both the short and long term side effects of radiotherapy. While radiotherapy's acute side effects usually are transient in nature, as in the symptoms described above, as in fatigue, and anorexia, which manifest themselves during the radiation therapy itself, it may also cause acute short term changes locally, as for example skin changes, or other acute symptoms depending on the exposed organs the range of severity of which may greatly vary in degree, such as, but not limited to diarrhea, incontinence, painful urination, frequency in urination, difficulty in swallowing, dryness of the mouth, tenderness, ulceration, cough, shortness of breath, sore throat, hoarseness. These symptoms are caused by the local pathological effect of radiation on the tissues of the organs involved-causing for example an inflammatory response, dry and moist desquamation, or early necrosis. There are also symptoms of long term sequelae, which while not as common, effecting approximately 10% of treated patients, may lead to severe long term debilitation, often either as a result of the above type changes not resolving over time, becoming chronic, or long term sequelae which may appear weeks-to months to even years after radiation exposure. The long term effects of radiation exposure may lead to the detriment of the exposed organs possibly leading to even an irreversible process with oft fatal outcome, as for example in the treatment of CNS tumors as in tumors of the brain or spinal cord, resulting in radio-necrosis of the brain tissue or severe spinal cord damage. Other examples of long term sequelae are for example soft tissue necrosis, as seen in oro-pharyngeal interstitial radio-treatments, osteo-radionecrosis as seen in the necrotic changes of the mandible-jaw, or long term side effects seen in skin lesions such as—subcutaneous fibrosis, atrophy, telangiestasia, chronic necrosis, unresolved ulceration, and as seen for example in radiation treatment of head and neck cancers—stricture formation, leading to difficulty in swallowing or severely decreased saliva formation—xerostomia—leading to severe difficulty in chewing, swallowing, caries formation, Or local myelopathies may develop in exposed muscle tissue, or chondro-necrosis as seen in the cartilaginous damage of radiation to the larynx, or ulceration or stricture of the esophagus, leading to dysphagia, and inability to swallow. Radiation to the lung can lead to fibrosis, and, or pneumonitis, long term sequelae of colon radiation treatment can lead to chronic irritation of the bowel, or rectum causing chronic diarrhea and discomfort, to causing actual obstructive strictures needing surgical intervention.

The above described sampling of potential short and long term side effects of radiation therapy seriously effects the maximum doses considered to be safe—having direct practical consequences in limiting the possible curative or therapeutic radiation doses prescribed in any course of radiation therapy—, thus imposing severe limits to radiation's therapeutic dosing; when considering the medically therapeutic risk benefit ratio.

Co-application of or preceding with or following radiation therapy with MTH-68/H/VB virotherapy may not only cause a synergism of the tumor cell killing qualities of both types of therapy as previously described—it may also be that MTH-68/H/VB virotherapy not only has a cyto-protective effect on healthy cells, thus making radiotherapy safer and more tumor cell selective. Beyond this MTH-68/H/VB may actually promote the healing of radio exposed healthy non-tumorous cells, through its cytoprotective mechanism, as observed in the healing of the long term sequelae of necrotic ulcerative mucosal tissue seen in post radiation treatment of head and neck cancers by possibly applying MTH-68/H/VB locally intra-orally, to the effected mucosal membrane.

The present invention may also be used for example in radiation necrosis due to the intense radiation therapy often demanded in their treatment. Often radiation necrosis can be mistaken for new tumor outgrowth, indeed it is difficult to differentiate, as the ongoing expanding process of radiation necrosis can mimic a space occupying lesion leading to fatal consequences. It may be in such a case that MTH-68/H/VB be administered and as such lead to an avoidance of a fatal consequence.

11. Examples

The present invention is further illustrated in the following examples which do not limit the invention in any way.

Example 1

Manufacture of Clone

Preparation of the MTH68H/VB Master Seed

The MTH68-H/VB master seed was derived from the single unique plaque that had been chosen during the plaque purification of the parent stock.

The master seed is propagated in embryonated chicken eggs obtained from an SPF flock. Rigorous testing of the master seed revealed no evidence of contamination with aerobic or anaerobic bacteria, mycoplasmas, fungi or viruses other than Newcastle disease virus. The allantoic fluid was diluted with a non-skim milk based virus protective solution and freeze dried in glass ampoules.

Production of the MTH68H/VB Trial Formula

Remove and thaw an aliquot of reconstituted master seed from the −70° C. freezer. Further dilute the thawed virus suspension to ensure each egg receives at least 0.1 mL inoculum of the diluted virus suspension of which titre is $10^{3°}$ $EID_{50}$, preferably $10^{5°}$ $EID_{50}$ per 1.0 mL ($EID_{50}$ determination is carried out according to methods described in the art).

The 9 to 11 days old, preferably 10 days old SPF chicken embryos are inoculated with 0.1 mL of the diluted virus seed into the allantoic cavity according to the regular method.

After 24 hours of incubation the eggs are candled and the dead embryos are discarded.

After 4 days of incubation, the embryos are removed from the incubator and chilled for at least 2 hours, preferably overnight.

The allantoic fluid is harvested from the eggs into sterile containers preferably that can be centrifuged.

After sterility testing the virus suspension is pooled and pre-purified by centrifugation, then Concentration and further purification is made by ultracentrifugation.

The preparation of aliquots in sterile containers helps to prepare the prober amount suitable for one full load of the freeze-dryer.

Store at −70° C. till further processing.

The next step is the production of the freeze-drying bulk that consists of the purified virus suspension with the required, preferably $10^{9.2}$ $EID_{50}$ per 1.0 mL and the protective agents.

The virus mixed with the protective agent is freeze dried.

For purposes of mass production of pharmaceutical preparations of NDV viruses the bulk product may be freeze-dried and the resulting cake may be divided and filled in individual containers.

Example 2

Formulation of Clone

The MTH68-H/VB containing virus suspension is freeze-dryed in sterile glass vials and closed with rubber stopper. Before the dissolution of the lyophilized virus containing cake with sterile saline solution, the rubber stopper should be disinfected.

One mL of sterile saline solution is introduced to the vial to get the final formulation of the product ready for use.

Example 3

Treatment of Patients

Case Study A—Pain—Prolonged Life Expectancy—Quality of Life—Side Effects.

An elderly Female Patient who was diagnosed with Stage Four Breast Cancer—three years prior—and over the years had undergone several cycles of multiple chemotherapies, as well as having been treated with local radiotherapy and oral pain medications for her widespread painful metastasis to the bone—including metastatic lesions found in the vertebrae, femur, and pelvis, suddenly had a worsening of her clinical status with anorexia, weight loss—weakness—becoming bedridden, unable to sit up, with a persistent cough and severe dyspnoea which needed continuous supplemental oxygen. She was diagnosed with metastatic lung lesions. The patient was told that she was no longer eligible for any further oncological treatment. She was referred to hospice care, prescribed oxygen and morphine with a short expectation of survival time. The patient began MTH-68/H/VB therapy, which she received on a daily basis up to six times a day using one vial per administration containing $10^8$ viral particles per vial via nasal droplets using a nasal spray. Within one week of viral treatment her cough diminished, eventually to resolve altogether. She became stronger so that once able to sit up received viral delivery intermittently using an inhalatory nebulizer containing $10^8$ viral particles per administration. She eventually became fully ambulatory with the help of a walker. She no longer needed oxygen. Her appetite returned, she ate meals with pleasure and gained weight. She no longer needed the prescribed amounts of pain medication for her metastatic bone pain. A month later the patient returned for a follow up X-Ray, which showed that she had no metastatic lesions in the lung. Two months later her physician considered her to be again eligible for another round of chemotherapy. She was started on a low dose of oral chemotherapeutic treatment. She continued viral therapy as described above decreasing the daily dosage of $10^8$ viral particles to two to three times a day, administered either via nasal droplets or nebulizer. The patient continued to have a good appetite, with no experience of nausea, or fatigue. She remained ambulatory, resumed physical therapy and had a high quality of life. She experienced no further pain or discomfort from her metastatic bone lesions, allowing her to stop all pain medications altogether. While on bone scan her metastatic bone lesions did not resolve—there was no sign of further progression. A year later the patient died suddenly of a stroke. She had recently been taken off her prophylactic daily dose of Coumadin (advanced metastatic conditions carry with them a high risk of hyper-coagulation)—, which she had taken continuously since her initial Stage IV diagnosis—four years earlier.

Case Study B—Chemotherapy-Side Effects—Prolonged Life Expectancy—Quality of life.

Patient was a middle-aged male who was diagnosed with bladder cancer. Pathology confirmed a high grade transitional cell carcinoma, which had invaded the muscle wall and there was found to be significant lymph node involvement. He was diagnosed as Stage IV. Post surgery the patient received an aggressive regimen of combination chemotherapy. However due to significant side effects—including a dangerously low WBC the patient could not complete the full course of chemotherapy. A few months later imaging studies revealed that the patient had new inoperable pelvic masses. The patient was informed that he had a limited survival time of less than two years. He was offered a palliative regimen of a chemotherapeutic protocol. After commencing chemotherapy the patient concurrently began MTH-68/H/VB adjuvant viro-therapy, using intravenous application of $10^8$ viral particles per dose one time a day. The patient immediately remarked a dramatic diminishment of all chemotherapeutic side effects—allowing him to resume his previous athletic life style—including sailing and horseback riding—all the while continuing with his chemotherapeutic treatment. The patient was able to complete the prescribed chemotherapeutic regimen which now caused him minimal discomfort. After its completion a follow up CT showed a decrease in the size of his pelvic masses, until almost a year later no sign of metastatic disease was noted. He stopped MTH-68/H/VB viro-therapy. Over a year later the patient was again found on CT to have pelvic masses, at which time he again followed a course of chemotherapy and again added MTH-68/H/VB viro-therapy as an adjunct. In the manner described above. He again experienced no side effects from the chemotherapy. Upon completion of the chemotherapeutic regimen he continued to use MTH-68/H/VB virotherapy switching to a daily sublingual application of $10^{7.4}$ viral particles per dose and remains symptom free.

Case Study C—Radio-Necrosis

A middle aged female patient was diagnosed with squamous cell carcinoma of the oral cavity. Only local involvement was discerned with no metastatic lesions. She was diagnosed as Stage II. The patient underwent ablative surgery, but received no chemotherapy. The patient received post-surgical intensive radiation therapy. After the radiation she had dysgeusia, ulceration, pain, and bleeding, symptoms of mucositis, which also affected her speech, and her ability to eat or drink or to take oral medication, leading her to use only a straw and lose significant weight. Her symptoms continued for over six months with no relief, and it became evident that what was hoped to have been a transient acute condition was chronic injury due to radio-necrosis. The patient also had major dental extraction leading to significant cosmetic disfigurement. The patient began local oral therapy with MTH-68/H/VB of $10^{8.7}$ viral particles/per application twice a day, applied as a mouth wash, as well as administering MTH-68/H/VB of $10^{8.7}$ per once a day application using an intranasal spray. After one week of daily treatments her symptoms began to abate, and after one month she no longer felt discomfort, no longer had bleeding or pain, and was able to take oral nutritional intake. While her mucosal membrane had healed, she was still not considered a candidate for post therapeutic dental implants due to the irreversible mucosal damage. However the patient no longer suffered from pain or discomfort.

Case Study D Radionecrosis

A 12 year old male presented with a large brain mass. The tumour was widely surgically debulked. Pathology considered the diagnosis to be Glioblastoma Multiforme. The patient received a full course of intense focal radiation. The patient's condition remained stable and he received no further therapy. 9 months later the patient presented with persistent headache. MRI revealed a reoccurrence of tumour. Patient began intensive chemotherapy, but during the therapy his tumour enlarged relentlessly. He continued to rapidly deteriorate clinically, over the next five months with increasing peripheral weakness and aphasia, to the point of becoming bedridden. He was told he had a short time to live, and all therapy was ceased, but for i.v. steroids to palliatively treat the prominent brain oedema. Upon review of the MRI the possibility that the image actually reflected chronic radionecrosis, as opposed to active tumour was considered, as similar images can sometimes be seen in radio-necrosis which is often difficult to differentiate from tumour. Because of the spreading and space occupying character of radio-necrosis within the closed confines of the bony structure of the skull, post necrotic radio-necrosis in brain tumours can be fatal. However, because of the clinical condition of the patient and the lesion's location no biopsy was able to be done. The patient began daily iv MTH-68/H/VB $10^{7.4}$ per dose of up to three applications a day. The patient's clinical condition improved and his "tumour" began to diminish in size within the first six months of treatment—until 1 year later it had disappeared all together. The patient remains on a maintenance schedule of viro-therapy of $10^{8.0}$ viral particles per dose, applied once a week using a nebulizer. While unable to prove the existence of radio-necrosis as opposed to GBM, the patient's dramatic and rapid improvement and seemingly curative remission led some oncologists to question the initial GBM diagnosis and seriously consider the condition to reflect radionecrosis.

Case Study E Chemo-Therapy—Side Effects.

A young boy presented with a peri-tonsillar node. Biopsy showed B cell non-Hodgkin's Lymphoma. He had no metastatic lesions, and was determined to be Stage I-II. Patient was treated with an aggressive multi-chemotherapeutic modality for four months. Patient was also given a course of regional radiation therapy. Three weeks after discharge a new salivary gland tumour appeared, as well as a reoccurrence of the meso-phayngeal node. The patient's family at this time was told by physicians that there was limited hope of long term survival. Patient began several cycles of aggressive intravenous poly-chemotherapy, and began MTH-68/H/VB viro-therapy concurrently receiving a daily dose by inhalatory application using a nebulizer of $10^8$ viral particles per dosage for the entire year of his chemotherapeutic treatment. The poly and aggressive high dose chemotherapeutic treatment modality applied demanded several hospital stays. What was of note was the patient's ability to under-go the aggressive chemotherapeutic prescribed treatment without the usual nausea anorexia and fatigue, in direct contrast to the other children sharing the same fate on the pediatric ward. Throughout his multiple hospital stays he remained physically active, was markedly playful, and had a good appetite. The therapy was successful; and the patient remained in remission.

The invention claimed is:

1. A purified Newcastle Disease Virus clone comprising the DNA nucleotide sequence of SEQ ID NO: 1.

2. A purified Newcastle Disease Virus clone as deposited with European Collection of Cell Cultures as Accession Number 06112101 on Nov. 21, 2006.

3. A pharmaceutical composition for treating cancer comprising as an active ingredient a Newcastle Disease virus clone according to claim 1 together with physiologically acceptable additives.

4. A purified Newcastle Disease Virus clone according to claim 1 which is freeze-dried.

5. A method of treating human cancer patients comprising an administration to said patients of a therapeutically effect amount of the purified Newcastle Disease Virus clone of claim 1.

6. A method according to claim 5 in which said virus treatment is combined with chemotherapy, radiotherapy, immunotherapy or surgery.

7. A method for treating interferon sensitive neoplastic conditions and non-neoplastic interferon sensitive autoimmune and viral conditions in human patients comprising an administration to said patients of a therapeutically effect amount of the purified Newcastle Disease Virus clone of claim 1.

8. A method, according to claim 7, wherein said interferon sensitive neoplastic conditions are selected from the group consisting of Melanoma, non-Hodgkins Lymphomas, Leukemias, Breast cancer, Bladder Carcinoma, Renal cell carcinoma, Head and Neck cancer, Carcinoid tumors, Bile Duct cancers, Pancreatic cancer, Multiple Myeloma and Kaposi Sarcoma.

9. A method, according to claim 7, wherein said non-neoplastic interferon sensitive autoimmune and viral conditions are selected from the group consisting of Multiple sclerosis, Condylomata acuminata, Hepatitis, Herpes, Rheumatic Arthritis, Behcet's Disease, Idiopathic Pulmonary Disease, Aphthous stomatitis, Severe Malignant Osteoporosis, cervix cancer and SARS.

* * * * *

SEQUENCE LISTING

<160> NUMBER OF SEQ ID NOS: 37

<210> SEQ ID NO 1
<211> LENGTH: 15186
<212> TYPE: DNA
<213> ORGANISM: Newcastle disease virus

<400> SEQUENCE: 1

```
accaaacaga gaatccgtga gatacgataa aaggcgaagg agcaatcgaa gtcgaacggg     60
tagaaggtgt gaatctcgag tgcgagaccg aagcttaaac tcgagagagc cttctgccaa    120
catgtcttcc gtatttgacg agtatgaaca gctcctcgcg gctcagactc gccctaatgg    180
agctcacgga ggaggagaga aggggagcac cttaaaagtt gaagtcccgg tattcactct    240
taacagtgac gacccagaag atagatggaa ctttgcagta ttctgtctta agattgctgt    300
tagcgaagat gccaacaaac cactcagaca aggtgctctc atatctctct tatgctccca    360
ttctcaagtg atgaggaacc atgtcgccct tgcagggaaa cagaatgagg ccacactggc    420
tgttcttgag atcgatggtt tcaccaacag cgtgcctcaa tttaacaaca ggagtggagt    480
gtctgaggag agagcacaga gattcttgat gatagcaggg tccctccctc gggcatgcag    540
caacggtacc ccgttcatca cagctggggt tgaagataat gcaccagaag acatcactga    600
```

```
tactctggaa agaatcatct ctatccaggc tcaagtatgg gtcacggtag caaaggccat    660
gactgcatat gagacagcgg atgagtcgga aacaagaaga atcaataagt atatgcagca    720
aggcagagtc caaaagaagt acatcctcca ccccgtatgt aggagcgcaa ttcaactcac    780
gattagacaa tctctggcag tccgcatttt cttggttagc gagcttaaga gaggccgcaa    840
cacggcaggt ggaagttcca cttattatag cttggtaggg acatagact catacatcag     900
gaacaccggg cttactgcat tcttcctgac actcaggtat ggaattaaca ccaagacatc    960
agcccttgca ctcagcagcc tcgcaggcga tatccaaaaa atgaagcagc tcatgcgtct   1020
atatcggatg aaaggagata atgcgccgta catgacactg ctcggtgaca gtgaccagat   1080
gagctttgca ccggctgagt atgcacaact ctactctttc gcaatgggta tggcatccgt   1140
cctagacaaa ggaactggca agtaccagtt cgccagagac tttatgagca catcattctg   1200
gagacttgga gtagagtatg ctcgggctca gggaagcagc atcaatgagg atatggctgc   1260
cgagctaaag ctgaccccag cggcaaggag gggcctggca gctgctgccc aacgagcgtc   1320
cgaggagacc ggcagcatgg acattcccac tcaacaagct ggggtcctca cagggctcag   1380
cgacggaggc cctcaagccc cacaaggtgg actgaacagg tcgcaagggc aaccggacgc   1440
cggagatggg gagacccaat ttttagattt gatgagagca gtggcaaata gtatgagaga   1500
agcgccaaac tctgtgcaga acaccactca gcaggagcct ccatctactc ctgggccatc   1560
tcaagacaac gacaccgact ggggatactg accgacaaca ctcagcctgc ctccatcgaa   1620
ttatctcgat tcttctgcct gtaacctaac ccctggtcca caggctcaca cggccaaacc   1680
cgcaaacgag cccccccctc tctcccccccc ccctccagcc acacggctcc aaccgcccaa   1740
aacaacacgg gcacaactcg actcactcat aatctacaca gagccgaaga tcttagaaaa   1800
aaatacggac acaagagaga cattcagaga tcaggacaaa tcatcagggt ctccgctctc   1860
ccctctaccc agcagaccag agtgaagatg gccaccttca cggatgcaga gatcgacgat   1920
ctatttgaaa ccagtggaac tgtcattgac agcataatta cggcccaagg caacccagta   1980
gagaccgttg gaaggagcgc aatcccacaa ggcaaaacta agcattgag  tgcagcatgg    2040
gagaaacatg gaagcaccca accgccggcc ggccaagaca cccctgatcg aatggacaga   2100
tcagacaaac aaccatcccc acccgaacag gcaaccacac acaacagccc gccagccaca   2160
tccaccgacc agcccccccac ccaggccgca ggcgaagccg gcgacacaca gctcaagact   2220
ggagcaagca actccctcct gtcgatgctc gacaagctta gcaataaatc gtccaatgct   2280
aaaaagggcc cacggtcgag tccccaggaa gggcaccacc aacctccgac ccagcagcaa   2340
gggagtcaac agagccgcgg aaacagtcag gagagatcgc aaaaccaggt caaggccgcc   2400
tctggagacc agggcacaga cgcgaacaca gcatatcatg gacaatggaa ggagtcacaa   2460
ccatcagctg gtgcaatccc tcatgctctc cggtcagggc agagccaagc caatactcct   2520
gcatctgtgg atcatgtcca gctacctgtc gactttgtgc aggcgatgat gtctatgatg   2580
gaggcgatat cacagaaggt aaataaagtc gactatcagc tagaccttgt ctcaaagcag   2640
acatcctcca tccccatgat gcgatctgaa atccaacagc tgaaaacatc cgttgcggtc   2700
atggaagcca acctgggcat gatgaagatt ctggaccctg gttgtgctaa cgtttcatct   2760
ttaagtgacc tacgggcggt cgcccgctct cacccagttt tagtttcagg ccccggagac   2820
ccatctcctt atgtgacaca agggggtgaa ttgatactca ataaactctc gcaaccagtg   2880
caacatcctt ctgagttgat taaacctgcc acgataagcg ggcctgatat aggagtggag   2940
aaggacactg tccgtgcatt gatcacctca cgcccaatgc atccgagctc ttcagctaag   3000
```

```
ctcctgagta agctggatgc agccgggtcg atagaagaaa ttaggaaaat caaacgcctt   3060
gcgctgaatg gctgatcact actacaaccc gcaacgggtt cccgtttatc tattgtcaca   3120
aggaacccgc cccgagccct cctctataaa cccaagattc aaggctccag cgataacctt   3180
ctcccgcctc ttccatccca ctgaatgatc gcgcagctgc aattaatcta gcaacattaa   3240
agattaagaa aaaatacggg tagaatcgga gtgcaccgat tgtgccaaga tggactcatc   3300
taggacaatt gggttatact ttgattctgc ccttccttct agcaacctgt tagcattccc   3360
gattgtctta cgagatgtag gagatggaaa gaagcgaatt actccgcaat ataggatccg   3420
gcgtcttgac tcgtggacag acagtaaaga agactcggta ttcatcacta cctacggatt   3480
catcttccag gttgggaatg aagaagtcac tgtcggcatg atcaatgata atcccaagcg   3540
agagttactc tccgctgcga tgctctgcct aggaagcgtc ccgaatgttg gagatcctgt   3600
tgagctggca agggcctgcc tcactatggt ggtaacatgc aagaagagtg caactaatac   3660
tgagagaatg gtcttctcag tagtgcaggc accccgggtg ctgcaaagct gtagggtcgt   3720
ggcagacaaa tactcgtcag tgaatgcagt taagcacgtg aaagcaccag agaagatccc   3780
tgggagtgaa accctagagt acaaggtgaa ttttgtctct ttgactgtgg tgccgaagaa   3840
ggatgtctac aagatcccaa ccgcagtatt gaaggtatcc ggctcgagcc tgtataatct   3900
tgcgctcaat gtcactattg atgtggaggt agacccaaag agcccgttag tcaagtccct   3960
ttctaggtcc gacagtggat actatgctaa tctcttctta catatcggac ttatgtccac   4020
tgtagataag aggggaaaga aagtgacatt tgaccagctg gagaggaaga taaggagact   4080
tgatctaacg cgcgggctca gtgatgtgct cggaccttct gtgcttgtga aggcgagagg   4140
tgcacggact aggctgctgg cacctttctt ctctaacagc gggacagcct gctaccctat   4200
agcaaatgcc tctcctcaag tagctaagat actctggagt cagaccgcgt gcctgcggag   4260
tgtaaaaatc attattcaag cgggcaccca acgcgctgtc gcagtgactg ctgaccatga   4320
ggttacctct actaagatag agaagaggca taccatcgct aaatacaatc ccttcaagaa   4380
ataggccgta tccctgagac tgcaattcac ccgccttccc aaaacaccat gacaccagat   4440
aatgatctgt cttgattact tacagttagt ttccctgtct atcaaattag aaaaaacacg   4500
ggtagaagag ttcggatccc ggccggcgca ccaaaagcgc aagatgggcc ccagatcttc   4560
taccaggatc ccagtacctc taatgctgac catacggatc acgctggcac tgagttatgt   4620
ccgtctgaca agttctcttg atggcaggcc tcttgcagcc gcagggatcg tggtaacagg   4680
ggataaagca gttaacatat acacctcatc ccagacaggg tcagtcatag tcaagttact   4740
cccaaatatg cccaaggaca aagaggcatg tgcaaaagcc ccattggagg cttacaacag   4800
gacactgact actttgctta cccccttgg tgattctatc cgcaggatac aagagtctgt   4860
gactacatcc ggaggaagga gacagagacg ctttataggt gccattattg gcagtgtagc   4920
tctagggggt tgcaacagctg cacagataac ggcagcctcg gctctgatac aagccaacca   4980
gaatgctgct aacatcctcc ggcttaagga gagcattgct gcaaccaatg aagctgtaca   5040
cgaggtcact ggcggattgt cacagttagc agtggcagtt ggaaagatgc agcaatttgt   5100
taatgaccag tttaataaca cagctcaaga gttggactgt ataaaaatta cacagcaggt   5160
tggtgtgaaa ctcaacttat acttaactga attgactaca gtgttcgggc cacaaatcac   5220
ttcccctgcc ttaactcagt tgactgttca ggctctttac aatctggctg gtggtaatgt   5280
agattacttg ttgactaagt taggtgtagg gaacaaccag ctcagctcat tgattggtag   5340
cggcctgatc accggtaacc ctatttttta cgactcacag actcaactct tgggcataca   5400
```

```
ggtgacttta ccctcagtcg ggaacctaaa taatatgcgt gccacctact tggagacctt    5460
gtctgtaagc acaacaaagg gatttgcctc agcacttgtc ccaaaagtag tgacacaggt    5520
cggttctgtg atagaagagc ttgacacctc atactgtata gaagctgatt tggatttata    5580
ttgtacaaga atagtgacat tccctatgtc ccctggtatt tattcctgtt tgagcggcaa    5640
tacatcggct tgcatgtatt caaggactga aggcgcactt actacaccat acatgactct    5700
caaaggctca gttgttgcca attgccagat gacaacatgt agatgtgcag accccccggg    5760
tatcatatca caaaattatg gagaggctgt gtctctaata gataagcact catgcaatgt    5820
cgtatcctta gacgggataa ctttgaggct cagtggggaa tttgatgcaa cttatcaaaa    5880
gaatatctca atattagatt ctcaagtact agtgacaggc aatctcgata tctcaactga    5940
gcttgggaat gtcaaccact caataagtaa tgctttggat aagttagagg aaagcaacag    6000
caaactagac aaagtcaatg tcaaactgac cagcacatct gctctcatta cctatattgt    6060
tttaactgtc atatctcttg ttcttggtat gcttagcctg gttctagcat gctatctgat    6120
gtacaagcaa aaagcgcaac gaaagacctt gttgtggctt ggaataata ccctagatca    6180 gatgagagcc actacaaaaa ggtgaatgca gatgagaggc agaggtatcc ccaatagcaa    6240
tctgtgtgtc aattctggca gcctgttaat cagaagaatt aagaaaaaac taccggatgt    6300
aggtgaacaa aagggaatat acgggtagaa cggcctgaga ggccacccct caatcgggag    6360
ccaggcccca ctacgtccgc tctaccgcaa caccaacagc agtcttcagt catggacagc    6420
gcagttagcc aagttgcgct agagaatgat agaagagaag cgaataatac atggcgcttg    6480
gttttccgga tcgcagcctt acttttactg gtaataacct tagccgtctc tgcagtcgcc    6540
ctggcatata gtatggaggc tagcacacct ggcgaccttg taagcatacc gactgcgatc    6600
tctagggcag aggaaaggat tacatctgca ctcggttcca atcaagatgt agtagatagg    6660
atatacaagc aagtggccct tgagtctcca ttggcactgc taaataccga atctataatt    6720
atgaatgcaa taacgtctct ctcttatcaa atcaatggag ccacaaataa tagcgggtgt    6780
ggggcacctg ttcatgaccc agattacatc gggggggatag gtcaagaact tattgtagat    6840
gatacgagtg acgtcacatc atttcatccc tctgcattcc aagaacacct gaattttatc    6900
ccggcgccca ctacaggatc aggctgcact cggataccct cattgacat gagtgctacc    6960 cattactgtt acactcacaa tgtgatattg tctggctgca gagatcactc acactcacat    7020
cagtatttag cacttggtgt gcttcggaca tctgcaacag ggagggtatt cttttctact    7080
ctgcgttcca tcaacttgga tgacgcccaa aatcggaagt cttgcagtgt gagtgcaact    7140
cctttaggtt gtgatatgct gtgctctaaa atcacagaga ctgaggaaga ggattataaa    7200
tcagttatcc ccacatcgat ggtacatgga aggtttgggt ttgacggcca ataccatgag    7260
aaggacctag acgtcacaac actatttagg gactgggtgg caaattaccc aggagtagga    7320
ggtgggtctt ttattaacaa tcgcgtatgg ttcccggtct acggagggct aaaacccagc    7380
tcgcctagtg acactgcaca agaagggaga tacgtaatat acaagcgata caatgacaca    7440
tgcccggatg agcaagatta ccagattcgg atggctaagt catcgtataa gcctaggcgg    7500
tttggtggaa aacgcgtaca gcaggccatc ctatccatca aggtgtcaac atccttgggt    7560
gaggacccgg tgttgactgt accgcctaat acggtcgcac tcatggggc cgaaggcaga    7620 gttctcacag tggggacatc tcatttctta tatcagcgag ggtcatcata cttctctccc    7680
gctttgttat accctatgac agtcaacaac aaaacagcca ctcttcataa tccttataca    7740
ttcaatgctt tcactcggcc aggtagtgtc ccttgccagg cttcagcaag atgccccaac    7800
```

```
tcatgtgtta ccggagtcta tactgatcca tatcccttag tcttccatag gaaccacacc   7860
ttgcgagggg tattcggaac aatgcttgat gacgaacaag caagactcaa ccctgtatct   7920
gcagtatttg ataacatatc ccgcagtcgc ataactcggg taagttcaag cagtaccagg   7980
gcagcataca cgacatcaac gtgttttaaa gttgtcaaga ccaataaaac ctattgcctc   8040
agcattgcag aaatatccaa taccctcttc ggggaattca gaattgtccc cttactagtt   8100
gagattctca aggatggtgg ggtttaagaa gctaggaatg gtcggttgag tcaaccgtga   8160
gaaggcgggg aagatgatat tgcatcatct atcttctgta acaccaagaa tcaaatcgaa   8220
taccagtgcg agttcgaatc ctacgctgcc agtcagccat aatcggctgg tgctaatgtg   8280
gttagcctga atcttgtcga tagtcacttg attaagaaaa aatgtggacg gtggtgaaat   8340
acaaggcaaa acagctcaca gaccacagca cgggtaggac atggcgggct ccggacccga   8400
aagggcagag catcagatta tcctaccaga gtcacatctg tcctcaccat tggtcaagca   8460
taaattgctt tattactgga aattaactgg gctaccgctt cctgacgaat gtgacttcga   8520
ccatcttatt atcagccgac aatggaagaa ggtacttgaa tcggccaccc ctgacattga   8580
gagaatgata aaactagggc gggcagtaca ccagactctc aaccacaatt ccaggataac   8640
cggagtactc catccccggt gtttagagga actggctagt attgaggttc ctgattcaac   8700
caacaaattt cggaagatcg aaaaaaagat ccagattcac aacacaaggt atggagaact   8760
gttcacaaga ttatgcacgc atgtagaaaa gaaactattg gggtcatctt ggtctaacaa   8820
tgtcccacgg tcagaggaat tcaacagcat ccgtacagat ccggcatttt ggtttcactc   8880
aaaatggtcc acagccaaat ttgcatggct ccatataaaa caggtccaga ggcatctgat   8940
tgtagcagca agaacaaggt ccgcagtcaa caaattagtg acgctgaccc ataaggtagg   9000
ccaaatcttt gttactcctg agcttgtcat tgtgacacat acagatgaga acaagttcac   9060
gtgtcttacc caggaacttg tgttgatgta tgcagatatg atggagggca gagatatggt   9120
cagcataata tcatccacgg cggcacatct taggagctta tcagagaaaa ttgatgatat   9180
tctgcggtta gtagatgctc tggcaagaga tttgggcaat caagtctacg atgttgtagc   9240
actaatggag ggattcgcat acggcgctgt tcagctgctt gaaccgtcag gtacatttgc   9300
gggggatttc ttcgcattca acctgcagga gctcaaagat actctaaccg gactcctccc   9360
caaggatatc gcagaatctg tgactcacgc aatcgcaacc atattctctg cttagaaca   9420
aaatcaagca gctgagatgt tgtgcctgtt gcgtctgtgg ggtcacccac tactcgagtc   9480
ccgtattgca gcaaaagcag ttaggagtca aatgtgcgca ccaaaaatgg tagactttga   9540
tatgatcctc caggtattat ctttccttaa aggaacaatc atcaatggat atagaaagaa   9600
gaatgcaggc gtgtggccac gtgtcaagat agatacgata tacgggaagg tcatagggca   9660
gctacacgca gattctgcag agatttcaca tgatgtcatg ttgagggaat acaagagttt   9720
atctgcactt gaattcgagc catgtataga gtatgaccct gtcaccaatc tgagcatgtt   9780
tttaaaagac aaggcaatcg cacacccgaa agacaactgg ctcgcttcgt ttaggcgaaa   9840
ccttctctct gaggaccaga agaaacatgt aagagaggca acctcaacta accgcctctt   9900
gatagagttc ttagagtcaa atgattttga tccatataaa gagatggaat atctgacgac   9960
ccttgagtac ctaagagatg ataatgtggc agtatccatac tcactcaaag aaaaagaggt  10020
gaaagttaat gggcggattt tcgcaaagct aacaaataga ttaaggaatt gtcaggtaat  10080
ggcagaaggc atcctagctg accagattgc acctttcttc cagggaaatg gggtcattca  10140
ggatagcata tctttgacta aaagtatgct agcgatgagt caactgtctt tcaacagcaa  10200
```

```
caagaaacgt attactgact gcaaagaaag agtatcctca aaccgcaatc atgatccgaa   10260
gagcaagaat cgtcggagag ttgccacttt tgtaactacc gacctgcaaa agtattgtct   10320
caattggaga tatcgacag tcaagctgtt cgcacatgcc atcaatcagc tgatgggctt    10380
acctcacttc ttcgagtgga ttcatcttag actaatggat actacgatgt tgtagggga    10440 cccttcaat cctccaagtg accctacgga ctgtgatcta tcaagagtcc caaatgatga    10500
catatatatt gtcagtgcta ggggaggcat tgagggatta tgccagaagc tatggacaat   10560
gatctcaatt gctgcaatcc agcttgctgc agcaagatca cattgtcgcg ttgcctgtat   10620
ggtacaaggc gacaatcaag taatagctgt aacgagagag gtaagatcag atgactcccc   10680
agagatggtg ttaacacaat tgcatcaagc cagtgataat ttcttcaagg aattgattca   10740
tgtcaatcat ttgatcggcc ataatttgaa ggatcgtgaa accatcaggt cagacacgtt   10800
cttcatatac agcaaacgaa tattcaaaga tggagcaata ctcagtcagg tcctcaaaaa   10860
ttcatctaaa ttagtgctaa tatcaggcga ccttagtgaa aacactgtaa tgtcttgtgc   10920
caacattgca tctactgtag cacggttatg cgagaacggg cttcctaagg atttctgtta   10980
ttacttaaac tacttaatga gttgcgtgca gacatacttc gattccgaat tttccatcac   11040
caacaactcg caactcgatt ctaaccagtc gtggatagag gacatttctt ttgtgcactc   11100
atatgtcctg acccctgctc aactgggggg actgagtaac cttcaatact caaggctcta   11160
cacaaggaac atcggcgacc cgggaaccac tgctttcgca gagatcaaga gattagaggc   11220
agtggggtta ctgagtccta gcattacgac taacatctta actaggccgc ctggaaatgg   11280
agattgggcc agtctgtgca acgatccata ctcctttaat tttgggactg tcgcaagccc   11340 aaaatattgtc cttaagaaac atacacaaag agtcctattt gaaacttgct cgaatccttt   11400
attatctgga gtgcacacag aggataatga ggcagaagag aaggcattgg ctgaattctt   11460
gctcaatcaa gaaatgattc atccacgtgt cgcgcatgct atcacggaag caagctctgt   11520
aggtaggaga aagcaaattc aggggcttgt tgacacaaca aacaccgtga ttaagattgc   11580
actgactagg aggccactcg gcatcaagag gctgatgcgg atagtcaatt actcgagcat   11640
gcatgcaatg ctatttagag atgatgtttt ctcgtctaat agatccaacc atcccttagt   11700
ctcttctgat atgtgttctc tgacactggc agactatgca cggaacagaa gctggtcacc   11760
tttgacaggg ggtagaaaaa tactgggtgt atctaatcct gataccatag aacttgtaga   11820
gggtgagatc cttagtgtca gtggagggtg cactagatgt gacagtgggg atgaacagtt   11880
tacttggttc catcttccaa gcaatataga gctaaacgat gacaccagca agaatcctcc   11940
aatgagagtg ccatatctcg ggtcaaagac tcaagagagg agagccgcct cgcttgcgaa   12000
aatagctcat atgtcaccac acgtgaaggc ggctctaagg gcgtcatctg tgttaatctg   12060
ggcttatggg gacaacgaaa taaactggac tgctgcccct taagattgcaa ggtctcggtg   12120 caacataagc tcagagtatc ttcgactatt gtcacccttg cctacagctg gaatctcca    12180 acatagattg gacgacggca taactcagat gacattcacc cctgcatctc tatacagggt   12240
gtcaccttac attcatatat ctaatgattc tcaaaggcta tttactgaag aaggagtcaa   12300 agagggaat gtggtttatc agcaaatcat gctcttgggt ttgtccttaa ttgagtcact   12360
cttcccaatg acaacaacca agacatatga tgaaatcaca ttgcacctcc acagtaaatt   12420
tagctgctgt atcagggaag cacctgttgc agttcctttc gagctactcg ggtggcacc    12480 ggaactaagg gcagtaacct caaataagtt tatgtatgat cctagccctg tatcagaggg   12540
agactttgcg agacttgact tagctatctt taagagttat gaacttaatt tagagtcata   12600
```

```
ttccacaata gagctaatga acgttctttc aatatctagt gggaagttga ttggccagtc    12660
tgtggtttct tatgatgaag atacctccat aaagaatgac gctataatag tgtatgacaa    12720
cacacggaat tggatcagcg aagctcagaa ttcagatgtg gtccgcctat tcgagtatgc    12780
ggcactcgaa gtgctcctcg actgttctta tcaactctac tatctgagag taagaggcct    12840
aaacaatatc gtcctgtaca tgagtgattt atacaagaat atgccaggaa ttctactctc    12900
taatattgca gccacaatat ctcaccctgt catccattca aggttgaatg cagtaggtct    12960
ggtcaaccat gacgggtcac accaacttac agacacagat ttcattgaaa tgtctgcaaa    13020
gctgctagtc tcttgcactc gacgcgtggt ctcaggttta catgcaggga ataagtatga    13080
cctgctgttt ccatctgtct tggatgataa cctaagtgag gagatgcttc agttgatatc    13140
ccaattatgc tgtctgtata cggtgctctt tgctacaaca agagaaatcc cgaaaataag    13200
aggcttatct gcagaagaga atgttcagt acttactgag tacctactgt cagatgctgt    13260
gaaaccgtta cttgggtccg agcaagtgag ctctatcatg tctcccaaca tagttacgtt    13320
cccagccaat ctgtattaca tgtctaggaa gagccttaat ttgatcaggg agagagagga    13380
cagggatact atcttggcat tgttgttccc tcaagaaccg ctgctcgagt ttcctctggt    13440
acgagatatt ggtgctcgtg taaaagatcc atttacccga caacctgcgg cgttttaca    13500
agagttagat ttgagtgctc cggcaaggta tgacgcattc acaatcagtc aggcgcattc    13560
tgaacacata ttgccaaacc cagaggaaga tcacttagta cgatacttgt tcagaggaat    13620
agggactgcg tcctcctctt ggtataaggc atcccatctt ctttctgtac ccgaggtcag    13680
atgtgcaagg catgggaact ccttatattt agcagaagga agtggagcca tcatgagtct    13740
tctcgaattg catataccac acgaaactat ctattacaat acactttct cgaacgagat    13800
gaaccccccca cagcgacatt tcggaccaac tccaacacag tttctgaatt cggttgtttt    13860
taggaattta caggcggaag taccatgcaa ggatggattt gtccaggagt tccgtccgtt    13920
atggagagag aatacagaag aaagcgatct gacctcagat gaagcagtgg gatatatcac    13980
atctgtagtg ccgtacaggt ctgtatcgtt gctgcattgt gacattgaaa tccctccagg    14040
atctaatcaa agcttactag atcagctggc taccaatctg tctctgattg ccatgcattc    14100
tgtgaaggag ggcggggtcg tgattatcaa agtactgtat gcaatgggat attacttcca    14160
tctactcatg aacttgttta ctccatgttc cacgaaagga tatattctct ctaatggcta    14220
tgcctgtaga ggggatatgg agtgttacct gatatttgtc atgggctacc taggcgggcc    14280
tacatttgta catgaggtgg tgaggatggc aaaaacgcta gtacagcggc atggcacact    14340
tttgtctaag tcagatgaga ttacactgac taggttattt acttcacagc aacagcgtgt    14400
aacagacatc ctatccagcc ctttaccgag actaatgaag tacttgagag agaatattga    14460
tactgcactg attgaagccg ggggacagcc tgtccgtcca ttctgtgcag agagtttagt    14520
gagcacacta acagacatga ctcagacaac ccagatcatc gccagccaca ttgatacagt    14580
cattcgatct gtgatctata tggaagcaga gggtgatctt gctgacacag tattcttatt    14640
tacccccttac aacctctcta tggacgggaa aaagagaaca tcacttaaac agtgcacaag    14700
acagatctta gaggtcacaa tactgggtct cagagtcaaa aatctcaata agtaggtga    14760
tgtaatcagc ctagtactca gaggtatgat ttctctggag gaccttctcc cactgagaac    14820
ctacttgaag tgtagtacct gccctaagta tttgaaggct gtcctaggta ttaccaaact    14880
caaagaaatg ttcacagacg cctctcttatt atacttgact cgtgctcaac aaaaattcta    14940
catgaaaact ataggcaatg cagtcaaggg atactatagt aactgtgact cttaaaggca    15000
```

```
accacatatc aataggccct ctttctagcc gatcgtattc ttgttgactt cattatacca    15060
tattagaaaa aaattgaatt ccgacccttt aagactcgta ttcggattca ataattatc    15120 tcagaaaaaa agtgcacgta gttgttcttg attatagtcc cgtcattcac caaatctttg    15180
tttggt                                                              15186
```

```
<210> SEQ ID NO 2
<211> LENGTH: 24
<212> TYPE: DNA
<213> ORGANISM: Newcastle disease virus

<400> SEQUENCE: 2
aggagacaga gacgctttat aggt                                          24

<210> SEQ ID NO 3
<211> LENGTH: 8
<212> TYPE: PRT
<213> ORGANISM: Newcastle disease virus

<400> SEQUENCE: 3

Arg Arg Gln Arg Arg Phe Ile Gly
1               5

<210> SEQ ID NO 4
<211> LENGTH: 6
<212> TYPE: PRT
<213> ORGANISM: Newcastle disease virus
<220> FEATURE:
<221> NAME/KEY: MISC_FEATURE
<222> LOCATION: (1)..(1)
<223> OTHER INFORMATION: Xaa may be Arg or Lys
<220> FEATURE:
<221> NAME/KEY: MISC_FEATURE
<222> LOCATION: (4)..(4)
<223> OTHER INFORMATION: Xaa may be Lys or Arg

<400> SEQUENCE: 4

Xaa Arg Gln Xaa Arg Phe
1               5

<210> SEQ ID NO 5
<211> LENGTH: 6
<212> TYPE: PRT
<213> ORGANISM: Newcastle disease virus
<220> FEATURE:
<221> NAME/KEY: MISC_FEATURE
<222> LOCATION: (1)..(1)
<223> OTHER INFORMATION: Xaa may be Gly or Glu
<220> FEATURE:
<221> NAME/KEY: MISC_FEATURE
<222> LOCATION: (2)..(2)
<223> OTHER INFORMATION: Xaa may be Lys or Arg
<220> FEATURE:
<221> NAME/KEY: MISC_FEATURE
<222> LOCATION: (4)..(4)
<223> OTHER INFORMATION: Xaa may be Gly or Glu

<400> SEQUENCE: 5

Xaa Xaa Gln Xaa Arg Leu
1               5

<210> SEQ ID NO 6
<211> LENGTH: 8
<212> TYPE: RNA
<213> ORGANISM: Newcastle disease virus

<400> SEQUENCE: 6
```

```
uuuuuccc                                                            8

<210> SEQ ID NO 7
<211> LENGTH: 8
<212> TYPE: RNA
<213> ORGANISM: Newcastle disease virus

<400> SEQUENCE: 7 uuuuuccc                                                            8

<210> SEQ ID NO 8
<211> LENGTH: 10
<212> TYPE: RNA
<213> ORGANISM: Newcastle disease virus

<400> SEQUENCE: 8
ugcccaucuu                                                         10

<210> SEQ ID NO 9
<211> LENGTH: 5
<212> TYPE: RNA
<213> ORGANISM: Newcastle disease virus

<400> SEQUENCE: 9 aaucu                                                               5

<210> SEQ ID NO 10
<211> LENGTH: 10
<212> TYPE: RNA
<213> ORGANISM: Newcastle disease virus

<400> SEQUENCE: 10
ugccuguguu                                                         10

<210> SEQ ID NO 11
<211> LENGTH: 6
<212> TYPE: RNA
<213> ORGANISM: Newcastle disease virus

<400> SEQUENCE: 11 aauucu                                                              6

<210> SEQ ID NO 12
<211> LENGTH: 10
<212> TYPE: RNA
<213> ORGANISM: Newcastle disease virus

<400> SEQUENCE: 12
ugcccaucuu                                                         10

<210> SEQ ID NO 13
<211> LENGTH: 5
<212> TYPE: RNA
<213> ORGANISM: Newcastle disease virus

<400> SEQUENCE: 13 aaucu                                                               5

<210> SEQ ID NO 14
<211> LENGTH: 10
<212> TYPE: RNA
<213> ORGANISM: Newcastle disease virus

<400> SEQUENCE: 14
```
ugcccaucuu                                                            10

<210> SEQ ID NO 15
<211> LENGTH: 6
<212> TYPE: RNA
<213> ORGANISM: Newcastle disease virus

<400> SEQUENCE: 15 aauucu                                                                6

<210> SEQ ID NO 16
<211> LENGTH: 31
<212> TYPE: RNA
<213> ORGANISM: Newcastle disease virus

<400> SEQUENCE: 16
gauggccuac auccucuugu uuucccuuau a                                    31

<210> SEQ ID NO 17
<211> LENGTH: 10
<212> TYPE: RNA
<213> ORGANISM: Newcastle disease virus

<400> SEQUENCE: 17
ugcccaucuu                                                            10

<210> SEQ ID NO 18
<211> LENGTH: 6
<212> TYPE: RNA
<213> ORGANISM: Newcastle disease virus

<400> SEQUENCE: 18 aauucu                                                                6

<210> SEQ ID NO 19
<211> LENGTH: 47
<212> TYPE: RNA
<213> ORGANISM: Newcastle disease virus

<400> SEQUENCE: 19
acaccugcca ccacuuuaug uuccguuuug ucgagugucu ggugucg                   47

<210> SEQ ID NO 20
<211> LENGTH: 10
<212> TYPE: RNA
<213> ORGANISM: Newcastle disease virus

<400> SEQUENCE: 20
ugcccauccu                                                            10

<210> SEQ ID NO 21
<211> LENGTH: 5
<212> TYPE: RNA
<213> ORGANISM: Newcastle disease virus

<400> SEQUENCE: 21 aaucu                                                                 5

<210> SEQ ID NO 22
<211> LENGTH: 55
<212> TYPE: RNA
<213> ORGANISM: Newcastle disease virus

<400> SEQUENCE: 22
ugguuugucu cuuaggcacu cuaugcuauu uuccgcuucc ucguuagcuu cagcu          55

<210> SEQ ID NO 23
<211> LENGTH: 10
<212> TYPE: RNA
<213> ORGANISM: Newcastle disease virus

<400> SEQUENCE: 23
ugcccaucuu                                                            10

<210> SEQ ID NO 24
<211> LENGTH: 11
<212> TYPE: RNA
<213> ORGANISM: Newcastle disease virus

<400> SEQUENCE: 24
aaucuuuuuu u                                                          11

<210> SEQ ID NO 25
<211> LENGTH: 10
<212> TYPE: RNA
<213> ORGANISM: Newcastle disease virus

<400> SEQUENCE: 25
ugccuguguu                                                            10

<210> SEQ ID NO 26
<211> LENGTH: 11
<212> TYPE: RNA
<213> ORGANISM: Newcastle disease virus

<400> SEQUENCE: 26
aaucuuuuuu u                                                          11

<210> SEQ ID NO 27
<211> LENGTH: 10
<212> TYPE: RNA
<213> ORGANISM: Newcastle disease virus

<400> SEQUENCE: 27
ugcccaucuu                                                            10

<210> SEQ ID NO 28
<211> LENGTH: 10
<212> TYPE: RNA
<213> ORGANISM: Newcastle disease virus

<400> SEQUENCE: 28
aaucuuuuuu                                                            10

<210> SEQ ID NO 29
<211> LENGTH: 10
<212> TYPE: RNA
<213> ORGANISM: Newcastle disease virus

<400> SEQUENCE: 29
ugcccaucuu                                                            10

<210> SEQ ID NO 30
<211> LENGTH: 9
<212> TYPE: RNA
<213> ORGANISM: Newcastle disease virus

<400> SEQUENCE: 30

-continued aucuuuuuu                                                                 9

<210> SEQ ID NO 31
<211> LENGTH: 31
<212> TYPE: RNA
<213> ORGANISM: Newcastle disease virus

<400> SEQUENCE: 31
gauggccuac auccacuugu uuucccuuau a                                       31

<210> SEQ ID NO 32
<211> LENGTH: 10
<212> TYPE: RNA
<213> ORGANISM: Newcastle disease virus

<400> SEQUENCE: 32
ugcccauccu                                                               10

<210> SEQ ID NO 33
<211> LENGTH: 11
<212> TYPE: RNA
<213> ORGANISM: Newcastle disease virus

<400> SEQUENCE: 33
uaaucuuuuu u                                                             11

<210> SEQ ID NO 34
<211> LENGTH: 47
<212> TYPE: RNA
<213> ORGANISM: Newcastle disease virus

<400> SEQUENCE: 34
acaccugcca ccacuuuaug uuccguuuug ucgagugucu ggugucg                      47

<210> SEQ ID NO 35
<211> LENGTH: 10
<212> TYPE: RNA
<213> ORGANISM: Newcastle disease virus

<400> SEQUENCE: 35
ugcccauccu                                                               10

<210> SEQ ID NO 36
<211> LENGTH: 11
<212> TYPE: RNA
<213> ORGANISM: Newcastle disease virus

<400> SEQUENCE: 36
aaucuuuuuu u                                                             11

<210> SEQ ID NO 37
<211> LENGTH: 114
<212> TYPE: RNA
<213> ORGANISM: Newcastle disease virus

<400> SEQUENCE: 37
uaacuuaagg cugggaaauu cugagcauaa gccuaaguuu auuaauagag ucuuuuuuc         60 acgugcauca acaagaacua auaucagggc aguaaguggu uuagaaacaa acca             114